US010295538B2

(12) United States Patent
Amicosante et al.

(10) Patent No.: US 10,295,538 B2
(45) Date of Patent: May 21, 2019

(54) MYCOBACTERIUM TUBERCULOSIS PROTEINS

(71) Applicant: Oxford Immunotec Limited, Oxfordshire (GB)

(72) Inventors: Massimo Amicosante, Rome (IT); Ian Durrant, Stoke Mandeville (GB); Scott Tasker, Oxford (GB)

(73) Assignee: Oxford Immunotec Limited, Oxfordshire (GB)

( * ) Notice: Subject to any disclaimer, the term of this patent is extended or adjusted under 35 U.S.C. 154(b) by 0 days.

(21) Appl. No.: 15/503,151

(22) PCT Filed: Aug. 14, 2015

(86) PCT No.: PCT/GB2015/052362
§ 371 (c)(1),
(2) Date: Feb. 10, 2017

(87) PCT Pub. No.: WO2016/024129
PCT Pub. Date: Feb. 18, 2016

(65) Prior Publication Data
US 2017/0234871 A1 Aug. 17, 2017

(30) Foreign Application Priority Data

Aug. 15, 2014 (BG) .................................. 111804
Jun. 30, 2015 (BG) .................................. 112045

(51) Int. Cl.
| A61K 39/04 | (2006.01) |
| A61K 39/00 | (2006.01) |
| G01N 33/53 | (2006.01) |
| G01N 33/569 | (2006.01) |
| A61K 38/16 | (2006.01) |
| C07K 14/35 | (2006.01) |
| G01N 33/50 | (2006.01) |
| G01N 33/68 | (2006.01) |

(52) U.S. Cl.
CPC ....... *G01N 33/5695* (2013.01); *A61K 38/164* (2013.01); *A61K 39/04* (2013.01); *C07K 14/35* (2013.01); *G01N 33/5091* (2013.01); *G01N 33/6866* (2013.01); *G01N 2333/35* (2013.01); *G01N 2333/57* (2013.01); *G01N 2333/70514* (2013.01); *G01N 2333/70517* (2013.01); *G01N 2469/10* (2013.01)

(58) Field of Classification Search
CPC ................................ A61K 39/00; A61K 39/04
USPC ......... 424/184.1, 185.1, 234.1, 248.1; 435/4, 435/7.1, 7.2
See application file for complete search history.

(56) References Cited

U.S. PATENT DOCUMENTS

| 7,785,607 B2 | 8/2010 | Goletti et al. |
| 7,838,013 B2 * | 11/2010 | Andersen ............... C07K 14/35 |
| | | 424/185.1 |
| 2007/0196878 A1 | 8/2007 | Goletti et al. |
| 2008/0171345 A1 | 7/2008 | Belisle et al. |

FOREIGN PATENT DOCUMENTS

| CN | 103884847 A | 6/2014 |
| WO | WO-2003/004520 A2 | 1/2003 |
| WO | WO-2005/090988 A2 | 9/2005 |
| WO | WO-2006/000045 A1 | 1/2006 |
| WO | WO-2007/131293 A1 | 11/2007 |
| WO | WO-2010/010179 A1 | 1/2010 |

OTHER PUBLICATIONS

Al-Khodari, N.Y. et al., Identification, Diagnostic Potential, and Natural Expression of Immunodominant Seroreactive Peptides Encoded by Five *Mycobacterium tuberculosis*-Specific Genomic Regions, Clincal and Vaccine Immunology, 18(3):477-482 (2011).
Amicosante, M. et al., Computer-Based Design of an HLA-Haplotype and HIV-Clade Independent Cytotoxic T-Lymphocite (CTL) Assay for Monitoring HIV-Specific Immunity, Molecular Medicine, 8(12):798-807 (2002).
Contini, S. et al., A model of phenotypic susceptibility to Tuberculosis: Deficient in silico selection of *Mycobacterium tuberculosis* epitopes by HLA alleles, Sarcoidosis Vasculitis and Diffuse Lung Disease, 25(1):21-28 (2008).
De Souza, G.A. et al., Bacterial proteins with cleaved or uncleaved signal peptides of the general secretory pathway, Journal of Proteomics, 75(2):502-510 (2011).
Griffin, J.E. et al., High-Resolution Phenotypic Profiling Defines Genes Essential for Mycobacterial Growth and Cholesterol Catabolism, PLoS Pathogens, 7(9):e1002251 (2011).
International Search Report for PCT/GB2015/052362, 9 pages (dated Jan. 18, 2016).

(Continued)

*Primary Examiner* — Rodney P Swartz
(74) *Attorney, Agent, or Firm* — Choate, Hall & Stewart LLP; Charles E. Lyon; Brian E. Reese

(57) ABSTRACT

The present invention relates to *Mycobacterium tuberculosis* (*M tuberculosis*) proteins and immunologically active fragments (peptides or mimotope peptides) thereof. In particular, the invention relates to a group of *M. tuberculosis* proteins and peptides thereof that are both highly antigenic and characteristic of clinical strains of *M. tuberculosis*. Accordingly, the further relates to the use of these *M. tuberculosis* proteins or peptides in diagnosing, treating or preventing *M. tuberculosis* complex infection.

38 Claims, 15 Drawing Sheets

Specification includes a Sequence Listing.

(56) References Cited

OTHER PUBLICATIONS

Jeffrey, H. et al., The Preparation and Characterization of Poly(lactide-co-glycolide) Microparticles. II. The Entrapment of a Model Protein Using a (Water-in-Oil)-in-Water Emulsion Solvent Evaporation Technique, Pharmaceutical Research, 10(3):362-368 (1993).

Lewinsohn, D.M. et al., Human *Mycobacterium tuberculosis* CD8 T Cell Antigens/Epitopes Identified by a Proteomic Peptide Library, PLoS One, 8(6):e67016 (2013).

Meziere, C. et al., In vivo T helper cell response to retro-inverso peptidomimetics, The Journal of Immunology, 159:3230-3237 (1997).

Saltini, C. et al., *M. avium* binding to HLA-DR expressed alleles in silico: a model of phenotypic susceptibility to sarcoidosis, Sarcoidosis Vasculitis and Diffuse Lung Diseases, 25(2):100-116 (2008).

Seghrouchni, F. et al., Design of immunogenic peptides from *Mycobacterium tuberculosis* genes expressed during macrophage infection, Tuberculosis, 1-8 (2009).

Vincenti, D. et al., Indentification of Early Secretory Antigen Target-6 Epitopes for the Immunodiagnosis of Active Tuberculosis, Molecular Medicine, 8(3/4):105-111 (2003).

Written Opinion for PCT/GB2015/052362, 11 pages (dated Jan. 18, 2016).

\* cited by examiner

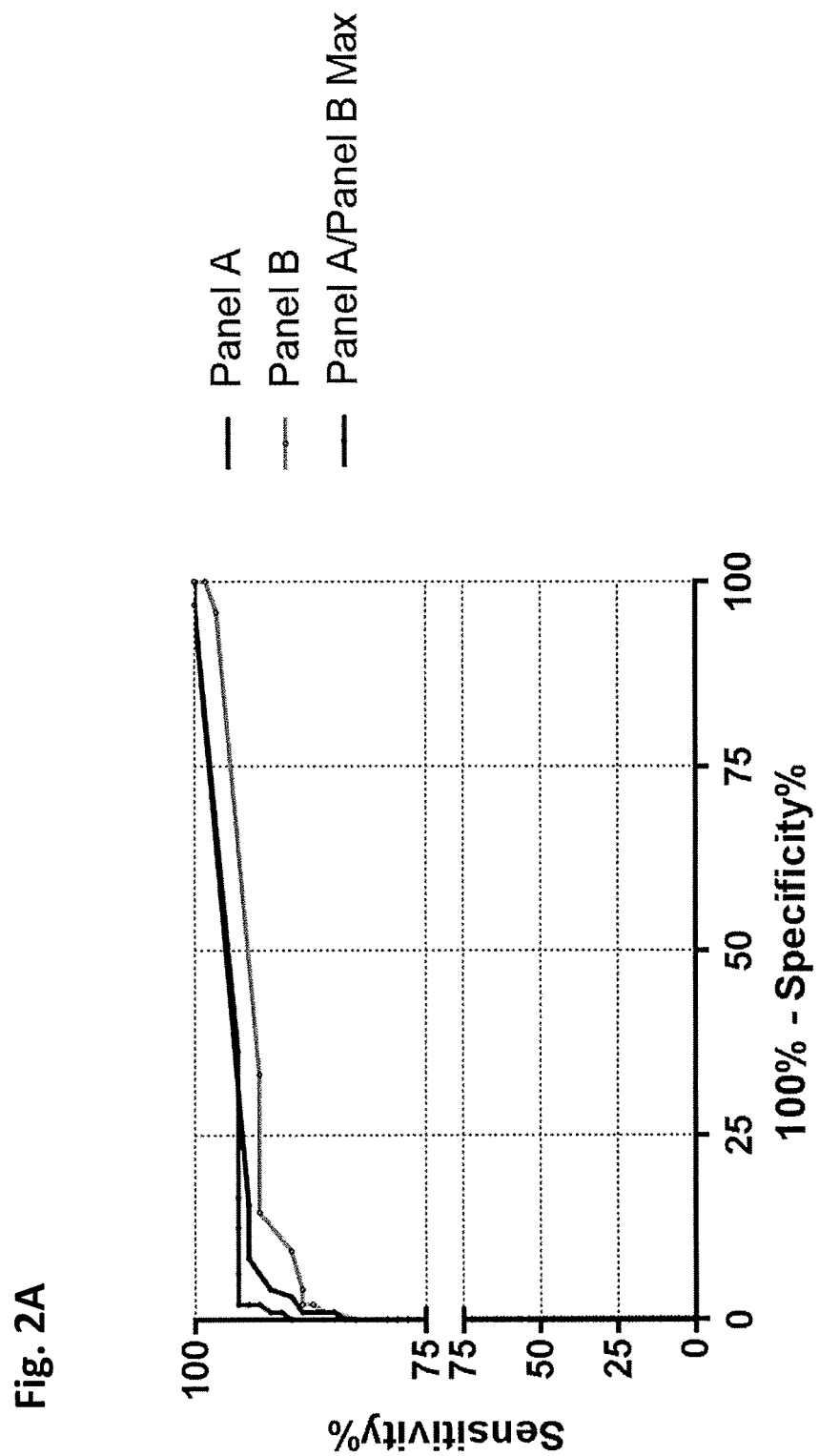

Fig. 2B

| Cut off | Sensitivity % | 95% Confidence Interval (CI) | Specificity % | 95% CI | Likelihood Ratio |
|---|---|---|---|---|---|
| > -0.5000 | 100 | 95.85% to 100.0% | 3.125 | 0.6491% to 8.862% | 1.032 |
| > 0.5000 | 95.4 | 88.64% to 98.73% | 63.54 | 53.09% to 73.13% | 2.617 |
| > 1.500 | 95.4 | 88.64% to 98.73% | 83.33 | 74.35% to 90.16% | 5.724 |
| > 2.500 | 95.4 | 88.64% to 98.73% | 87.5 | 79.18% to 93.37% | 7.632 |
| > 3.500 | 95.4 | 88.64% to 98.73% | 93.75 | 86.89% to 97.67% | 15.26 |
| > 4.500 | 95.4 | 88.64% to 98.73% | 97.92 | 92.68% to 99.75% | 45.79 |
| > 6.000 | 94.25 | 87.10% to 98.11% | 97.92 | 92.68% to 99.75% | 45.24 |
| > 7.500 | 93.1 | 85.59% to 97.43% | 97.92 | 92.68% to 99.75% | 44.69 |
| > 8.500 | 91.95 | 84.12% to 96.70% | 98.96 | 94.33% to 99.97% | 88.28 |
| > 9.500 | 90.8 | 82.68% to 95.95% | 98.96 | 94.33% to 99.97% | 87.17 |
| > 11.00 | 89.66 | 81.27% to 95.16% | 100 | 96.23% to 100.0% | |

— Pool of TBFG_13463, Mtub17866, Rv2654c,
Rv3845, Rv1495, Rv0840c and Rv1677
CD4/CD8 Epitopes

SEQUENCE LISTING

```
<160> NUMBER OF SEQ ID NOS: 171

<210> SEQ ID NO 1
<211> LENGTH: 131
<212> TYPE: PRT
<213> ORGANISM: Mycobacterium tuberculosis

<400> SEQUENCE: 1

Met Thr Ile Asn Asn Gln Phe Asp Asp Ala Asp Thr His Gly Ala Thr
1               5                   10                  15
```

```
Ser Asp Phe Trp Cys Asp Ala Glu Trp Ala Gly Leu Arg Gly Pro Val
            20                  25                  30

Ala Ala Gly Leu Gly Arg Ala Ala Leu Val Gly Tyr Leu Ser Val Pro
        35                  40                  45

Gln Gly Trp Thr Glu Ala Asn Gln Ala Asn Leu Ala Ala Gly Thr Glu
    50                  55                  60

Ala Glu Pro Asn Gln Ala Leu Gly Trp Leu Pro Met Gln Asp Ile Asp
65                  70                  75                  80

Ala Ala Ala Glu Ala Ala Ala Gln Pro Ser His Ala Leu Gly Trp Leu
                85                  90                  95

Pro Ile Glu Glu Ile Asp Ala Ala Ala Ser Asp Asp Gly Glu Val Ser
            100                 105                 110

Ser Ser Pro Gln Leu Pro Pro Arg Pro Phe Met Met Pro His Thr Pro
        115                 120                 125

Ser Gly Gly
    130

<210> SEQ ID NO 2
<211> LENGTH: 59
<212> TYPE: PRT
<213> ORGANISM: Mycobacterium tuberculosis

<400> SEQUENCE: 2

Met Ile Asp Asp Arg His Lys Ser Thr Arg Arg Thr Cys Asn His Gly
1               5                   10                  15

Gly Ile Thr Trp Arg Val Ala Ala Thr Ser Ala Arg Ser Ala Arg Ser
            20                  25                  30

Leu Ala Thr Thr His Pro Glu Ala Gly His Tyr Gly Leu Ala Thr Trp
        35                  40                  45

Phe Thr Arg Met Asp Ala Met Thr Ala Pro Thr
    50                  55

<210> SEQ ID NO 3
<211> LENGTH: 81
<212> TYPE: PRT
<213> ORGANISM: Mycobacterium tuberculosis

<400> SEQUENCE: 3

Met Ser Gly His Ala Leu Ala Ala Arg Thr Leu Leu Ala Ala Ala Asp
1               5                   10                  15

Glu Leu Val Gly Gly Pro Pro Val Glu Ala Ser Ala Ala Ala Leu Ala
            20                  25                  30

Gly Asp Ala Ala Gly Ala Trp Arg Thr Ala Ala Val Glu Leu Ala Arg
        35                  40                  45

Ala Leu Val Arg Ala Val Ala Glu Ser His Gly Val Ala Ala Val Leu
    50                  55                  60

Phe Ala Ala Thr Ala Ala Ala Ala Ala Ala Val Asp Arg Gly Asp Pro
65                  70                  75                  80

Pro

<210> SEQ ID NO 4
<211> LENGTH: 119
<212> TYPE: PRT
<213> ORGANISM: Mycobacterium tuberculosis

<400> SEQUENCE: 4

Met Asp Arg Val Arg Arg Val Val Thr Asp Arg Asp Ser Gly Ala Gly
```

```
 1               5                  10                 15
Ala Leu Ala Arg His Pro Leu Ala Gly Arg Arg Thr Asp Pro G

```
                   100                 105                 110
Pro Asp Ala Val Ser Leu Thr Ile Ala Asn Ser Thr Ala Ser Ile Pro
            115                 120                 125

Glu Phe Ser Ala Ser Leu Val Ser Leu Lys Ser Cys Leu Asp Val Ala
        130                 135                 140

Thr Arg Ser Ala Ile Asp Arg His Glu Ala Ala Gly Thr Thr His Ser
145                 150                 155                 160

Ala Glu Tyr Gln Ala Ala Ile Arg Thr Trp Asn Glu Thr Tyr Leu Cys
                165                 170                 175

Arg Thr Arg Pro Trp Pro Arg Glu Leu Thr Glu Ala Phe Ala Asn Met
            180                 185                 190

Gly Thr Glu Ile Phe Glu Thr Met Phe Gly Pro Ser Asp Phe Arg Ile
        195                 200                 205

Val Gly Asn Val Arg Asp Trp Asp Val Val Asp Arg Leu Ala Asp Ile
        210                 215                 220

Ala Val Pro Thr Leu Leu Val Gly Arg Phe Asp Glu Cys Ser Pro
225                 230                 235                 240

Glu His Met Arg Glu Met Gln Gly Arg Ile Ala Gly Ser Arg Leu Glu
                245                 250                 255

Phe Phe Glu Ser Ser His Met Pro Phe Ile Glu Pro Ala Arg
            260                 265                 270

Phe Asp Arg Val Met Arg Glu Phe Leu Arg Leu His Asp Ile
        275                 280                 285

<210> SEQ ID NO 7
<211> LENGTH: 182
<212> TYPE: PRT
<213> ORGANISM: Mycobacterium tuberculosis

<400> SEQUENCE: 7

Val Thr His Ser Arg Leu Ile Gly Ala Leu Thr Val Val Ala Ile Ile
1               5                  10                  15

Val Thr Ala Cys Gly Ser Gln Pro Lys Ser Gln Pro Ala Val Ala Pro
            20                  25                  30

Thr Gly Asp Ala Ala Ala Ala Thr Gln Val Pro Ala Gly Gln Thr Val
        35                  40                  45

Pro Ala Gln Leu Gln Phe Ser Ala Lys Thr Leu Asp Gly His Asp Phe
    50                  55                  60

His Gly Glu Ser Leu Leu Gly Lys Pro Ala Val Leu Trp Phe Trp Ala
65                  70                  75                  80

Pro Trp Cys Pro Thr Cys Gln Gly Glu Ala Pro Val Val Gly Gln Val
                85                  90                  95

Ala Ala Ser His Pro Glu Val Thr Phe Val Gly Val Ala Gly Leu Asp
            100                 105                 110

Gln Val Pro Ala Met Gln Glu Phe Val Asn Lys Tyr Pro Val Lys Thr
        115                 120                 125

Phe Thr Gln Leu Ala Asp Thr Asp Gly Ser Val Trp Ala Asn Phe Gly
    130                 135                 140

Val Thr Gln Gln Pro Ala Tyr Ala Phe Val Asp Pro His Gly Asn Val
145                 150                 155                 160

Asp Val Val Arg Gly Arg Met Ser Gln Asp Glu Leu Thr Arg Arg Val
                165                 170                 175

Thr Ala Leu Thr Ser Arg
            180
```

<210> SEQ ID NO 8
<211> LENGTH: 14
<212> TYPE: PRT
<213> ORGANISM: Mycobacterium tuberculosis

<400> SEQUENCE: 8

Ala Ala Leu Val Gly Tyr Leu Ser Val Pro Gln Gly Trp Thr
1               5                   10

<210> SEQ ID NO 9
<211> LENGTH: 15
<212> TYPE: PRT
<213> ORGANISM: Mycobacterium tuberculosis

<400> SEQUENCE: 9

Gln Ala Leu Gly Trp Leu Pro Met Gln Asp Ile Asp Ala Ala Ala
1               5                   10                  15

<210> SEQ ID NO 10
<211> LENGTH: 14
<212> TYPE: PRT
<213> ORGANISM: Mycobacterium tuberculosis

<400> SEQUENCE: 10

Arg Pro Phe Met Met Pro His Thr Pro Ser Gly Gly Ala Ala
1               5                   10

<210> SEQ ID NO 11
<211> LENGTH: 15
<212> TYPE: PRT
<213> ORGANISM: Mycobacterium tuberculosis

<400> SEQUENCE: 11

Gly Gly Ile Thr Trp Arg Val Ala Ala Thr Ser Ala Arg Ser Ala
1               5                   10                  15

<210> SEQ ID NO 12
<211> LENGTH: 19
<212> TYPE: PRT
<213> ORGANISM: Mycobacterium tuberculosis

<400> SEQUENCE: 12

Gly His Tyr Gly Leu Ala Thr Trp Phe Thr Arg Met Asp Ala Met Thr
1               5                   10                  15

Ala Pro Thr

<210> SEQ ID NO 13
<211> LENGTH: 25
<212> TYPE: PRT
<213> ORGANISM: Mycobacterium tuberculosis

<400> SEQUENCE: 13

Val Trp Phe Gln Arg Ile Gly Gly Pro Gly Arg Pro Leu Leu Val
1               5                   10                  15

Val His Gly Gly Pro Gly Leu Pro His
            20                  25

<210> SEQ ID NO 14
<211> LENGTH: 21
<212> TYPE: PRT
<213> ORGANISM: Mycobacterium tuberculosis

<400> SEQUENCE: 14

-continued

```
His Ser Trp Gly Gly Met Leu Ala Gln Gln Tyr Val Leu Asp Lys Ala
1               5                   10                  15

Pro Asp Ala Val Ser
            20

<210> SEQ ID NO 15
<211> LENGTH: 13
<212> TYPE: PRT
<213> ORGANISM: Mycobacterium tuberculosis

<400> SEQUENCE: 15

Val Ser Leu Thr Ile Ala Asn Ser Thr Ala Ser Ile Pro
1               5                   10

<210> SEQ ID NO 16
<211> LENGTH: 13
<212> TYPE: PRT
<213> ORGANISM: Mycobacterium tuberculosis

<400> SEQUENCE: 16

Ala Ser Leu Val Ser Leu Lys Ser Cys Leu Asp Val Ala
1               5                   10

<210> SEQ ID NO 17
<211> LENGTH: 13
<212> TYPE: PRT
<213> ORGANISM: Mycobacterium tuberculosis

<400> SEQUENCE: 17

Ser Asp Phe Arg Ile Val Gly Asn Val Arg Asp Trp Asp
1               5                   10

<210> SEQ ID NO 18
<211> LENGTH: 13
<212> TYPE: PRT
<213> ORGANISM: Mycobacterium tuberculosis

<400> SEQUENCE: 18

Ser Arg Leu Glu Phe Phe Glu Ser Ser Ser His Met Pro
1               5                   10

<210> SEQ ID NO 19
<211> LENGTH: 13
<212> TYPE: PRT
<213> ORGANISM: Mycobacterium tuberculosis

<400> SEQUENCE: 19

Asp Arg Val Met Arg Glu Phe Leu Arg Leu His Asp Ile
1               5                   10

<210> SEQ ID NO 20
<211> LENGTH: 17
<212> TYPE: PRT
<213> ORGANISM: Mycobacterium tuberculosis

<400> SEQUENCE: 20

Met Asp Arg Val Arg Arg Val Val Thr Asp Arg Asp Ser Gly Ala Gly
1               5                   10                  15

Ala

<210> SEQ ID NO 21
<211> LENGTH: 17
<212> TYPE: PRT
<213> ORGANISM: Mycobacterium tuberculosis
```

<400> SEQUENCE: 21

Pro Gln Leu Ala Ala Phe Tyr His Arg Leu Met Thr Thr Gln Arg His
1               5                   10                  15

Cys

<210> SEQ ID NO 22
<211> LENGTH: 13
<212> TYPE: PRT
<213> ORGANISM: Mycobacterium tuberculosis

<400> SEQUENCE: 22

Ala Thr Ile Ala Val Ala Arg Lys Leu Ala Glu Arg Thr
1               5                   10

<210> SEQ ID NO 23
<211> LENGTH: 13
<212> TYPE: PRT
<213> ORGANISM: Mycobacterium tuberculosis

<400> SEQUENCE: 23

Arg Pro Tyr Gln Leu Arg Asp Thr Asn Gly Asp Pro Val
1               5                   10

<210> SEQ ID NO 24
<211> LENGTH: 13
<212> TYPE: PRT
<213> ORGANISM: Mycobacterium tuberculosis

<400> SEQUENCE: 24

Ala His Tyr His Val Asp Thr Arg Thr His Pro His Asn
1               5                   10

<210> SEQ ID NO 25
<211> LENGTH: 14
<212> TYPE: PRT
<213> ORGANISM: Mycobacterium tuberculosis

<400> SEQUENCE: 25

Asp Glu Leu Val Gly Gly Pro Pro Val Glu Ala Ser Ala Ala
1               5                   10

<210> SEQ ID NO 26
<211> LENGTH: 24
<212> TYPE: PRT
<213> ORGANISM: Mycobacterium tuberculosis

<400> SEQUENCE: 26

Gly Ala Trp Arg Thr Ala Ala Val Glu Leu Ala Arg Ala Leu Val Arg
1               5                   10                  15

Ala Val Ala Glu Ser His Gly Val
            20

<210> SEQ ID NO 27
<211> LENGTH: 14
<212> TYPE: PRT
<213> ORGANISM: Mycobacterium tuberculosis

<400> SEQUENCE: 27

Ala Ala Val Leu Phe Ala Ala Thr Ala Ala Ala Ala Ala Ala
1               5                   10

<210> SEQ ID NO 28

```
<210> SEQ ID NO 28
<211> LENGTH: 22
<212> TYPE: PRT
<213> ORGANISM: Mycobacterium tuberculosis

<400> SEQUENCE: 28

Ser Arg Leu Ile Gly Ala Leu Thr Val Val Ala Ile Ile Val Thr Ala
1               5                   10                  15

Cys Gly Ser Gln Pro Lys
            20

<210> SEQ ID NO 29
<211> LENGTH: 14
<212> TYPE: PRT
<213> ORGANISM: Mycobacterium tuberculosis

<400> SEQUENCE: 29

Ala Pro Val Val Gly Gln Val Ala Ala Ser His Pro Glu Val
1               5                   10

<210> SEQ ID NO 30
<211> LENGTH: 15
<212> TYPE: PRT
<213> ORGANISM: Mycobacterium tuberculosis

<400> SEQUENCE: 30

Pro Glu Val Thr Phe Val Gly Val Ala Gly Leu Asp Gln Val Pro
1               5                   10                  15

<210> SEQ ID NO 31
<211> LENGTH: 19
<212> TYPE: PRT
<213> ORGANISM: Mycobacterium tuberculosis

<400> SEQUENCE: 31

Gln Glu Phe Val Asn Lys Tyr Pro Val Lys Thr Phe Thr Gln Leu Ala
1               5                   10                  15

Asp Thr Asp

<210> SEQ ID NO 32
<211> LENGTH: 13
<212> TYPE: PRT
<213> ORGANISM: Mycobacterium tuberculosis

<400> SEQUENCE: 32

Ser Val Trp Ala Asn Phe Gly Val Thr Gln Gln Pro Ala
1               5                   10

<210> SEQ ID NO 33
<211> LENGTH: 23
<212> TYPE: PRT
<213> ORGANISM: Mycobacterium tuberculosis

<400> SEQUENCE: 33

Val Asp Val Val Arg Gly Arg Met Ser Gln Asp Glu Leu Thr Arg Arg
1               5                   10                  15

Val Thr Ala Leu Thr Ser Arg
            20

<210> SEQ ID NO 34
<211> LENGTH: 27
<212> TYPE: PRT
<213> ORGANISM: Mycobacterium tuberculosis

<400> SEQUENCE: 34
```

```
Gln Val Tyr Arg Cys Asp Leu Gly Tyr Gly Ala Lys Pro Trp Leu Ile
1               5                   10                  15

Val Ser Asn Asn Ala Arg Asn Arg His Thr Ala
            20                  25
```

<210> SEQ ID NO 35
<211> LENGTH: 17
<212> TYPE: PRT
<213> ORGANISM: Mycobacterium tuberculosis

<400> SEQUENCE: 35

```
Gln Val Tyr Arg Cys Asp Leu Gly Tyr Gly Ala Lys Pro Trp Leu Ile
1               5                   10                  15

Val
```

<210> SEQ ID NO 36
<211> LENGTH: 16
<212> TYPE: PRT
<213> ORGANISM: Mycobacterium tuberculosis

<400> SEQUENCE: 36

```
Lys Pro Trp Leu Ile Val Ser Asn Asn Ala Arg Asn Arg His Thr Ala
1               5                   10                  15
```

<210> SEQ ID NO 37
<211> LENGTH: 16
<212> TYPE: PRT
<213> ORGANISM: Mycobacterium tuberculosis

<400> SEQUENCE: 37

```
Ala Asp Val Val Ala Val Arg Leu Thr Thr Thr Arg Arg Thr Ile Pro
1               5                   10                  15
```

<210> SEQ ID NO 38
<211> LENGTH: 13
<212> TYPE: PRT
<213> ORGANISM: Mycobacterium tuberculosis

<400> SEQUENCE: 38

```
Pro Thr Trp Val Ala Met Gly Pro Ser Asp Pro Leu Thr
1               5                   10
```

<210> SEQ ID NO 39
<211> LENGTH: 14
<212> TYPE: PRT
<213> ORGANISM: Mycobacterium tuberculosis

<400> SEQUENCE: 39

```
Thr Gly Tyr Val Asn Ala Asp Asn Ile Glu Thr Leu Gly Lys
1               5                   10
```

<210> SEQ ID NO 40
<211> LENGTH: 16
<212> TYPE: PRT
<213> ORGANISM: Mycobacterium tuberculosis

<400> SEQUENCE: 40

```
Ala Thr Met Asn Lys Ile Asn Thr Ala Leu Ala Thr Ala Leu Gly Leu
1               5                   10                  15
```

<210> SEQ ID NO 41
<211> LENGTH: 11
<212> TYPE: PRT

<213> ORGANISM: Mycobacterium tuberculosis

<400> SEQUENCE: 41

Ala Asp Thr His Gly Ala Thr Ser Asp Phe Trp
1               5                   10

<210> SEQ ID NO 42
<211> LENGTH: 12
<212> TYPE: PRT
<213> ORGANISM: Mycobacterium tuberculosis

<400> SEQUENCE: 42

Gly Pro Val Ala Ala Gly Leu Gly Arg Ala Ala Leu
1               5                   10

<210> SEQ ID NO 43
<211> LENGTH: 10
<212> TYPE: PRT
<213> ORGANISM: Mycobacterium tuberculosis

<400> SEQUENCE: 43

Val Gly Tyr Leu Ser Val Pro Gln Gly Trp
1               5                   10

<210> SEQ ID NO 44
<211> LENGTH: 14
<212> TYPE: PRT
<213> ORGANISM: Mycobacterium tuberculosis

<400> SEQUENCE: 44

Thr Glu Ala Glu Pro Asn Gln Ala Leu Gly Trp Leu Pro Met
1               5                   10

<210> SEQ ID NO 45
<211> LENGTH: 14
<212> TYPE: PRT
<213> ORGANISM: Mycobacterium tuberculosis

<400> SEQUENCE: 45

Ala Glu Ala Ala Ala Gln Pro Ser His Ala Leu Gly Trp Leu
1               5                   10

<210> SEQ ID NO 46
<211> LENGTH: 12
<212> TYPE: PRT
<213> ORGANISM: Mycobacterium tuberculosis

<400> SEQUENCE: 46

Leu Pro Ile Glu Glu Ile Asp Ala Ala Ala Ser Asp
1               5                   10

<210> SEQ ID NO 47
<211> LENGTH: 16
<212> TYPE: PRT
<213> ORGANISM: Mycobacterium tuberculosis

<400> SEQUENCE: 47

Gly Glu Val Ser Ser Ser Pro Gln Leu Pro Pro Arg Pro Phe Met Met
1               5                   10                  15

<210> SEQ ID NO 48
<211> LENGTH: 12
<212> TYPE: PRT
<213> ORGANISM: Mycobacterium tuberculosis

<400> SEQUENCE: 48

Arg Pro Phe Met Met Pro His Thr Pro Ser Gly Gly
1               5                   10

<210> SEQ ID NO 49
<211> LENGTH: 14
<212> TYPE: PRT
<213> ORGANISM: Mycobacterium tuberculosis

<400> SEQUENCE: 49

Ser Thr Arg Arg Thr Cys Asn His Gly Gly Ile Thr Trp Arg
1               5                   10

<210> SEQ ID NO 50
<211> LENGTH: 14
<212> TYPE: PRT
<213> ORGANISM: Mycobacterium tuberculosis

<400> SEQUENCE: 50

Ile Thr Trp Arg Val Ala Ala Thr Ser Ala Arg Ser Ala Arg
1               5                   10

<210> SEQ ID NO 51
<211> LENGTH: 12
<212> TYPE: PRT
<213> ORGANISM: Mycobacterium tuberculosis

<400> SEQUENCE: 51

Ala Thr Thr His Pro Glu Ala Gly His Tyr Gly Leu
1               5                   10

<210> SEQ ID NO 52
<211> LENGTH: 13
<212> TYPE: PRT
<213> ORGANISM: Mycobacterium tuberculosis

<400> SEQUENCE: 52

Glu Ala Gly His Tyr Gly Leu Ala Thr Trp Phe Thr Arg
1               5                   10

<210> SEQ ID NO 53
<211> LENGTH: 11
<212> TYPE: PRT
<213> ORGANISM: Mycobacterium tuberculosis

<400> SEQUENCE: 53

His Ala Leu Ala Ala Arg Thr Leu Ala Ala Ala
1               5                   10

<210> SEQ ID NO 54
<211> LENGTH: 10
<212> TYPE: PRT
<213> ORGANISM: Mycobacterium tuberculosis

<400> SEQUENCE: 54

Thr Leu Leu Ala Ala Ala Asp Glu Leu Val
1               5                   10

<210> SEQ ID NO 55
<211> LENGTH: 11
<212> TYPE: PRT
<213> ORGANISM: Mycobacterium tuberculosis

<400> SEQUENCE: 55

```
Ala Ala Leu Ala Gly Asp Ala Ala Gly Ala Trp
1               5                   10
```

<210> SEQ ID NO 56
<211> LENGTH: 15
<212> TYPE: PRT
<213> ORGANISM: Mycobacterium tuberculosis

<400> SEQUENCE: 56

```
Arg Thr Ala Ala Val Glu Leu Ala Arg Ala Leu Val Arg Ala Val
1               5                   10                  15
```

<210> SEQ ID NO 57
<211> LENGTH: 13
<212> TYPE: PRT
<213> ORGANISM: Mycobacterium tuberculosis

<400> SEQUENCE: 57

```
Ala Glu Ser His Gly Val Ala Ala Val Leu Phe Ala Ala
1               5                   10
```

<210> SEQ ID NO 58
<211> LENGTH: 14
<212> TYPE: PRT
<213> ORGANISM: Mycobacterium tuberculosis

<400> SEQUENCE: 58

```
Val Leu Phe Ala Ala Thr Ala Ala Ala Ala Val Asp Arg
1               5                   10
```

<210> SEQ ID NO 59
<211> LENGTH: 13
<212> TYPE: PRT
<213> ORGANISM: Mycobacterium tuberculosis

<400> SEQUENCE: 59

```
Arg Arg Thr Asp Pro Gln Leu Ala Ala Phe Tyr His Arg
1               5                   10
```

<210> SEQ ID NO 60
<211> LENGTH: 15
<212> TYPE: PRT
<213> ORGANISM: Mycobacterium tuberculosis

<400> SEQUENCE: 60

```
His Thr Gln Ala Thr Ile Ala Val Ala Arg Lys Leu Ala Glu Arg
1               5                   10                  15
```

<210> SEQ ID NO 61
<211> LENGTH: 15
<212> TYPE: PRT
<213> ORGANISM: Mycobacterium tuberculosis

<400> SEQUENCE: 61

```
Arg Thr Arg Val Thr Ile Thr Thr Gly Arg Pro Tyr Gln Leu Arg
1               5                   10                  15
```

<210> SEQ ID NO 62
<211> LENGTH: 13
<212> TYPE: PRT
<213> ORGANISM: Mycobacterium tuberculosis

<400> SEQUENCE: 62

```
Lys Glu Leu Ile Asp Ala His Tyr His Val Asp Thr Arg
1               5                   10
```

```
<210> SEQ ID NO 63
<211> LENGTH: 12
<212> TYPE: PRT
<213> ORGANISM: Mycobacterium tuberculosis

<400> SEQUENCE: 63

Asp Thr Arg Thr His Pro His Asn Arg Ala His Thr
1               5                   10

<210> SEQ ID NO 64
<211> LENGTH: 14
<212> TYPE: PRT
<213> ORGANISM: Mycobacterium tuberculosis

<400> SEQUENCE: 64

Arg Ala His Thr Asp Thr Met Gln Asn Ser Lys Pro Ala Arg
1               5                   10

<210> SEQ ID NO 65
<211> LENGTH: 15
<212> TYPE: PRT
<213> ORGANISM: Mycobacterium tuberculosis

<400> SEQUENCE: 65

Val Tyr Arg Cys Asp Leu Gly Tyr Gly Ala Lys Pro Trp Leu Ile
1               5                   10                  15

<210> SEQ ID NO 66
<211> LENGTH: 14
<212> TYPE: PRT
<213> ORGANISM: Mycobacterium tuberculosis

<400> SEQUENCE: 66

His Thr Ala Asp Val Val Ala Val Arg Leu Thr Thr Thr Arg
1               5                   10

<210> SEQ ID NO 67
<211> LENGTH: 13
<212> TYPE: PRT
<213> ORGANISM: Mycobacterium tuberculosis

<400> SEQUENCE: 67

Leu Thr Thr Thr Arg Arg Thr Ile Pro Thr Trp Val Ala
1               5                   10

<210> SEQ ID NO 68
<211> LENGTH: 13
<212> TYPE: PRT
<213> ORGANISM: Mycobacterium tuberculosis

<400> SEQUENCE: 68

Tyr Leu Gly Glu Val Thr Pro Ala Thr Met Asn Lys Ile
1               5                   10

<210> SEQ ID NO 69
<211> LENGTH: 10
<212> TYPE: PRT
<213> ORGANISM: Mycobacterium tuberculosis

<400> SEQUENCE: 69

Ala Leu Ala Thr Ala Leu Gly Leu Pro Trp
1               5                   10
```

<210> SEQ ID NO 70
<211> LENGTH: 14
<212> TYPE: PRT
<213> ORGANISM: Mycobacterium tuberculosis

<400> SEQUENCE: 70

Gly Thr Ile Ala Val Pro Gly Gly Arg Val Trp Phe Gln Arg
1               5                   10

<210> SEQ ID NO 71
<211> LENGTH: 11
<212> TYPE: PRT
<213> ORGANISM: Mycobacterium tuberculosis

<400> SEQUENCE: 71

Leu Pro His Asn Tyr Leu Ala Pro Leu Arg Arg
1               5                   10

<210> SEQ ID NO 72
<211> LENGTH: 15
<212> TYPE: PRT
<213> ORGANISM: Mycobacterium tuberculosis

<400> SEQUENCE: 72

Asn Ser Ala Cys Pro Ser Asp Val Asp Leu Trp Thr Met Asn Arg
1               5                   10                  15

<210> SEQ ID NO 73
<211> LENGTH: 14
<212> TYPE: PRT
<213> ORGANISM: Mycobacterium tuberculosis

<400> SEQUENCE: 73

Ala Glu Met Ala Thr Val Ala Glu Ala Leu Ala Leu Thr Arg
1               5                   10

<210> SEQ ID NO 74
<211> LENGTH: 13
<212> TYPE: PRT
<213> ORGANISM: Mycobacterium tuberculosis

<400> SEQUENCE: 74

Ala Glu Ala Leu Ala Leu Thr Arg Phe His Ile Phe Ser
1               5                   10

<210> SEQ ID NO 75
<211> LENGTH: 11
<212> TYPE: PRT
<213> ORGANISM: Mycobacterium tuberculosis

<400> SEQUENCE: 75

Leu Thr Arg Phe His Ile Phe Ser His Ser Trp
1               5                   10

<210> SEQ ID NO 76
<211> LENGTH: 11
<212> TYPE: PRT
<213> ORGANISM: Mycobacterium tuberculosis

<400> SEQUENCE: 76

Gly Met Leu Ala Gln Gln Tyr Val Leu Asp Lys
1               5                   10

<210> SEQ ID NO 77
<211> LENGTH: 15

-continued

```
<212> TYPE: PRT
<213> ORGANISM: Mycobacterium tuberculosis

<400> SEQUENCE: 77

Leu Thr Ile Ala Asn Ser Thr Ala Ser Ile Pro Glu Phe Ser Ala
1               5                   10                  15

<210> SEQ ID NO 78
<211> LENGTH: 12
<212> TYPE: PRT
<213> ORGANISM: Mycobacterium tuberculosis

<400> SEQUENCE: 78

Ile Pro Glu Phe Ser Ala Ser Leu Val Ser Leu Lys
1               5                   10

<210> SEQ ID NO 79
<211> LENGTH: 12
<212> TYPE: PRT
<213> ORGANISM: Mycobacterium tuberculosis

<400> SEQUENCE: 79

His Ser Ala Glu Tyr Gln Ala Ala Ile Arg Thr Trp
1               5                   10

<210> SEQ ID NO 80
<211> LENGTH: 14
<212> TYPE: PRT
<213> ORGANISM: Mycobacterium tuberculosis

<400> SEQUENCE: 80

Arg Thr Trp Asn Glu Thr Tyr Leu Cys Arg Thr Arg Pro Trp
1               5                   10

<210> SEQ ID NO 81
<211> LENGTH: 12
<212> TYPE: PRT
<213> ORGANISM: Mycobacterium tuberculosis

<400> SEQUENCE: 81

Glu Thr Tyr Leu Cys Arg Thr Arg Pro Trp Pro Arg
1               5                   10

<210> SEQ ID NO 82
<211> LENGTH: 14
<212> TYPE: PRT
<213> ORGANISM: Mycobacterium tuberculosis

<400> SEQUENCE: 82

Arg Pro Trp Pro Arg Glu Leu Thr Glu Ala Phe Ala Asn Met
1               5                   10

<210> SEQ ID NO 83
<211> LENGTH: 12
<212> TYPE: PRT
<213> ORGANISM: Mycobacterium tuberculosis

<400> SEQUENCE: 83

Thr Glu Ala Phe Ala Asn Met Gly Thr Glu Ile Phe
1               5                   10

<210> SEQ ID NO 84
<211> LENGTH: 12
<212> TYPE: PRT
<213> ORGANISM: Mycobacterium tuberculosis
```

<400> SEQUENCE: 84

Phe Glu Thr Met Phe Gly Pro Ser Asp Phe Arg Ile
1               5                   10

<210> SEQ ID NO 85
<211> LENGTH: 12
<212> TYPE: PRT
<213> ORGANISM: Mycobacterium tuberculosis

<400> SEQUENCE: 85

Leu Glu Phe Phe Glu Ser Ser Ser His Met Pro Phe
1               5                   10

<210> SEQ ID NO 86
<211> LENGTH: 10
<212> TYPE: PRT
<213> ORGANISM: Mycobacterium tuberculosis

<400> SEQUENCE: 86

Met Pro Phe Ile Glu Glu Pro Ala Arg Phe
1               5                   10

<210> SEQ ID NO 87
<211> LENGTH: 13
<212> TYPE: PRT
<213> ORGANISM: Mycobacterium tuberculosis

<400> SEQUENCE: 87

Asp Arg Val Met Arg Glu Phe Leu Arg Leu His Asp Ile
1               5                   10

<210> SEQ ID NO 88
<211> LENGTH: 12
<212> TYPE: PRT
<213> ORGANISM: Mycobacterium tuberculosis

<400> SEQUENCE: 88

Ala Asn Leu Ala Ala Gly Thr Glu Ala Glu Pro Asn
1               5                   10

<210> SEQ ID NO 89
<211> LENGTH: 20
<212> TYPE: PRT
<213> ORGANISM: Mycobacterium tuberculosis

<400> SEQUENCE: 89

Ala Ala Ala Ser Asp Asp Gly Glu Val Ser Ser Ser Pro Gln Leu Pro
1               5                   10                  15

Pro Arg Pro Phe
            20

<210> SEQ ID NO 90
<211> LENGTH: 13
<212> TYPE: PRT
<213> ORGANISM: Mycobacterium tuberculosis

<400> SEQUENCE: 90

Ala Ala Gly Thr Glu Ala Glu Pro Asn Gln Ala Leu Gly
1               5                   10

<210> SEQ ID NO 91
<211> LENGTH: 15
<212> TYPE: PRT

<213> ORGANISM: Mycobacterium tuberculosis

<400> SEQUENCE: 91

Asp Ile Asp Ala Ala Ala Glu Ala Ala Ala Gln Pro Ser His Ala
1 5 10 15

<210> SEQ ID NO 92
<211> LENGTH: 12
<212> TYPE: PRT
<213> ORGANISM: Mycobacterium tuberculosis

<400> SEQUENCE: 92

Glu Ile Asp Ala Ala Ala Ser Asp Asp Gly Glu Val
1 5 10

<210> SEQ ID NO 93
<211> LENGTH: 10
<212> TYPE: PRT
<213> ORGANISM: Mycobacterium tuberculosis

<400> SEQUENCE: 93

Phe Met Met Pro His Thr Pro Ser Gly Gly
1 5 10

<210> SEQ ID NO 94
<211> LENGTH: 16
<212> TYPE: PRT
<213> ORGANISM: Mycobacterium tuberculosis

<400> SEQUENCE: 94

Gly Glu Val Ser Ser Ser Pro Gln Leu Pro Pro Arg Pro Phe Met Met
1 5 10 15

<210> SEQ ID NO 95
<211> LENGTH: 11
<212> TYPE: PRT
<213> ORGANISM: Mycobacterium tuberculosis

<400> SEQUENCE: 95

Gly Thr Glu Ala Glu Pro Asn Gln Ala Leu Gly
1 5 10

<210> SEQ ID NO 96
<211> LENGTH: 11
<212> TYPE: PRT
<213> ORGANISM: Mycobacterium tuberculosis

<400> SEQUENCE: 96

Gly Trp Thr Glu Ala Asn Gln Ala Asn Leu Ala
1 5 10

<210> SEQ ID NO 97
<211> LENGTH: 15
<212> TYPE: PRT
<213> ORGANISM: Mycobacterium tuberculosis

<400> SEQUENCE: 97

Met Thr Ile Asn Asn Gln Phe Asp Asp Ala Asp Thr His Gly Ala
1 5 10 15

<210> SEQ ID NO 98
<211> LENGTH: 11
<212> TYPE: PRT
<213> ORGANISM: Mycobacterium tuberculosis

```
<400> SEQUENCE: 98

Ser Val Pro Gln Gly Trp Thr Glu Ala Asn Gln
1               5                   10

<210> SEQ ID NO 99
<211> LENGTH: 13
<212> TYPE: PRT
<213> ORGANISM: Mycobacterium tuberculosis

<400> SEQUENCE: 99

Thr Ile Asn Asn Gln Phe Asp Asp Ala Asp Thr His Gly
1               5                   10

<210> SEQ ID NO 100
<211> LENGTH: 11
<212> TYPE: PRT
<213> ORGANISM: Mycobacterium tuberculosis

<400> SEQUENCE: 100

Trp Leu Pro Met Gln Asp Ile Asp Ala Ala Ala
1               5                   10

<210> SEQ ID NO 101
<211> LENGTH: 11
<212> TYPE: PRT
<213> ORGANISM: Mycobacterium tuberculosis

<400> SEQUENCE: 101

Lys Ser Thr Arg Arg Thr Cys Asn His Gly Gly
1               5                   10

<210> SEQ ID NO 102
<211> LENGTH: 13
<212> TYPE: PRT
<213> ORGANISM: Mycobacterium tuberculosis

<400> SEQUENCE: 102

Val Ala Ala Thr Ser Ala Arg Ser Ala Arg Ser Leu Ala
1               5                   10

<210> SEQ ID NO 103
<211> LENGTH: 12
<212> TYPE: PRT
<213> ORGANISM: Mycobacterium tuberculosis

<400> SEQUENCE: 103

Met Ile Asp Asp Arg His Lys Ser Thr Arg Arg Thr
1               5                   10

<210> SEQ ID NO 104
<211> LENGTH: 13
<212> TYPE: PRT
<213> ORGANISM: Mycobacterium tuberculosis

<400> SEQUENCE: 104

Ala Ala Leu Ala Gly Asp Ala Ala Gly Ala Trp Arg Thr
1               5                   10

<210> SEQ ID NO 105
<211> LENGTH: 10
<212> TYPE: PRT
<213> ORGANISM: Mycobacterium tuberculosis

<400> SEQUENCE: 105
```

Ala Gly Arg Arg Thr Asp Pro Gln Leu Ala
1               5                   10

<210> SEQ ID NO 106
<211> LENGTH: 22
<212> TYPE: PRT
<213> ORGANISM: Mycobacterium tuberculosis

<400> SEQUENCE: 106

Asp Thr Arg Thr His Pro His Asn Arg Ala His Thr Asp Thr Met Gln
1               5                   10                  15

Asn Ser Lys Pro Ala Arg
            20

<210> SEQ ID NO 107
<211> LENGTH: 11
<212> TYPE: PRT
<213> ORGANISM: Mycobacterium tuberculosis

<400> SEQUENCE: 107

Gly Asp Pro Val Thr Ala Arg Gly Ala Lys Glu
1               5                   10

<210> SEQ ID NO 108
<211> LENGTH: 13
<212> TYPE: PRT
<213> ORGANISM: Mycobacterium tuberculosis

<400> SEQUENCE: 108

Pro Leu Ala Gly Arg Arg Thr Asp Pro Gln Leu Ala Ala
1               5                   10

<210> SEQ ID NO 109
<211> LENGTH: 12
<212> TYPE: PRT
<213> ORGANISM: Mycobacterium tuberculosis

<400> SEQUENCE: 109

Arg Asp Thr Asn Gly Asp Pro Val Thr Ala Arg Gly
1               5                   10

<210> SEQ ID NO 110
<211> LENGTH: 13
<212> TYPE: PRT
<213> ORGANISM: Mycobacterium tuberculosis

<400> SEQUENCE: 110

Arg Val Val Thr Asp Arg Asp Ser Gly Ala Gly Ala Leu
1               5                   10

<210> SEQ ID NO 111
<211> LENGTH: 17
<212> TYPE: PRT
<213> ORGANISM: Mycobacterium tuberculosis

<400> SEQUENCE: 111

Thr Thr Gly Arg Pro Tyr Gln Leu Arg Asp Thr Asn Gly Asp Pro Val
1               5                   10                  15

Thr

<210> SEQ ID NO 112
<211> LENGTH: 13
<212> TYPE: PRT
<213> ORGANISM: Mycobacterium tuberculosis

<400> SEQUENCE: 112

Val Ala Arg Lys Leu Ala Glu Arg Thr Arg Val Thr Ile
1               5                   10

<210> SEQ ID NO 113
<211> LENGTH: 16
<212> TYPE: PRT
<213> ORGANISM: Mycobacterium tuberculosis

<400> SEQUENCE: 113

Ala Met Gly Pro Ser Asp Pro Leu Thr Gly Tyr Val Asn Ala Asp Asn
1               5                   10                  15

<210> SEQ ID NO 114
<211> LENGTH: 13
<212> TYPE: PRT
<213> ORGANISM: Mycobacterium tuberculosis

<400> SEQUENCE: 114

Cys Asp Leu Gly Tyr Gly Ala Lys Pro Trp Leu Ile Val
1               5                   10

<210> SEQ ID NO 115
<211> LENGTH: 11
<212> TYPE: PRT
<213> ORGANISM: Mycobacterium tuberculosis

<400> SEQUENCE: 115

Met Asn Ala Pro Leu Arg Gly Gln Val Tyr Arg
1               5                   10

<210> SEQ ID NO 116
<211> LENGTH: 11
<212> TYPE: PRT
<213> ORGANISM: Mycobacterium tuberculosis

<400> SEQUENCE: 116

Ser Asn Asn Ala Arg Asn Arg His Thr Ala Asp
1               5                   10

<210> SEQ ID NO 117
<211> LENGTH: 25
<212> TYPE: PRT
<213> ORGANISM: Mycobacterium tuberculosis

<400> SEQUENCE: 117

Leu Arg Gly Gln Val Tyr Gly Gly Glu Val Thr Pro Ala Thr Met Asn
1               5                   10                  15

Lys Ile Asn Gly Gly Val Ser Asn Asn
            20                  25

<210> SEQ ID NO 118
<211> LENGTH: 17
<212> TYPE: PRT
<213> ORGANISM: Mycobacterium tuberculosis

<400> SEQUENCE: 118

Leu Gly Tyr Arg Cys Asp Leu Gly Tyr Gly Ala Lys Gly Arg Leu Thr
1               5                   10                  15

Thr

<210> SEQ ID NO 119

```
<211> LENGTH: 20
<212> TYPE: PRT
<213> ORGANISM: Mycobacterium tuberculosis

<400> SEQUENCE: 119

Thr Thr Thr Arg Arg Thr Ile Pro Thr Trp Val Ala Met Gly Pro Ser
1               5                   10                  15

Asp Pro Leu Thr
            20

<210> SEQ ID NO 120
<211> LENGTH: 18
<212> TYPE: PRT
<213> ORGANISM: Mycobacterium tuberculosis

<400> SEQUENCE: 120

Tyr Arg Cys Asp Gly Gly Gly Asp Gly Thr Leu Gly Lys Asp Glu Leu
1               5                   10                  15

Gly Asp

<210> SEQ ID NO 121
<211> LENGTH: 22
<212> TYPE: PRT
<213> ORGANISM: Mycobacterium tuberculosis

<400> SEQUENCE: 121

Met Glu Gly Thr Ile Ala Val Pro Gly Gly Arg Val Trp Phe Gln Arg
1               5                   10                  15

Gly Gly Gly Asn Ser Ala
            20

<210> SEQ ID NO 122
<211> LENGTH: 17
<212> TYPE: PRT
<213> ORGANISM: Mycobacterium tuberculosis

<400> SEQUENCE: 122

Met Gln Arg Ile Gly Gly Pro Gly Arg Gly Gly Arg Arg Leu Ser Asp
1               5                   10                  15

Glu

<210> SEQ ID NO 123
<211> LENGTH: 26
<212> TYPE: PRT
<213> ORGANISM: Mycobacterium tuberculosis

<400> SEQUENCE: 123

Val Ser Leu Lys Ser Cys Leu Asp Val Ala Thr Arg Ser Ala Ile Asp
1               5                   10                  15

Arg Pro Glu Tyr Gln Ala Ala Ile Arg Thr
            20                  25

<210> SEQ ID NO 124
<211> LENGTH: 16
<212> TYPE: PRT
<213> ORGANISM: Mycobacterium tuberculosis

<400> SEQUENCE: 124

Glu Thr Tyr Leu Cys Arg Thr Arg Pro Trp Pro Arg Glu Leu Thr Glu
1               5                   10                  15

<210> SEQ ID NO 125
```

```
<211> LENGTH: 22
<212> TYPE: PRT
<213> ORGANISM: Mycobacterium tuberculosis

<400> SEQUENCE: 125

Met Glu Gly Thr Ile Ala Val Pro Gly Gly Arg Val Trp Phe Gln Arg
1               5                   10                  15

Gly Gly Gly Asn Ser Ala
            20

<210> SEQ ID NO 126
<211> LENGTH: 17
<212> TYPE: PRT
<213> ORGANISM: Mycobacterium tuberculosis

<400> SEQUENCE: 126

Met Gln Arg Ile Gly Gly Pro Gly Arg Gly Gly Arg Arg Leu Ser Asp
1               5                   10                  15

Glu

<210> SEQ ID NO 127
<211> LENGTH: 26
<212> TYPE: PRT
<213> ORGANISM: Mycobacterium tuberculosis

<400> SEQUENCE: 127

Val Ser Leu Lys Ser Cys Leu Asp Val Ala Thr Arg Ser Ala Ile Asp
1               5                   10                  15

Arg Pro Glu Tyr Gln Ala Ala Ile Arg Thr
            20                  25

<210> SEQ ID NO 128
<211> LENGTH: 16
<212> TYPE: PRT
<213> ORGANISM: Mycobacterium tuberculosis

<400> SEQUENCE: 128

Glu Thr Tyr Leu Cys Arg Thr Arg Pro Trp Pro Arg Glu Leu Thr Glu
1               5                   10                  15

<210> SEQ ID NO 129
<211> LENGTH: 12
<212> TYPE: PRT
<213> ORGANISM: Mycobacterium tuberculosis

<400> SEQUENCE: 129

Asp Val Ala Thr Arg Ser Ala Ile Asp Arg His Glu
1               5                   10

<210> SEQ ID NO 130
<211> LENGTH: 11
<212> TYPE: PRT
<213> ORGANISM: Mycobacterium tuberculosis

<400> SEQUENCE: 130

Gly Asn Val Arg Asp Trp Asp Val Val Asp Arg
1               5                   10

<210> SEQ ID NO 131
<211> LENGTH: 16
<212> TYPE: PRT
<213> ORGANISM: Mycobacterium tuberculosis

<400> SEQUENCE: 131
```

```
Gly Arg Val Trp Phe Gln Arg Ile Gly Gly Pro Gly Arg Pro Leu
1               5                   10                  15

<210> SEQ ID NO 132
<211> LENGTH: 12
<212> TYPE: PRT
<213> ORGANISM: Mycobacterium tuberculosis

<400> SEQUENCE: 132

His Met Arg Glu Met Gln Gly Arg Ile Ala Gly Ser
1               5                   10

<210> SEQ ID NO 133
<211> LENGTH: 12
<212> TYPE: PRT
<213> ORGANISM: Mycobacterium tuberculosis

<400> SEQUENCE: 133

Met Arg Glu Met Gln Gly Arg Ile Ala Gly Ser Arg
1               5                   10

<210> SEQ ID NO 134
<211> LENGTH: 12
<212> TYPE: PRT
<213> ORGANISM: Mycobacterium tuberculosis

<400> SEQUENCE: 134

Gln Leu Gly Cys Gly Asn Ser Ala Cys Pro Ser Asp
1               5                   10

<210> SEQ ID NO 135
<211> LENGTH: 13
<212> TYPE: PRT
<213> ORGANISM: Mycobacterium tuberculosis

<400> SEQUENCE: 135

Gln Gln Tyr Val Leu Asp Lys Ala Pro Asp Ala Val Ser
1               5                   10

<210> SEQ ID NO 136
<211> LENGTH: 11
<212> TYPE: PRT
<213> ORGANISM: Mycobacterium tuberculosis

<400> SEQUENCE: 136

Arg Glu Met Gln Gly Arg Ile Ala Gly Ser Arg
1               5                   10

<210> SEQ ID NO 137
<211> LENGTH: 16
<212> TYPE: PRT
<213> ORGANISM: Mycobacterium tuberculosis

<400> SEQUENCE: 137

Thr Ala Cys Gly Ser Gln Pro Lys Ser Gln Pro Ala Val Ala Pro Thr
1               5                   10                  15

<210> SEQ ID NO 138
<211> LENGTH: 18
<212> TYPE: PRT
<213> ORGANISM: Mycobacterium tuberculosis

<400> SEQUENCE: 138

Thr Gln Val Pro Ala Gly Gln Thr Val Pro Ala Gln Leu Gln Phe Ser
```

Ala Lys

<210> SEQ ID NO 139
<211> LENGTH: 14
<212> TYPE: PRT
<213> ORGANISM: Mycobacterium tuberculosis

<400> SEQUENCE: 139

Ser Ala Lys Thr Leu Asp Gly His Asp Phe His Gly Glu Ser
1               5                   10

<210> SEQ ID NO 140
<211> LENGTH: 15
<212> TYPE: PRT
<213> ORGANISM: Mycobacterium tuberculosis

<400> SEQUENCE: 140

Met Gln Glu Phe Val Asn Lys Tyr Pro Val Lys Thr Phe Thr Gln
1               5                   10                  15

<210> SEQ ID NO 141
<211> LENGTH: 21
<212> TYPE: PRT
<213> ORGANISM: Mycobacterium tuberculosis

<400> SEQUENCE: 141

Asn Phe Gly Val Thr Gln Gln Pro Ala Tyr Ala Phe Val Asp Pro His
1               5                   10                  15

Gly Asn Val Asp Val
            20

<210> SEQ ID NO 142
<211> LENGTH: 8
<212> TYPE: PRT
<213> ORGANISM: Mycobacterium tuberculosis

<400> SEQUENCE: 142

His Gly Ala Thr Ser Asp Phe Trp
1               5

<210> SEQ ID NO 143
<211> LENGTH: 11
<212> TYPE: PRT
<213> ORGANISM: Mycobacterium tuberculosis

<400> SEQUENCE: 143

Glu Pro Asn Gln Ala Leu Gly Trp Leu Pro Met
1               5                   10

<210> SEQ ID NO 144
<211> LENGTH: 13
<212> TYPE: PRT
<213> ORGANISM: Mycobacterium tuberculosis

<400> SEQUENCE: 144

Ser Ser Ser Pro Gln Leu Pro Pro Arg Pro Phe Met Met
1               5                   10

<210> SEQ ID NO 145
<211> LENGTH: 10
<212> TYPE: PRT
<213> ORGANISM: Mycobacterium tuberculosis

```
<400> SEQUENCE: 145

Phe Met Met Pro His Thr Pro Ser Gly Gly
1               5                   10

<210> SEQ ID NO 146
<211> LENGTH: 10
<212> TYPE: PRT
<213> ORGANISM: Mycobacterium tuberculosis

<400> SEQUENCE: 146

His Tyr Gly Leu Ala Thr Trp Phe Thr Arg
1               5                   10

<210> SEQ ID NO 147
<211> LENGTH: 10
<212> TYPE: PRT
<213> ORGANISM: Mycobacterium tuberculosis

<400> SEQUENCE: 147

Glu Leu Ala Arg Ala Leu Val Arg Ala Val
1               5                   10

<210> SEQ ID NO 148
<211> LENGTH: 10
<212> TYPE: PRT
<213> ORGANISM: Mycobacterium tuberculosis

<400> SEQUENCE: 148

Ala Thr Ala Ala Ala Ala Ala Val Asp Arg
1               5                   10

<210> SEQ ID NO 149
<211> LENGTH: 9
<212> TYPE: PRT
<213> ORGANISM: Mycobacterium tuberculosis

<400> SEQUENCE: 149

Gln Leu Ala Ala Phe Tyr His Arg Leu
1               5

<210> SEQ ID NO 150
<211> LENGTH: 12
<212> TYPE: PRT
<213> ORGANISM: Mycobacterium tuberculosis

<400> SEQUENCE: 150

Ala Thr Ile Ala Val Ala Arg Lys Leu Ala Glu Arg
1               5                   10

<210> SEQ ID NO 151
<211> LENGTH: 11
<212> TYPE: PRT
<213> ORGANISM: Mycobacterium tuberculosis

<400> SEQUENCE: 151

Thr Ile Thr Thr Gly Arg Pro Tyr Gln Leu Arg
1               5                   10

<210> SEQ ID NO 152
<211> LENGTH: 9
<212> TYPE: PRT
<213> ORGANISM: Mycobacterium tuberculosis

<400> SEQUENCE: 152
```

```
Thr Met Gln Asn Ser Lys Pro Ala Arg
1               5
```

<210> SEQ ID NO 153
<211> LENGTH: 11
<212> TYPE: PRT
<213> ORGANISM: Mycobacterium tuberculosis

<400> SEQUENCE: 153

```
Asp Leu Gly Tyr Gly Ala Lys Pro Trp Leu Ile
1               5                   10
```

<210> SEQ ID NO 154
<211> LENGTH: 8
<212> TYPE: PRT
<213> ORGANISM: Mycobacterium tuberculosis

<400> SEQUENCE: 154

```
Gly Gly Arg Val Trp Phe Gln Arg
1               5
```

<210> SEQ ID NO 155
<211> LENGTH: 9
<212> TYPE: PRT
<213> ORGANISM: Mycobacterium tuberculosis

<400> SEQUENCE: 155

```
Asp Val Asp Leu Trp Thr Met Asn Arg
1               5
```

<210> SEQ ID NO 156
<211> LENGTH: 10
<212> TYPE: PRT
<213> ORGANISM: Mycobacterium tuberculosis

<400> SEQUENCE: 156

```
Thr Val Ala Glu Ala Leu Ala Leu Thr Arg
1               5                   10
```

<210> SEQ ID NO 157
<211> LENGTH: 10
<212> TYPE: PRT
<213> ORGANISM: Mycobacterium tuberculosis

<400> SEQUENCE: 157

```
Ser Thr Ala Ser Ile Pro Glu Phe Ser Ala
1               5                   10
```

<210> SEQ ID NO 158
<211> LENGTH: 10
<212> TYPE: PRT
<213> ORGANISM: Mycobacterium tuberculosis

<400> SEQUENCE: 158

```
Asp Thr His Gly Ala Thr Ser Asp Phe Trp
1               5                   10
```

<210> SEQ ID NO 159
<211> LENGTH: 14
<212> TYPE: PRT
<213> ORGANISM: Mycobacterium tuberculosis

<400> SEQUENCE: 159

```
Gly Glu Val Ser Ser Ser Pro Gln Leu Pro Pro Arg Pro Phe
1               5                   10
```

```
<210> SEQ ID NO 160
<211> LENGTH: 11
<212> TYPE: PRT
<213> ORGANISM: Mycobacterium tuberculosis

<400> SEQUENCE: 160

Arg Pro Phe Met Met Pro His Thr Pro Ser Gly
1               5                   10

<210> SEQ ID NO 161
<211> LENGTH: 11
<212> TYPE: PRT
<213> ORGANISM: Mycobacterium tuberculosis

<400> SEQUENCE: 161

Glu Ala Gly His Tyr Gly Leu Ala Thr Trp Phe
1               5                   10

<210> SEQ ID NO 162
<211> LENGTH: 12
<212> TYPE: PRT
<213> ORGANISM: Mycobacterium tuberculosis

<400> SEQUENCE: 162

Arg Thr Ala Ala Val Glu Leu Ala Arg Ala Leu Val
1               5                   10

<210> SEQ ID NO 163
<211> LENGTH: 12
<212> TYPE: PRT
<213> ORGANISM: Mycobacterium tuberculosis

<400> SEQUENCE: 163

Val Leu Phe Ala Ala Thr Ala Ala Ala Ala Ala Val
1               5                   10

<210> SEQ ID NO 164
<211> LENGTH: 11
<212> TYPE: PRT
<213> ORGANISM: Mycobacterium tuberculosis

<400> SEQUENCE: 164

His Thr Gln Ala Thr Ile Ala Val Ala Arg Lys
1               5                   10

<210> SEQ ID NO 165
<211> LENGTH: 12
<212> TYPE: PRT
<213> ORGANISM: Mycobacterium tuberculosis

<400> SEQUENCE: 165

Arg Thr Arg Val Thr Ile Thr Thr Gly Arg Pro Tyr
1               5                   10

<210> SEQ ID NO 166
<211> LENGTH: 11
<212> TYPE: PRT
<213> ORGANISM: Mycobacterium tuberculosis

<400> SEQUENCE: 166

Arg Ala His Thr Asp Thr Met Gln Asn Ser Lys
1               5                   10
```

```
<210> SEQ ID NO 167
<211> LENGTH: 13
<212> TYPE: PRT
<213> ORGANISM: Mycobacterium tuberculosis

<400> SEQUENCE: 167

Val Tyr Arg Cys Asp Leu Gly Tyr Gly Ala Lys Pro Trp
1               5                   10

<210> SEQ ID NO 168
<211> LENGTH: 12
<212> TYPE: PRT
<213> ORGANISM: Mycobacterium tuberculosis

<400> SEQUENCE: 168

Ala Glu Met Ala Thr Val Ala Glu Ala Leu Ala Leu
1               5                   10

<210> SEQ ID NO 169
<211> LENGTH: 13
<212> TYPE: PRT
<213> ORGANISM: Mycobacterium tuberculosis

<400> SEQUENCE: 169

Leu Thr Ile Ala Asn Ser Thr Ala Ser Ile Pro Glu Phe
1               5                   10

<210> SEQ ID NO 170
<211> LENGTH: 13
<212> TYPE: PRT
<213> ORGANISM: Mycobacterium tuberculosis

<400> SEQUENCE: 170

Asn Ser Ala Cys Pro Ser Asp Val Asp Leu Trp Thr Met
1               5                   10

<210> SEQ ID NO 171
<211> LENGTH: 13
<212> TYPE: PRT
<213> ORGANISM: Mycobacterium tuberculosis

<400> SEQUENCE: 171

Arg Pro Trp Pro Arg Glu Leu Thr Glu Ala Phe Ala Asn
1               5                   10
```

MYCOBACTERIUM TUBERCULOSIS PROTEINS

CROSS REFERENCE TO RELATED APPLICATIONS

This patent application is a National Stage Entry of International Patent Application No. PCT/GB2015/052362, filed on Aug. 14, 2015 which claims the benefit of priority of Bulgarian patent application No. 112045, filed Jun. 30, 2015, and Bulgarian patent application No. 111804, filed Aug. 15, 2014, the contents of each of which are hereby incorporated by reference in their entirety for all purposes herein.

SEQUENCE LISTING

The instant application contains a Sequence Listing which has been submitted electronically in ASCII format and is hereby incorporated by reference in its entirety. Said ASCII copy, created on Jan. 31, 2017, is named 2011324-0032_SL.txt and is 42,748 bytes in size.

FIELD OF THE INVENTION

The present invention relates to *Mycobacterium tuberculosis* (*M. tuberculosis*) proteins and immunologically active fragments (peptides or mimotope peptides) thereof. In particular, the invention relates to a group of *M. tuberculosis* proteins and peptides thereof that are both highly antigenic and characteristic of clinical strains of *M. tuberculosis*. Accordingly, the further relates to the use of these *M. tuberculosis* proteins or peptides in diagnosing, treating or preventing *M. tuberculosis* complex infection.

BACKGROUND

Tuberculosis is a prevalent infectious disease caused by members of the *Mycobacterium tuberculosis* (*M. tuberculosis*) complex. Most *M. tuberculosis* complex infections are asymptomatic, or latent. However, around one in ten latent infections eventually progresses to active disease (usually pulmonary tuberculosis) which, if left untreated, is fatal in over 50% individuals.

Efficient laboratory diagnosis of *M. tuberculosis* complex infection is a key aspect in controlling the spread of tuberculosis. Moreover, rapid and reliable diagnosis allows the correct treatment regimen to be implemented in a timely fashion.

Traditionally, *M. tuberculosis* complex infection has been diagnosed by demonstrating mycobacteria in body fluids using microscopic examination (using the Acid Fast Bacilli (AFB) stain) or microbiological culture. However, samples must contain a high concentration of mycobacteria (i.e. from 5 to 10000/ml) in order for microscopic examination to be reliable, and culture-based diagnosis is slow.

Newer methods of diagnosing *M. tuberculosis* complex infection involve detecting an immune response associated with the infection. Like other mycobacteria, *M. tuberculosis* stimulates CD4+ and CD8+ T-cells, as well other immune cells, to elicit a strong type-1 proinflammatory-like response involving the secretion of cytokines such as interferon (IFN)-gamma and Tumor Necrosis Factor (TNF)-alpha. IFN-gamma release assays (IGRAs) can be used to detect this delayed-type hypersensitivity (DTH) response. IGRAs are based on the principle that T-cells of sensitized (infected) individuals produce IFN-gamma when they re-encounter *M. tuberculosis* antigens. Commercially available IGRAs for *M. tuberculosis* include the original QuantiFERON-TB, and its enhanced versions QuantiFERON-TB Gold and QuantiFERON-TB Gold In-Tube assays (Cellestis International, Carnegie, Australia), the enzyme-linked immunospot (ELISPOT) T SPOT-TB assay (Oxford Immunotec, Oxford, United Kingdom), and various veterinary specialties (Bovigam®, Cervigam®, Primagam®, Prionics, Schlieren-Zurich, Switzerland).

A significant advantage of these IGRAs is their increased specificity for *M. tuberculosis* complex infection. This is achieved by to their use of specific *M. tuberculosis* antigens that are encoded in region of difference (RD)1, a genomic segment that is absent from the Bacille Calmette-Guérin (BCG) vaccine and most environmental mycobacteria. RIM antigens used in IGRAs include ESAT6 and CFP10. While diagnosis based on the immune response to such antigens is effective, there is an ongoing need to develop new, alternative antigens for use in diagnostic tests. For instance, it is important that the antigens used in diagnostic tests are different to those used in vaccines in order to avoid false positive results being obtained for vaccinated subjects. ESAT6 in particular has potential for inclusion in *M. tuberculosis* vaccines. Of course, effective new antigens may also be used in vaccines for preventing or treating *M. tuberculosis* complex infection.

SUMMARY OF THE INVENTION

The inventors have surprisingly identified a number of *M. tuberculosis* antigens and fragments thereof that are particularly useful in diagnostic tests for *M. tuberculosis*. The identified antigens contain a number of T-cell and/or B-cell epitopes that associate effectively with human leukocyte antigen (HLA) molecules or antibodies respectively. The antigens and fragments can therefore be used to detect an anti-*M. tuberculosis* immune response, and thus to determine the presence or absence of *M. tuberculosis* complex infection in an individual. The antigens and fragments are also capable of inducing an immune response in an individual, so may be used for prophylactic or therapeutic vaccination.

Accordingly, the invention provides a method for diagnosing *M. tuberculosis* complex infection in a subject, comprising detecting in vitro an immune response to one or more of (a) Rv0840c (SEQ ID NO: 6) or one or more fragments thereof; (b) TBFG_13463 (SEQ ID NO: 1) or one or more fragments thereof; (c) Rv1677 (SEQ ID NO: 7) or one or more fragments thereof; (d) Rv2654c (SEQ ID NO: 3) or one or more fragments thereof; (e) Rv3845 (SEQ ID NO: 4) or one or more fragments thereof; (f) Rv1495 (SEQ ID NO: 5) or one or more fragments thereof; and (g) Mtub2_17866 (SEQ ID NO: 2) or one or more fragments thereof.

The invention also provides:
- a kit for diagnosing *M. tuberculosis* complex infection in a subject, comprising one or more of the fragments of the invention;
- a composition comprising one or more of (a) to (g) as defined above, for use in treating or preventing *M. tuberculosis* complex infection in a subject; and
- a method of treating or preventing *M. tuberculosis* complex infection in a subject, comprising administering to the subject one or more of (a) to (g) as defined above.

DESCRIPTION OF THE FIGURES

FIG. 2A shows a comparison of Panel A, Panel B and Panel A/Panel B Max in the T-SPOT assay, n=183 (87 TB Positive, 96 Healthy Donors).

FIG. 2B shows Sensitivity and specificity of Panel A/Panel B Max in the T-SPOT.TB assay, calculated by ROC analysis. n=183 (87 TB Positive, 96 Healthy Donors)

FIG. 9 shows a comparison of the ROC curves for Panel A/Panel B max and Panel A/Panel B/Rv0840c peptide library max.

DESCRIPTION OF THE SEQUENCE LISTING

Figure 1:
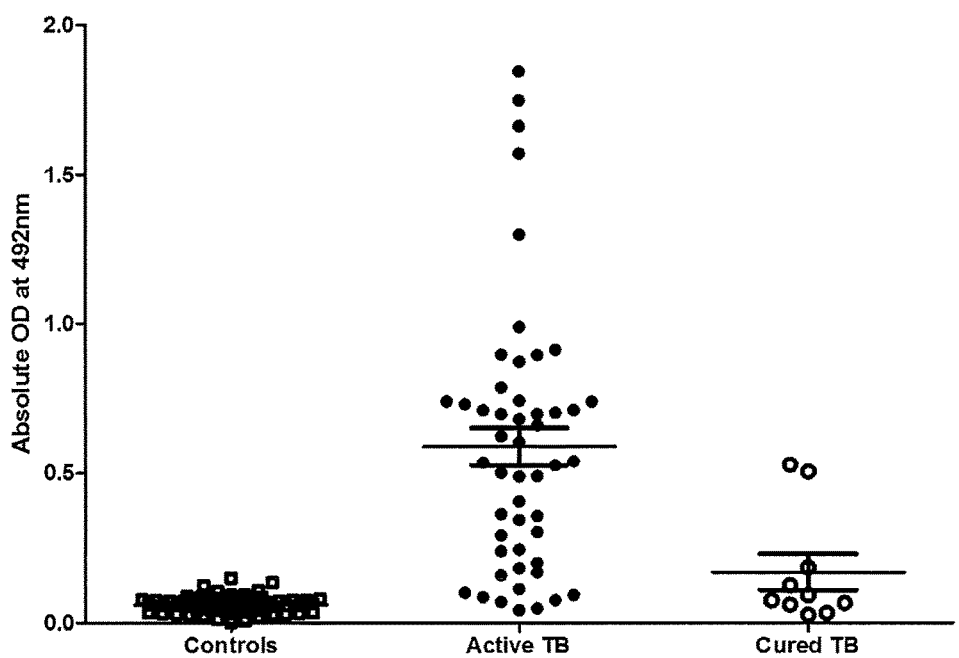
FIG. 1 shows the reactivity of various group sera (Controls, Active TB and cured TB) to a selected pool of B-cell epitopes from the proteins of the invention.

SEQ ID NO: 1 is the amino acid sequence of TBFG_13463.
SEQ ID NO: 2 is the amino acid sequence of Mtub2_17866.
SEQ ID NO: 3 is the amino acid sequence of Rv2654c.
SEQ ID NO: 4 is the amino acid sequence of Rv3845.
SEQ ID NO: 5 is the amino acid sequence of Rv1495.
SEQ ID NO: 6 is the amino acid sequence of Rv0840c.
SEQ ID NO: 7 is the amino acid sequence of Rv1677.
SEQ ID NOs: 8 to 10 are amino acid sequences of HLA class II epitopes derived from TBFG_13463.
SEQ ID NOs: 11 and 12 are amino acid sequences of HLA class II epitopes derived from Mtub2_17866.
SEQ ID NOs: 13 to 19 are amino acid sequences of HLA class II epitopes derived from Rv0840c.
SEQ ID NOs: 20 to 24 are amino acid sequences of HLA class II epitopes derived from Rv3845.
SEQ ID NOs: 25 to 27 are amino acid sequences of HLA class II epitopes derived from Rv2654c.
SEQ ID NOs: 28 to 33 are amino acid sequences of HLA class II epitopes derived from Rv1677.
SEQ ID NOs: 34 to 40 are amino acid sequences of HLA class II epitopes derived from Rv1495.
SEQ ID NOs: 41 to 48 are amino acid sequences of HLA class I epitopes derived from TBFG_13463.
SEQ ID NOs: 49 to 52 are amino acid sequences of HLA class I epitopes derived from Mtub2_17866.
SEQ ID NOs: 53 to 58 are amino acid sequences of HLA class I epitopes derived from Rv2654c.
SEQ ID NOs: 59 to 64 are amino acid sequences of HLA class I epitopes derived from Rv3845.
SEQ ID NOs: 65 to 69 are amino acid sequences of HLA class I epitopes derived from Rv1495.
SEQ ID NOs: 70 to 87 are amino acid sequences of HLA class I epitopes derived from Rv0840c.

SEQ ID NOs: 88 to 100 are amino acid sequences of B-cell epitopes derived from TBFG_13463.
SEQ ID NOs: 101 to 103 are amino acid sequences of B-cell epitopes derived from Mtub2_17866.
SEQ ID NO: 104 is amino acid sequences of B-cell epitopes derived from Rv2654c.
SEQ ID NOs: 105 to 112 are amino acid sequences of B-cell epitopes derived from Rv3845.
SEQ ID NOs: 113 to 120 are amino acid sequences of B-cell epitopes derived from Rv1495.
SEQ ID NOs: 121 to 136 are amino acid sequences of B-cell epitopes derived from Rv0840c.
SEQ ID NOs: 137 to 141 are amino acid sequences of B-cell epitopes derived from Rv1677.
SEQ ID NOs: 142 to 145 are further T cell epitopes derived from TBFG_13463.
SEQ ID NO: 146 is a further T-cell epitope derived from Mtub2_17866.
SEQ ID NOs: 147 and 148 are further T-cell epitopes derived from Rv2654c.
SEQ ID NOs: 149 to 152 are further T-cell epitopes derived from Rv3845.
SEQ ID NO: 153 is a further T-cell epitope derived from Rv1495.
SEQ ID NOs: 154 to 157 are further T-cell epitopes derived from Rv0840c.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition, as used in this specification and the appended claims, the singular forms "a", "an", and "the" include plural referents unless the content clearly dictates otherwise. Thus, for example, reference to "a fragment" includes "fragments", reference to "a cell" includes two or more such cells, reference to "a subject" includes two or more such subjects, and the like.

All publications, patents and patent applications cited herein, whether supra or infra, are hereby incorporated by reference in their entirety.

Methods of the Invention

The present inventors have identified *M. tuberculosis* antigens and fragments thereof that are capable of triggering an immune response to *M. tuberculosis*. Accordingly, these antigens may be used in methods of diagnosing *M. tuberculosis* complex infection in a subject. The antigens may also be used to treat or prevent *M. tuberculosis* complex infection (*M. tuberculosis* complex infection), for example by vaccination. The *M. tuberculosis* complex includes one or more of *Mycobacterium tuberculosis, Mycobacterium africanum, Mycobacterium bovis* (including the *Bacillus* Calmette-Guérin strain), *Mycobacterium microti, Mycobacterium canettii, Mycobacterium caprae, Mycobacterium pinnipedii, Mycobacterium suricattae* and *Mycobacterium mungi*, amongst others. The *M. tuberculosis* complex preferably includes *Mycobacterium tuberculosis*.

The present invention provides a method for diagnosing *Mycobacterium tuberculosis* (*M. tuberculosis*) complex infection in a subject, comprising detecting in vitro an immune response to one or more of ((a) Rv0840c (SEQ ID NO: 6) or one or more fragments thereof; (b) TBFG_13463 (SEQ ID NO: 1) or one or more fragments thereof; (c) Rv1677 (SEQ ID NO: 7) or one or more fragments thereof; (d) Rv2654c (SEQ ID NO: 3) or one or more fragments thereof; (e) Rv3845 (SEQ ID NO: 4) or one or more fragments thereof; (f) Rv1495 (SEQ ID NO: 5) or one or more fragments thereof; and (g) Mtub2_17866 (SEQ ID NO: 2) or one or more fragments thereof. For instance, the method may comprise detecting in vitro an immune response to at least one, at least two, at least three, at least four, at least 5 or at least six of (a) to (g). The method may comprise detecting in vitro an immune response to all of (a) to (g).

In the definition of (a) to (g) given above, an immune response to any combination of one or more of (a) to (g) may be detected in vitro. For instance, for each definition of (a) to (g), an immune response may be detected in vitro to: (a); (b); (c); (d); (e); (f); (g); (a) and (b); (a) and (c); (a) and (d); (a) and (e); (a) and (f); (a) and (g); (b) and (c); (b) and (d); (b) and (e); (b) and (f); (b) and (g); (c) and (d); (c) and (e); (c) and (f); (c) and (g); (d) and (e); (d) and (f); (d) and (g); (e) and (f); (e) and (g); (f) and (g); (a), (b) and (c); (a), (b) and (d); (a), (b) and (e); (a), (b) and (f); (a), (b) and (g); (a,), (c) and (d); (a), (c) and (e); (a), (c) and (f); (a), (c) and (g); (a), (d) and (e); (a), (d) and (f); (a), (d) and (g); (a), (e) and (f); (a), (e) and (g); (a), (f) and (g); (b), (c) and (d); (b), (c) and (e); (b), (c) and (f); (b), (c) and (g); (b), (d) and (e); (b), (d) and (f); (b), (d) and (g); (b), (e) and (f); (b), (e) and (g); (b), (f) and (g); (c), (d) and (e); (c), (d) and (f); (c), (d) and (g); (c), (e) and (f); (c), (e) and (g); (c), (f) and (g); (d), (e) and (f); (d), (e) and (g); (d), (f) and (g); (e), (f) and (g); (a), (b), (c) and (d); (a), (b), (c) and (e); (a), (b), (c) and (f); (a), (b), (c) and (g); (a), (b), (d) and (e); (a), (b), (d) and (f); (a), (b), (d) and (g); (a), (b), (e) and (f); (a), (b), (e) and (g); (a), (b), (f) and (g); (a), (c), (d) and (e); (a), (c), (d) and (f); (a), (c), (d) and (g); (a), (c), (e) and (f); (a), (c), (e) and (g); (a), (c), (f) and (g); (a), (d), (e) and (f); (a), (d), (e) and (g); (a), (d), (f) and (g); (a), (e), (f) and (g); (a), (c), (d), (e) and (f); (a), (c), (d), (f) and g); (a), (c), (e), (f) and (g); (a), (d), (e), (f) and (g); (b), (c), (d), (e) and (f); (b, c), (d), (e) and (g); (b), (c), (d), (f) and (g); (b), (c), (e), (f) and (g); (b), (d), (e), (f) and (g); (c), (d), (e), (f) and g); (a), (b), (c), (d), (e) and (f); (a), (b), (c), (d), (e) and (g); (a), (b), (c), (d), (f) and (g); (a), (b), (c), (e), (f) and (g); (a), (b), (d), (e), (f) and (g); (a), (c), (d), (e), (f) and (g); (b), (c), (d), (e), (f) and (g); or (a), (b), (c), (d), (e), (f) and (g). The combinations of (a) to (g) are independently selectable from this list.

The method preferably comprises detecting in vitro an immune response (i) Rv0840c (SEQ ID NO: 6) or one or more fragments thereof; (ii) TBFG_13463 (SEQ ID NO: 1) or one or more fragments thereof; (iii) Rv1677 (SEQ ID NO: 7) or one or more fragments thereof; (iv) Rv3845 (SEQ ID NO: 4) or one or more fragments thereof; and (v) Rv2654c (SEQ ID NO: 3) or one or more fragments thereof. In the definition of (i) to (v) given above, an immune response to any combination of one or more of (i) to (iv) may be detected in vitro. For instance, for each definition of (i) to (iv), an immune response may be detected in vitro to: (i); (ii); (iii); (iv); (v); (i) and (ii); (i) and (iii); (i) and (iv); (i) and (v); (ii) and (iii); (ii) and (iv); (ii) and (v); (iii) and (iv); (iii) and (v); (iv) and (v); (i), (ii) and (iii); (i), (ii) and (iv); (i), (ii) and (v); (i), (iii) and (iv); (i), (iii) and (v); (i), (iv) and (v); (ii), (iii) and (iv); (ii), (iii) and (v); (ii), (iv) and (v); (iii), (iv) and (v); (i), (ii), (iii) and (iv); (i), (ii), (iii) and (v); (i), (ii), (iv) and (v); (i), (iii), (iv) and (v); (ii), (iii), (iv) and (v); or (i), (ii), (iii), (iv) and (v). The combinations of (i) to (v) are independently selectable from this list.

The method may comprise detecting in vitro an immune response (i) Rv0840c (SEQ ID NO: 6) or one or more fragments thereof; (ii) TBFG_13463 (SEQ ID NO: 1) or one or more fragments thereof; (iii) Rv1677 (SEQ ID NO: 7) or one or more fragments thereof; and (iv) Rv2654c (SEQ ID NO: 3). In one aspect, the method comprises detecting in vitro an immune response to Rv0840c (SEQ ID NO: 6) or one or more fragments thereof.

Fragments

A fragment of Rv0840c (SEQ ID NO: 6), TBFG_13463 (SEQ ID NO: 1), Rv1677 (SEQ ID NO: 7), Rv2654c (SEQ ID NO: 3), Rv3845 (SEQ ID NO: 4), Rv1495 (SEQ ID NO: 5), or Mtub2_17866 (SEQ ID NO: 2) may be a sequence comprising five or more amino acids that is derived by truncation at the N-terminus and/or C-terminus of the parent sequence. For instance, the fragment may comprise about 5 or more, about 6 or more, about 7 or more, about 8 or more, about 9 or more, about 10 or more, about 11 or more, about 12 or more, about 13 or more, about 14 or more, about 15 or more, about 16 or more, about 17 or more, about 18 or more, about 19 or more, about 20 or more, about 21 or more, about 22 or more, about 23 or more, about 24 or more, about 25 or more, about 26 or more, or about 27 or more amino acids. The fragment may be from about 5 to about 27, from about 6 to about 26, from about 7 to about 25, from about 8 to about 24, from about 9 to about 23, from about 10 to about 22, from about 11 to about 21, from about 12 to about 20, from about 13 to about 19, from about 14 to about 18, from about 12 to about 18, from about 12 to about 15, from about 15 to about 18, from about 13 to about 17, from about 14 to about 16, from about 5 to about 10, from about 10 to about 15, from about 15 to about 20, from about 20 to about 25 or from about 10 to about 20 amino acids in length.

The fragments may be chemically derived from the parent protein, for example by proteolytic cleavage, or can be derived in an intellectual sense from the parent protein, for example by making use of the amino acid sequence of the parent protein and synthesising fragments based on the sequence. Fragments may be synthesised using methods well known in the art.

The term "fragment" includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) J. Immunol. 159, 3230-3237. This approach involves making pseudopeptides containing changes involving the backbone, and not the orientation of side chains. Meziere et al (1997) show that, at least for MHC class II and T helper cell responses, these pseudopeptides are useful. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the carbon atoms of the amino acid residues is used; it is particularly preferred if the linker moiety has substantially the same charge distribution and substantially the same planarity as a peptide bond. It will also be appreciated that the fragment may conveniently be blocked at its N- or C-terminus so as to help reduce susceptibility to exoproteolytic digestion. For example, the N-terminal amino group of the peptides may be protected by reacting with a carboxylic acid and the C-terminal carboxyl group of the peptide may be protected by reacting with an amine. One or more additional amino acid residues may also be added at the N-terminus and/or C-terminus of the fragment, for example to increase the stability of the fragment. Other examples of modifications include glycosylation and phosphorylation. Another potential modification is that hydrogens on the side chain amines of R or K may be replaced with methylene groups ($-NH_2 \rightarrow -NH(Me)$ or $-N(Me)_2$).

Fragments of Rv0840c (SEQ ID NO: 6), TBFG_13463 (SEQ ID NO: 1), Rv1677 (SEQ ID NO: 7), Rv2654c (SEQ ID NO: 3), Rv3845 (SEQ ID NO: 4), Rv1495 (SEQ ID NO: 5), or Mtub2_17866 (SEQ ID NO: 2) may also include variants of fragments that increase or decrease the fragments' half-life in vivo. Examples of variants capable of increasing the half-life of fragments according to the invention include peptoid analogues of the fragments, D-amino acid derivatives of the fragments, and peptide-peptoid hybrids. The fragment may also comprise D-amino acid forms of the fragment. The preparation of polypeptides using D-amino acids rather than L-amino acids greatly decreases any unwanted breakdown of such an agent by normal metabolic processes, decreasing the amounts of agent which needs to be administered, along with the frequency of its administration. D-amino acid forms of the parent protein may also be used.

The fragments provided by the present invention may be derived from splice variants of the parent proteins encoded by mRNA generated by alternative splicing of the primary transcripts encoding the parent protein chains. The fragments may also be derived from amino acid mutants, glycosylation variants and other covalent derivatives of the parent proteins which retain at least an MHC-binding or antibody-binding property of the parent protein. Exemplary derivatives include molecules wherein the fragments of the invention are covalently modified by substitution, chemical, enzymatic, or other appropriate means with a moiety other than a naturally occurring amino acid.

The method may comprise detecting in vitro an immune response to one or more fragments of Rv0840c (SEQ ID NO: 6), TBFG_13463 (SEQ ID NO: 1), Rv1677 (SEQ ID NO: 7), Rv2654c (SEQ ID NO: 3), Rv3845 (SEQ ID NO: 4), Rv1495 (SEQ ID NO: 5), or Mtub2_17866 (SEQ ID NO: 2). For instance, the method may comprise detecting in vitro an immune response to two or more, three or more, four or more, five or more, six or more, seven or more, eight or more, nine or more, 10 or more, 11 or more, 12 or more, 13 or more 14 or more, 15 or more, 16 or more, 17 or more, 18 or more, 19 or more, 20 or more, 25 or more or 30 or more fragments to Rv0840c (SEQ ID NO: 6), TBFG_13463 (SEQ ID NO: 1), Rv1677 (SEQ ID NO: 7), Rv2654c (SEQ ID NO: 3), Rv3845 (SEQ ID NO: 4), Rv1495 (SEQ ID NO: 5), or Mtub2_17866 (SEQ ID NO: 2). If the method comprises detecting an immune response to two or more fragments derived from a particular protein, all of the fragments derived from that protein may be the same. Alternatively, some or all of the fragments derived from that protein may be different. For instance, if the method comprises detecting an immune response to 3 fragments derived from Rv0840c (SEQ ID NO: 6), the 3 fragments may be (i) 3 of the same fragment; (ii) 2 of the same fragment and one different fragment; or (iii) 3 different fragments.

In some aspects, the method of the invention comprises detecting in vitro an immune response to one or more pools of fragments. Pools of fragments are described in detail below.

Samples

The in vitro detection of an immune response to one or more of (a) to (g) defined above is performed using a sample obtained from the subject. The sample may be a body fluid, such as blood, plasma, serum, sputum or other respiratory secretions, saliva, urine or cerebrospinal fluid. The sample is preferably blood, plasma, serum, or sputum or other respiratory secretions. Alternatively, the sample may be a tissue sample, such as a biopsy or aspirate. For instance, the sample may be a lymph node aspirate, or a sample taken from within or around a tuberculosis lesion such as a granuloma. In another aspect, the sample may be derived from a body fluid or tissue sample, such as a cell lysate.

Subject

The method of the invention may be used to diagnose *M. tuberculosis* complex infection in any suitable subject. The subject is generally a human subject. Alternatively, the subject may be produced another animal or mammal, for instance a commercially farmed animal, such as a horse, cow, sheep or pig, a laboratory animal, such as a mouse or rat, a pet animal, such as a cat, dog, rabbit or guinea pig, or another animal such as a bird or primate.

Immune Responses

The immune response that is detected in vitro may be any response that is triggered by one or more of (a) to (g). The immune response may be mediated by any type of immune cell. For instance the immune response may be mediated by T-cells, B-cells, dendritic cells, neutrophils, basophils, mast cells, eosinophils, innate lymphoid cells (ILCs), natural killer (NK) cells, monocytes, macrophages and/or thymocytes. The immune response is preferably a T-cell response. The T-cell response is preferably cytokine secretion, and more preferably IFN-gamma (IFNγ) secretion. The T-cell response may be T-cell proliferation. Alternatively, the immune response may be a B-cell response. The B-cell response may be B-cell proliferation or antibody production or secretion. The immune response is preferably the production of antibodies against one or more of (a) to (g) as defined above. Methods of measuring T-cell proliferation, B-cell proliferation, cytokine secretion, and antibody secretion or production are well known in the art.

The immune response may occur in vitro. Preferably, the immune response is an in vitro cell mediated immune (CMI) response. As described in more detail below, a CMI response is an immune response that does not involve antibodies. Instead, a CMI response may involve phagocyte activation, cytotoxic-T cell activation, increase in production of various cytokines and/or the release of various cytokines in response to an antigen. Methods for detecting in vitro CMI responses are known in the art and are described in more detail below.

Alternatively, the immune response may occur in vivo. For instance, antibodies against one or more of (a) to (g) as defined above may be produced in vivo, but detected in vitro using a method of the invention. For example, antibodies may be produced in the subject and removed from the subject in a sample, such as a blood sample. The sample (and antibodies) may then be contacted with one or more of (a) to (g) as defined above in order to detect the presence of the antibodies and/or quantify the antibodies, for example by an enzyme-linked immunosorbent assay (ELISA). ELISAs are described in more detail in Examples 1 to 3 below. In vivo T-cell proliferation and B-cell proliferation may also be measured in vitro. For instance, a blood sample from the subject may be contacted with one or more of (a) to (g) and the prevalence of antigen-specific T-cells and/or B-cells measured.

The method of the invention may detect the presence or absence of an immune response. The presence of an immune response to one or more of (a) to (g) as defined above may indicate that the subject is infected with *M. tuberculosis*. The absence of an immune response to one or more of (a) to (g) defined above may indicate that the subject is not infected with *M. tuberculosis*. In methods involving detecting an immune response to two or more of (a) to (g) defined above, the presence of an immune response to one or more of (a) to (g) may indicate infection, as discussed in more detail below.

Assays for CMI Responses

Cell Mediated Immune (CMI) responses are commonly used to define the immune status of an individual. Typically, in the art of clinical immunology, the term CMI response encompasses in vivo skin testing, lymphocyte proliferation assays, and the in vitro detection of cytokines produced by peripheral blood mononuclear cells (PBMC) in the presence of a specific antigen. The method of the present invention may comprise detecting an in vitro cell mediated immune response. In particular, the in vitro cytokine-based CMI response to the proteins and peptides or the present invention may be detected. This assay is hereinafter referred to as a "CMI Assay".

The cells of the immune system are capable of producing immune effector molecules such as cytokines following stimulation by an antigen. CMI Assays involve incubating a cell sample with an antigen and measuring for the presence (or absence) or quantity of an immune effector molecule such as a cytokine to provide an indication of the ability of the individual to generate a cell-mediated immune response to the selected antigen. Cells for use in a CMI Assay include isolated populations of lymphocytes (particularly T-cells) and antigen presenting cells (APCs). APCs are involved in processing the antigen in order that the latter may be recognised by T-cell receptors on the surface of each T-cell. Antigen recognition may induce cytokine production. Cells producing cytokines may be identified flow cytometry. Flow cytometry may be used to quantify the frequency of cytokine producing cells, and/or the amount of cytokine production by the cells. Antigen-induced cytokines may be released into the assay medium and detected directly by, for example, ELISA methods, or quantified in terms of the frequency of cytokine-secreting T-cells using an enzyme-linked immunospot assay (ELISPOT). The method of the invention preferably comprises an ELISPOT.

The enzyme-linked immunospot assay (ELISPOT), otherwise known as the filter immunoplaque assay, was initially developed to detect and quantitate individual antibody-secreting B cells. At the time it was developed, the technique provided a rapid and versatile alternative to conventional plaque-forming cell assays. Recent modifications have improved the sensitivity of the ELISPOT such that cells producing as few as 100 molecules of a specific protein per second can be detected. This makes ELISPOT assays much more sensitive than conventional ELISA assays. ELISPOT assays take advantage of the relatively high concentration of a given proteinaceous cell product (such as a cytokine) in the environment immediately surrounding the protein-secreting cell. These cell products are captured and detected using high-affinity antibodies. The ELISPOT assay is reviewed in Current Protocols in Immunology, Unit 6.19 pages 6.19. 1-8.

The ELISPOT assay typically involves six steps: (1) coating a purified cytokine-specific antibody to a membrane-backed microtiter plate; (2) blocking the plate to prevent non-specific absorption of any other proteins; (3) incubating the cytokine-secreting cells with appropriate reagents; (4) removal of cells and reagents; (5) adding a labelled second anti-cytokine antibody; and (6) detecting the antibody-cytokine complex on the membrane.

The method of the invention preferably comprises a T-SPOT.TB assay (Oxford Immunotec, Oxford, United Kingdom). The T-SPOT.TB assay is a simplified variant of the ELISPOT assay technique. The T-SPOT.TB assay is designed for the detection of effector T cells that respond to stimulation by antigens specific for *M. tuberculosis*. The assay enumerates individual activated TB-specific T cells. It is suitable for use with all patients at risk of latent TB infection (LTBI) or suspected of having TB disease, regardless of age, sex, ethnicity, therapy or immune status. Two separate panels of antigens, which simulate the well characterised RD1 proteins ESAT-6 and CFP10, are used to optimise the sensitivity of the test.

*M. tuberculosis* Proteins

In some aspects, the method of the invention further comprises detecting one or more additional *M. tuberculosis* proteins. The one or more additional *M. tuberculosis* protein may be any *M. tuberculosis* protein. Numerous *M. tuberculosis* proteins are well known in the art. The one or more additional *M. tuberculosis* protein may comprise a RD1 protein. The RD1 protein may comprise one or both of CFP-10 and ESAT-6.

Fragment Pools

The method of the invention may comprise detecting in vitro an immune response to one or more pools of fragments, wherein each pool comprises two or more fragments derived from TBFG_13463 (SEQ ID NO: 1), Mtub2_17866 (SEQ ID NO: 2), Rv2654c (SEQ ID NO: 3), Rv3845 (SEQ ID NO: 4), Rv1495 (SEQ ID NO: 5), Rv0840c (SEQ ID NO: 6) or Rv1677 (SEQ ID NO: 7). For example, each pool may comprise three or more, four or more, five or more, six or more, seven or more, eight or more, nine of more, 10 or more, 15 or more, 20 or more, 25 or more, 50 or more, 75 or more, 100 or more, 200 or more, or 250 or more, fragments derived from TBFG_13463 (SEQ ID NO: 1), Mtub2_17866 (SEQ ID NO: 2), Rv2654c (SEQ ID NO: 3), Rv3845 (SEQ ID NO: 4), Rv1495 (SEQ ID NO: 5), Rv0840c (SEQ ID NO: 6) or Rv1677 (SEQ ID NO: 7).

The method may comprise detecting in vitro an immune response to one or more, two or more, three or more, four or more, five or more, six or more, seven or more, eight or more, 9 or more, 10 or more, 11 or more, 12 or more, 13 or more, or 14 or more pools of fragments as defined above. Where the method comprises detecting in vitro an immune response to two or more pools of fragments, each pool may comprise fragments derived from the same or different protein selected from TBFG_13463 (SEQ ID NO: 1), Mtub2_17866 (SEQ ID NO: 2), Rv2654c (SEQ ID NO: 3), Rv3845 (SEQ ID NO: 4), Rv1495 (SEQ ID NO: 5), Rv0840c (SEQ ID NO: 6) and Rv1677 (SEQ ID NO: 7). Where the method comprises detecting in vitro an immune response to three or more pools of fragments, each of the pools may comprise fragments derived from a different protein. Alternatively, some or all of the pools may comprise fragments derived from the same protein. For instance, if the method comprises detecting in vitro an immune response to three pools of fragments, all of the pools may comprise fragments derived from the same protein. Alternatively, two of the pools may comprise fragments derived from the same protein and the third pool may comprise fragments derived from a different protein, or each of the three pools may comprise fragments derived from a different protein. If any of the two or more pools are derived from the same protein, those pools may comprise the same or different fragments.

As set out below, the method may also comprise detecting in vitro an immune response to one or more protein fragment libraries and/or one or more epitope pools. Where the method comprises detecting in vitro immune response to one or more protein fragment libraries and one or more epitope pools, the fragments comprised in the protein fragment library or libraries may be derived from the same protein or from two or more different proteins as the fragments comprised in the epitope pool(s).

Protein Fragment Libraries

In one aspect of the invention, the fragments in a pool form a protein fragment library. A protein fragment library comprises a plurality of fragments derived from a parent protein (for the present invention, TBFG_13463 (SEQ ID NO: 1), Mtub2_17866 (SEQ ID NO: 2), Rv2654c (SEQ ID NO: 3), Rv3845 (SEQ ID NO: 4), Rv1495 (SEQ ID NO: 5), Rv0840c (SEQ ID NO: 6) or Rv1677 (SEQ ID NO: 7)), that together encompass at least 10%, such as at least 20%, at least 30%, at least 40%, at least 50%, at least 60%, at least 70%, at least 75%, at least 80%, at least 85%, at least 90%, at least 95%, at least 98%, at least 99%, or 100%, of the sequence of the parent protein. In the present invention, the fragments in a pool preferably form a protein fragment library encompassing at least 80% of the sequence of the protein from which the fragments are derived. More preferably, the fragments in a pool form a protein fragment library encompassing the entire sequence of the protein from which the fragments are derived.

The protein fragment library may comprise fragments that are capable of stimulating CD4+ and/or CD8+ T-cells. Preferably, the protein fragment library comprises fragments that are capable of stimulating both CD4+ and CD8+ T-cells. It is known in the art that the optimal fragment size for stimulation is different for CD4+ and CD8+ T-cells. Fragments consisting of about 9 amino acids (9mers) typically stimulate CD8+ T-cells only, and fragments consisting of about 20 amino acids (20mers) typically stimulate CD4+ T-cells only. Broadly speaking, this is because CD8+ T-cells tend to recognise their antigen based on its sequence, whereas CD4+ T-cells tend to recognise their antigen based on its higher-level structure. However, fragments consisting of about 15 amino acids (15mers) may stimulate both CD4+ and CD8+ T cells. Accordingly, the protein fragment library preferably comprises fragments that are about 15 amino acids, such as about 12 amino acids, about 13 amino acids, about 14 amino acids, about 15 amino acids, about 16 amino acids, about 17 amino acids or about 18 amino acids in length.

All of the fragments in a pool may be the same length. Alternatively, a pool may comprise fragments of different lengths. Fragment lengths are discussed above.

A protein fragment library may comprise fragments whose sequences overlap. Accordingly, each pool may comprise fragments whose sequences overlap. The sequences may overlap by one or more, such as two or more, three or more, four or more, five or more, six or more, seven or more, eight or more, nine or more, 10 or more, 11 or more, 12 or more, 13 or more, 14 or more, 15 or more, 16 or more, 17 or more, 18 or more, 19 or more, or 20 or more, amino acids. Preferably, the sequences overlap by 9 or more amino acids, such as 10 or more, 11 or more or 12 or more amino acids, as this maximises the number of fragments that comprise the 9mers capable of stimulating CD8+ T-cells. More preferably, the sequences overlap by 11 amino acids. All of the overlapping fragments in a pool may overlap by the same number of amino acids. Alternatively, a pool may comprise fragments whose sequences overlap by different numbers of amino acids.

The protein fragment library may comprise fragments of 12 to 18 (such as 12 to 15, 15 to 18, 13 to 17, or 14 to 16) amino acids in length that overlap by 9 to 12 (such as 9 to 11 or 10 to 12) amino acids. For instance, the protein fragment library may comprise fragments of (i) 14 amino acids in length that overlap by 9, 10, or 11 amino acids, (ii) 15 amino acids in length that overlap by 9, 10, or 11 amino acids, or (iii) 16 amino acids in length that overlap by 9, 10, or 11 amino acids. The protein fragment library preferably comprises fragments of 15 amino acids in length that overlap by 11 amino acids.

General properties of fragments are set out above.

Epitope Pools

An epitope is the part of an antigen that is recognised by the immune system. Specifically, an epitope is the part of an antigen that is recognised by an antibody, B-cell, or T-cell. Accordingly, a T-cell epitope is the part of an antigen that is recognised by a T-cell. As T-cells recognise antigen via the T-cell receptor (TCR), a T-cell epitope may be the part of an antigen that binds to (i.e. is recognised) by the T-cell receptor. Similarly, a B-cell epitope is the part of an antigen that is recognised by a B-cell. As B-cells recognise antigen via the B-cell receptor (BCR), a B-cell epitope may be the part of an antigen that binds to (i.e. is recognised) by the T-cell receptor.

B-cell and T-cell epitopes may be identified by testing whole and fragmented native proteins, or recombinant antigenic proteins, for recognition by the BCR or TCR respectively. B-cell and T-cell epitopes may also be identified using in silico methods, such as in the present Examples. The results of in silico epitope identification can be verified by testing a peptide having the sequence of the epitope for antigenicity. Methods for testing for antigenicity are well known in the art. For example, blood samples from subject can be screened for the presence of antibodies to the epitope by ELISA.

In one aspect of the invention, one or more of the fragments in a pool comprise a T-cell epitope or a B-cell epitope of the protein from which the fragments are derived. This gives rise to an "epitope pool". One or more of the fragments may comprise a T-cell epitope and a B-cell epitope. Similarly, one or more of the fragments may comprise one or more (such as two, three or four) T-cell epitopes and/or one or more (such as two, three or four) B-cell epitopes. If a fragment comprises more that one T-cell or B-cell epitope, the epitopes may be the same or different. The T-cell epitope may be a CD4+ T-cell epitope or a CD8+ T-cell epitope. Alternatively, the T-cell epitope may be an epitope for both CD4+ and CD8+ T-cells. Table 4 lists exemplary CD4+ T-cell epitopes of the invention. Table 5 lists exemplary CD8+ T-cell epitopes of the invention. Table 6 lists exemplary B-cell epitopes of the invention. The one or more fragments in a pool may comprise any of these epitopes. The one or more fragments in a pool may comprise any of number and combination of these epitopes.

General properties of fragments are set out above. In addition, and as set out above in relation to fragments that form a protein fragment library, the fragments comprising a T-cell epitope or a B-cell epitope may be about 12 amino acids, about 13 amino acids, about 14 amino acids, about 15 amino acids, about 16 amino acids, about 17 amino acids or about 18 amino acids in length. The fragments are preferably about 15 amino acids in length. Alternatively, the fragments may be at least 9, at least 10, at least 11, at least 12, at least 13, at least 14, at least 15, at least 16, at least 17, at least 18, at least 19, at least 20, at least 21, at least 22, at least 23, at least 24 or at least 25 amino acids in length. All of the fragments in a pool may be the same length, or a pool may comprise fragments of different lengths.

The fragments comprising a T-cell epitope or a B-cell epitope may have overlapping sequences, i.e. each pool may comprise fragments whose sequences overlap. The sequences may overlap by at least one, such as at least two, at least three, at least four, at least five, at least six, at least seven, at least eight, at least nine, at least 10, at least 11, at least 12, at least 13, at least 14, at least 15, at least 16, at least 17, at least 18, at least 19, or at least 20, amino acids. Preferably, the sequences overlap by 9 or more amino acids, such as 10 or more, 11 or more or 12 or more amino acids. Most preferably, the sequences overlap by 11 amino acids. All of the overlapping fragments in a pool may overlap by the same number of amino acids. Alternatively, a pool may comprise fragments whose sequences overlap by different numbers of amino acids.

The fragments comprising a T-cell epitope or a B-cell epitope may be 12 to 18 (such as 12 to 15, 15 to 18, 13 to 17, or 14 to 16) amino acids in length and/or overlap by 9 to 12 (such as 9 to 11 or 10 to 12) amino acids. For instance, the fragments may be (i) 14 amino acids in length and overlap by 9, 10, or 11 amino acids, (ii) 15 amino acids in length and overlap by 9, 10, or 11 amino acids, or (iii) 16 amino acids in length and overlap by 9, 10, or 11 amino acids. In some instances, the fragments are preferably 15 amino acids in length and overlap by 11 amino acids.

Cells

In one aspect, the method of the invention comprises contacting a population of immune cells obtained from the subject with the one or more of (a) to (g) as defined above. The one or more of (a) to (g) may comprise one or more protein fragment libraries and/or one or more epitope pools as discussed above.

The population is typically contacted with a sufficient amount of the one or more of (a) to (g) to generate an immune response to the one or more of (a) to (g). The population may be contacted with any amount of the one or more of (a) to (g), such as about 1 ng/ml, about 5 ng/ml, about 10 ng/ml, about 50 ng/ml, about 100 ng ml, about 500 ng/ml, about 1 µg/ml, about 5 µg/ml, about 10 µg/ml, about 50 µg ml, about 500 µg/ml, 1 mg/ml, about 5 mg/ml, about 10 mg/ml, about 50 mg/ml, about 100 mg ml, or about 500 mg/ml of the one or more of (a) to (g), The population of immune cells may comprise one or more types of immune cells selected from T-cells, B-cells, dendritic cells, neutrophils, basophils, mast cells, eosinophils, innate lymphoid cells (ILCs), natural killer (NK) cells, monocytes, macrophages and thymocytes. The population may comprise all of these types of immune cells. In one aspect, the population of immune cells comprises T-cells. Preferably, the population of immune cells comprises T-cells and antigen presenting cells, such as B-cells, dendritic cells, or macrophages. In another aspect, the population of immune cells comprises B-cells.

The population of immune cells may be further contacted with one or more additional M. tuberculosis proteins as defined above. The population may be contacted with enough of the one or more M. tuberculosis proteins to generate an immune response to the one or more proteins. For instance, the population may be contacted with about 1 ng/ml, about 5 ng/ml, about 10 ng/ml, about 50 ng/ml, about 100 ng ml, about 500 ng/ml, about 1 µg/ml, about 5 µg/ml, about 10 µg/ml, about 50 µg/ml, about 100 µg ml, about 500 µg/ml, 1 mg/ml, about 5 mg/ml, about 10 mg/ml, about 50 mg/ml, about 100 mg ml, or about 500 mg/ml of one or more additional M. tuberculosis proteins. For instance, the population of immune cells may be further contacted with two or more additional M. tuberculosis proteins. If the population is contacted with two or more additional M. tuberculosis* proteins, the population may be contacted with the two or more additional *M. tuberculosis* proteins concurrently or sequentially. Furthermore, the population may be contacted with the one or more or two or more of (a) to (g) and the one or more or two or more *M. tuberculosis* proteins concurrently or sequentially. The population may be contacted with the same or different amounts of the two or more additional *M. tuberculosis* proteins. Amounts of *M. tuberculosis* proteins are discussed above.

In another aspect, the method of the invention comprises detecting in vitro an immune response to two or more of (a) to (g) as defined above, wherein the same population of immune cells is contacted with the two or more of (a) to (g). The two or more of (a) to (g) may comprise one or more protein fragment libraries and/or one or more epitope pools as discussed above. The population may be contacted with the two or more of (a) to (g) concurrently or sequentially. The population may be contacted with the same or different amounts of the two or more of (a) to (g). Amounts of (a) to (g) are discussed above.

In this aspect, the population of immune cells may be further contacted with one or more additional *M. tuberculosis* proteins as defined above. For instance, the population of immune cells may be further contacted with two or more additional *M. tuberculosis* proteins. If the population is contacted with two or more additional *M. tuberculosis* proteins, the population may be contacted with the two or more additional *M. tuberculosis* proteins concurrently or sequentially. Furthermore, the population may be contacted with the one or more or two or more of (a) to (g) and the one or more or two or more *M. tuberculosis* proteins concurrently or sequentially. The population may be contacted with the same or different amounts of the two or more additional *M. tuberculosis* proteins. Amounts of *M. tuberculosis* proteins are discussed above.

In further aspect, the method of the invention comprises detecting in vitro an immune response to two or more of (a) to (g) as defined above, wherein each of the two or more of (a) to (g) is contacted with a different population of immune cells. The two or more of (a) to (g) may comprise one or more protein fragment libraries and/or one or more epitope pools as discussed above. Each population of immune cells may comprise the same type or types of immune cell(s). Alternatively, each population of immune cells may comprise a different type or types of immune cell(s). Exemplary immune cells are detailed above. Furthermore, the two or more of (a) to (g) may be contacted with the different populations of immune cells concurrently or sequentially. Each different population may be contacted with the same or different amounts of the two or more of (a) to (g). Amounts of (a) to (g) are discussed above.

In this further aspect, the method may further comprise detecting in vitro an immune response to one or more additional *M. tuberculosis* proteins as defined above, wherein each of the additional *M. tuberculosis* proteins is contacted with a different population of immune cells. For instance, two or more additional *M. tuberculosis* proteins may each be contacted with a different population of immune cells. Each population of immune cells may comprise the same type or types of immune cell(s). Alternatively, each population of immune cells may comprise a different type or types of immune cell(s). Exemplary immune cells are detailed above. Furthermore, the two or more additional *M. tuberculosis* proteins may be contacted with the different populations of immune cells concurrently or sequentially. Each different population may be contacted with the same or different amounts of the two or more additional *M. tuberculosis* proteins. Amounts of *M. tuberculosis* proteins are discussed above.

The contacting may be carried out in any suitable volume. Typical volumes of the samples range from about 100 to about 1 ml, preferably from about 50 µl to about 500 µl, more preferably from about 100 µl to about 200 µl. Typically, the length of time for which the cells are contacted with the one or more of (a) to (g) (and optionally the one or more additional *M. tuberculosis* proteins) is from about 5 minutes to about 50 hours, for example from about 10 minutes to about 40 hours, from about 20 minutes to about 30 hours, from about 30 minutes to about 20 hours, from about 45 minutes to about 12 hours, from about 1 hour to about 6 hours, preferably from about 10 minutes to about 2 hours. The cells may be contacted with the antigens overnight.

The cells may be contacted with the antigen at any suitable temperature. The suitable temperature is typically in the same range as the normal body temperature of the human or animal from which the cells are derived. Typically, the incubation is carried out at a fixed temperature between about 4° C. and about 38° C., preferably from about 20° C. to about 38° C., more preferably at about 37° C.

The cells are typically present in wells. The cells are preferably present in the wells of a flat plate, which is preferably a membrane-backed plate. The samples are more preferably present in the wells of a standard 96 or 384 well plate. Such plates are commercially available Fisher scientific, VWR suppliers, Nunc, Starstedt or Falcon. The wells typically have a capacity of from about 25 µl to about 250 µl, from about 30 µl to about 200 µl, from about 40 µl to about 150 µl or from about 50 to 100 µl. The cells obtained from the subject can be cultured before being used in the methods. This allows equal numbers of adherent cells to be present in each sample being assayed. Alternatively, if the cells are immobilized or captured, the cells, such as fresh blood cells, can be counted before plating. Techniques for culturing cells are well known to a person skilled in the art. The cells are typically cultured under standard conditions of 37° C., 5% $CO_2$ in medium supplemented with serum.

The cells may be cultured in any suitable flask or vessel and then be transferred to wells. The cells are typically cultured in wells. The cells are preferably cultured in a flat plate comprising two or more wells, such as a standard 96 or 384 well plate. Incubating the cells with the marker typically involves replacing the culture medium in each well with a suitable solution comprising the marker. Suitable solutions are well known to a person skilled in the art.

Interpretation of Results

As set out above, the method of the invention comprises detecting in vitro an immune response to one or more *M. tuberculosis* antigens. Detection of an immune response indicates that the subject has *M. tuberculosis* complex infection. The lack of detection (or absence of detection) of an immune response indicates that the subject does not have *M. tuberculosis* complex infection. Accordingly, the method of the invention preferably comprises detecting in vitro the presence or absence of an immune response to one or more *M. tuberculosis* antigens.

In other words, the detection, or the presence, of an immune response to one or more *M. tuberculosis* antigens indicates that the subject has *M. tuberculosis* complex infection. The lack of detection, or the absence, of an immune response to one or more *M. tuberculosis* antigens indicates that the subject does not have *M. tuberculosis* complex infection.

Different criteria may be applied for determining a positive test result (i.e. the presence of *M. tuberculosis* complex infection in the subject). Firstly, a positive test result is obtained if an immune response to any one or more (a) to (g) defined above is detected. Secondly, a positive test result is obtained if an immune response to any one or more (a) to (g) defined above is detected and an immune response to any one or more additional *M. tuberculosis* antigens defined above is detected. The immune response to the one or more of (a) to (g) and, if applicable, the one or more additional *M. tuberculosis* protein may be detected (or not detected) in the same or different population of cells, as discussed above.

In a preferred embodiment, the invention provides a method for determining whether or not a subject has a *Mycobacterium tuberculosis* (*M. tuberculosis*) complex infection, comprising detecting in vitro the presence or absence of an immune response to one or more of (a) Rv0840c (SEQ ID NO: 6) or one or more fragments thereof; (b) TBFG_13463 (SEQ ID NO: 1) or one or more fragments thereof; (c) Rv1677 (SEQ ID NO: 7) or one or more fragments thereof, (d) Rv2654c (SEQ ID NO: 3) or one or more fragments thereof; (e) Rv3845 (SEQ ID NO: 4) or one or more fragments thereof; (f) Rv1495 (SEQ ID NO: 5) or one or more fragments thereof; and (g) Mtub2_17866 (SEQ ID NO: 2) or one or more fragments thereof, wherein the presence of an immune response indicates that the subject has a *Mycobacterium tuberculosis* (*M. tuberculosis*) complex infection and wherein the absence of an immune response indicates that the subject does not have a *Mycobacterium tuberculosis* (*M. tuberculosis*) complex infection.

Kits

The invention also relates to a combination of components described herein suitable for use in a treatment of the invention which are packaged in the form of a kit in a container.

Specifically, the invention provides a kit for diagnosing *Mycobacterium tuberculosis* (*M. tuberculosis*) complex infection in a subject, comprising one or more of (a) Rv0840c (SEQ ID NO: 6) or one or more fragments thereof, (b) TBFG 13463 (SEQ ID NO: 1) or one or more fragments thereof, (c) Rv1677 (SEQ ID NO: 7) or one or more fragments thereof, (d) Rv2654c (SEQ ID NO: 3) or one or more fragments thereof, (e) Rv3845 (SEQ ID NO: 4) or one or more fragments thereof; (f) Rv1495 (SEQ ID NO: 5) or one or more fragments thereof; and (g) Mtub2_17866 (SEQ ID NO: 2) or one or more fragments thereof. Preferably, the kit contains one or more fragments as defined above in relation protein fragment librariesaor epitope pools.

The kit may further comprising a means for detecting the immune response. For instance, the kit may comprise some or all of the necessary equipment or reagents for performing an ELISA or an ELISPOT. In particular, the kit may comprise one or more standard 96 or 384-well flat-bottomed or membrane-backed plates. The kit may comprise the one or more of the necessary reagents for coating the relevant plates, and/or for blocking the plates to prevent non-specific absorption. The kit may comprise one or labelled antibodies for detecting cytokines or other immune products. The kit may comprise one or more detection reagents for detecting the labelled antibodies.

Medicaments, Methods and Therapeutic Use

The invention provides a composition comprising one or more of (a) to (g) as defined above, for use in treating or preventing M. tuberculosis complex infection in a subject. The invention additionally provides a method of treating or preventing M. tuberculosis complex infection in a subject, comprising administering to the subject one or more of (a) to (g) as defined above.

The M. tuberculosis complex infection may be active or latent infection.

Formulation of a suitable composition can be carried out using standard pharmaceutical formulation chemistries and methodologies all of which are readily available to the reasonably skilled artisan.

For example, the one or more of (a) to (g) can be combined with one or more pharmaceutically acceptable excipients or vehicles. Auxiliary substances, such as wetting or emulsifying agents, pH buffering substances and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol, thioglycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

Such compositions may be prepared, packaged, or sold in a form suitable for bolus administration or for continuous administration. Injectable compositions may be prepared, packaged, or sold in unit dosage form, such as in ampoules or in multi-dose containers containing a preservative. Compositions include, but are not limited to, suspensions, solutions, emulsions in oily or aqueous vehicles, pastes, and implantable sustained-release or biodegradable formulations. Such compositions may further comprise one or more additional ingredients including, but not limited to, suspending, stabilizing, or dispersing agents. In one embodiment of a composition for parenteral administration, the active ingredient is provided in dry (for e.g., a powder or granules) form for reconstitution with a suitable vehicle (e.g., sterile pyrogen-free water) prior to parenteral administration of the reconstituted composition. The compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Other parentally-administrable compositions which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Alternatively, the one or more of (a) to (g) may be encapsulated, adsorbed to, or associated with, particulate carriers. Suitable particulate carriers include those derived from polymethyl methacrylate polymers, as well as PLG microparticles derived from poly(lactides) and poly(lactide-co-glycolides). See, e.g., Jeffery et al. (1993) Pharm. Res. 10:362-368. Other particulate systems and polymers can also be used, for example, polymers such as polylysine, polyarginine, polyornithine, spermine, spermidine, as well as conjugates of these molecules.

The formulation of the composition will depend upon factors such as the nature of the substances in the composition and the method of delivery. The composition can be administered in a variety of dosage forms. It may be administered parenterally, subcutaneously, intravenously, intramuscularly, transdermally, intradermally, intraosseously or by infusion techniques. A physician will be able to determine the required route of administration for each particular individual.

The administered compositions will comprise a suitable concentration of the one or more of (a) to (g) which is effective without causing adverse reaction. Typically, the concentration of each protein in the composition will be in the range of 0.03 to 200 nmol/ml. More preferably in the range of 0.3 to 200 nmol/ml, 3 to 180 nmol/ml, 10 to 150 nmol/ml, 50 to 200 nmol/ml or 30 to 120 nmol/ml. The composition or formulations should have a purity of greater than 95% or 98% or a purity of at least 99%.

The composition may also comprise an adjuvant. The adjuvant is preferably administered in an amount which is sufficient to augment the effect of the one or more of (a) to (g). The adjuvant or other therapeutic agent may be an agent that potentiates the effects of the one or more of (a) to (g). For example, the other agent may be an immunomodulatory molecule or an adjuvant which enhances the response to the one or more of (a) to (g).

In one embodiment, the one or more of (a) to (g) is used in combination with one or more other therapeutic agents. The agents may be administered separately, simultaneously or sequentially. They may be administered in the same or different compositions as the one or more of (a) to (g). Accordingly, in a method of the invention, the subject may also be treated with a further therapeutic agent.

A composition may therefore be formulated with the one or more of (a) to (g) and also one or more other therapeutic molecules. The one or more of (a) to (g) may alternatively be used simultaneously, sequentially or separately with one or more other therapeutic compositions as part of a combined treatment.

Non-limiting examples of adjuvants include alum, monophosphoryl lipid, oligonucleotides, cholera toxin and Freund's incomplete adjuvant.

Administration of the one or more of (a) to (g) may be by any suitable method as described above. Suitable amounts of the one or more of (a) to (g) may be determined empirically, but typically are in the range given below. For prevention of M. tuberculosis complex infection, a single administration of the composition may be sufficient to have a beneficial effect for the patient. However, it will be appreciated that the beneficial effect may be greater if the composition is administered to the subject more than once, in which case typical administration regimes may be, for example, once or twice a week for 2-4 weeks every 6 months, or once a day for a week every four to six months.

Dosages for administration will depend upon a number of factors including the nature of the composition, the route of administration and the schedule and timing of the administration regime. Suitable doses may be in the order of up to 15 µg, up to 20 µg, up to 25 µg, up to 30 µg, up to 50 µg, up to 100 µg, up to 500 µg or more per administration. Suitable doses may be less than 15 µg, but at least 1 ng, or at least 2 ng, or at least 5 ng, or at least 50 ng, or least 100 ng, or at least 500 ng, or at least 1 µg, or at least 10 µg. For some molecules, the dose used may be higher, for example, up to 1 mg, up to 2 mg, up to 3 mg, up to 4 mg, up to 5 mg or higher. Such doses may be provided in a liquid formulation, at a concentration suitable to allow an appropriate volume for administration by the selected route.

The dose of the one or more of (a) to (g) to be administered in the composition may be determined according to various parameters, especially according to the age, weight and condition of the subject t to be treated; the route of administration; and the required regimen. A physician will be able to determine the required route of administration and dosage for any particular subject. A typical daily dose is from about 0.1 to 50 mg per kg of body weight, according to the activity of the specific inhibitor, the age, weight and conditions of the subject to be treated and the frequency and route of administration. The dose may be provided as a single dose or may be provided as multiple doses, for example taken at regular intervals, for example 2, 3 or 4 doses administered hourly.

The composition of the invention, or (a) to (g) as defined above, may be administered to the subject on one day. Alternatively, the composition of the invention (a) to (g) as defined above may be administered to the subject on at least two days, such as at least 3, at least 4, at least 5, at least 6, at least 7, at least 8, at least 9 or at least 10 days. The interval between the occasions may be from 1 to 28 days, such as 3 to 25 days, 6 to 22 days, 9 to 18 days or 12 to 15 days. Preferably, the interval between occasions is 1, 2, 3, 4, 5, 6, 7, 8, 9, 10, 11, 12, 13, 14, 15, 16, 17, 18, 19, 20, 21, 22, 23, 24, 25, 26, 27 or 28 days.

If the method of treating or preventing *M. tuberculosis* complex infection in a subject comprises administering to the subject two or more of (a) to (g) as defined above, each of the two or more of (a) to (g) may be administered to the subject singly or in combination.

The composition of the invention or (a) to (g) as defined above may be administered to any suitable subject. The subject is generally a human subject. The subject may be any of the animals or mammals mentioned above with reference to the method of diagnosis.

The subject may be an infant, a juvenile or an adult. The subject may be known to have a tuberculosis or is suspected of having tuberculosis. The subject may be susceptible to, or at risk from, the tuberculosis. For instance, the subject may be genetically predisposed tuberculosis, live in a high-risk region, or have a weakened immune system. The subject may be infected with HIV or have AIDS.

The invention may be used in combination with other means of, and substances for, treating preventing tuberculosis. In some cases, the composition of the invention or (a) to (g) as defined above may be administered simultaneously, sequentially or separately with other substances which are intended for treating tuberculosis or ameliorating the symptoms of tuberculosis, or for providing pain relief. The composition or (a) to (g) as defined above may be used in combination with existing treatments for tuberculosis and may, for example, be simply mixed with such treatments. Thus the invention may be used to increase the efficacy of existing treatments for disease.

EXAMPLES

Example 1

Analysis of *Mycobacterium tuberculosis* Genome Using the Platform NeutraCorp.

The genomes of *Mycobacterium tuberculosis* were analysed using the immunoinformatics platform developed by Proxagen (TradeMark: BG Per. No. 85788, of 27 Aug. 2013). Genomes obtained from clinical isolates were analysed for the identification of the immunogenic protein antigens. A total of 44 complete genomes for MTB were obtained from GOLD database.

TABLE 1 list of the MTB strain genomes used

| GOLD database number | MTB strain name |
| --- | --- |
| Gc00015 | *Mycobacterium tuberculosis* H37Rv (lab strain) |
| Gc00063 | *Mycobacterium tuberculosis* CDC1551 |
| Gc00577 | *Mycobacterium tuberculosis* H37Ra |
| Gc00578 | *Mycobacterium tuberculosis* F11 (ExPEC) |
| Gc01079 | *Mycobacterium tuberculosis* KZN 1435 (MDR) |
| Gc01851 | *Mycobacterium tuberculosis* KZN 4207 (DS) |
| Gc01885 | *Mycobacterium tuberculosis* CCDC5079 |
| Gc01886 | *Mycobacterium tuberculosis* CCDC5180 |
| Gc01929 | *Mycobacterium tuberculosis* CTRI-2 |
| Gc02147 | *Mycobacterium tuberculosis* UT205 |
| Gi00385 | *Mycobacterium tuberculosis* 210 |
| Gi01205 | *Mycobacterium tuberculosis* C |
| Gi01206 | *Mycobacterium tuberculosis* Haarlem |
| Gi01904 | *Mycobacterium tuberculosis* KZN 605 (XDR) |
| Gi02498 | *Mycobacterium tuberculosis* GM 1503 |
| Gi02503 | *Mycobacterium tuberculosis* 94_M4241A |
| Gi02507 | *Mycobacterium tuberculosis* 02_1987 |
| Gi02511 | *Mycobacterium tuberculosis* T17 |
| Gi02512 | *Mycobacterium tuberculosis* T46 |
| Gi02513 | *Mycobacterium tuberculosis* T92 |
| Gi02519 | *Mycobacterium tuberculosis* EAS054 |
| Gi02522 | *Mycobacterium tuberculosis* K85 |
| Gi02888 | *Mycobacterium tuberculosis* CPHL_A |
| Gi03342 | *Mycobacterium tuberculosis* H37Ra |
| Gi03359 | *Mycobacterium tuberculosis* 98-R604 INH-RTF-EM |
| Gi04656 | *Mycobacterium tuberculosis* KZN 4207 |
| Gi04663 | *Mycobacterium tuberculosis* KZN R506 |
| Gi04664 | *Mycobacterium tuberculosis* KZN V2475 |
| Gi05081 | *Mycobacterium tuberculosis* T85 |
| Gi05949 | *Mycobacterium tuberculosis* SUMu012 |
| Gi05950 | *Mycobacterium tuberculosis* SUMu011 |
| Gi05951 | *Mycobacterium tuberculosis* SUMu010 |
| Gi05952 | *Mycobacterium tuberculosis* SUMu009 |
| Gi05953 | *Mycobacterium tuberculosis* SUMu008 |
| Gi05954 | *Mycobacterium tuberculosis* SUMu007 |
| Gi05955 | *Mycobacterium tuberculosis* SUMu006 |
| Gi05956 | *Mycobacterium tuberculosis* SUMu005 |
| Gi05957 | *Mycobacterium tuberculosis* SUMu004 |
| Gi05958 | *Mycobacterium tuberculosis* SUMu003 |
| Gi05959 | *Mycobacterium tuberculosis* SUMu002 |
| Gi05960 | *Mycobacterium tuberculosis* SUMu001 |
| Gi12481 | *Mycobacterium tuberculosis* OSDD071 |
| Gi12482 | *Mycobacterium tuberculosis* OSDD504 |
| Gi12483 | *Mycobacterium tuberculosis* OSDD518 |

Analysis of the *Mycobacterium tuberculosis* Genomes and Protein Selection

Using the NeutraCorp (TradeMark: BG Per. No. 85788, of Aug. 27, 2013) immunoinformatic platform, we fully analysed the MTB genomes for the identification of all possible protein fragments with antigenic properties either T-cell epitopes and continuous B-cell epitopes. In each genome, Proteins with at least 1 available epitope (both T- and B-cell epitope) of in silico affinity higher than 1% of the theoretical were selected. These proteins have been analysed for the presence of T-cell epitopes for the HLA-DR alleles or allelic groups associated to susceptibility or to protection to develop TB as for the Table 2.

TABLE 2

|  | Positive association with developing active-TB | Negative association with developing active-TB |
|---|---|---|
| HLA-DR Alleles (4 digit) or groups (2 digit + XX) | DRB1*08XX, DRB1*14XX, DRB1*1501, DRB1*16XX | DRB1*03XX, DRB1*04XX, DRB1*0701, DRB1*10XX, DRB1*11XX, DRB1*13XX |

Proteins presenting a number of epitopes significantly higher (>3 SD of the mean of epitopes for each protein for all alleles) for HLA associated alleles or groups with active TB respect to HLA associated to protection to TB were selected.

Orthology analysis for all the protein identified were performed using the EGM2 software (Nucl. Acids Res. 2011 doi: 10.1093/nar/gkr1261). Selected proteins present in more than 20 common clinical strain genomes analysed were selected.

This resulted in a list of seven proteins as for the table 3.

TABLE 3

| # Seq ID | Protein name | Sequence |
|---|---|---|
| Seq ID#1 | TBFG_13463 | MTINNQFDDADTHGATSDFWCDAEWA GLRGPVAAGLGRAALVGYLSVPQGWT EANQANLAAGTEAEPNQALGWLPMQD IDAAAEAAAQPSHALGWLPIEEIDAA ASDDGEVSSSPQLPPRPFMMPHTPSG G |
| Seq ID#2 | Mtub2_17866 | MIDDRHKSTRRTCNHGGITWRVAATS ARSARSLATTHPEAGHYGLATWFTRM DAMTAPT |
| Seq ID#3 | Rv2654c | MSGHALAARTLLAAADELVGGPPVEA SAAALAGDAAGAWRTAAVELARALVR AVAESHGVAAVLFAATAAAAAAVDRG DPP |
| Seq ID#4 | Rv3845 | MDRVRRVVTDRDSGAGALARHPLAGR RTDPQLAAFYHRLMTTQRHCHTQATI AVARKLAERTRVTITTGRPYQLRDTN GDPVTARGAKELIDAHYHVDTRTHPH NRAHTDTMQNSKPAR |
| Seq ID#5 | Rv1495 | MNAPLRGQVYRCDLGYGAKPWLIVSN NARNRHTADVVAVRLTTTRRTIPTWV AMGPSDPLTGYVNADNIETLGKDELG DYLGEVTPATMNKINTALATALGLPW P |
| Seq ID#6 | Rv0840c | MEGTIAVPGGRVWFQRIGGGPGRPLL VVHGGPGLPHNYLAPLRRLSDEREVI FWDQLGCGNSACPSDVDLWTMNRSVA EMATVAEALALTRFHIFSHSWGGMLA QQYVLDKAPDAVSLTIANSTASIPEF SASLVSLKSCLDVATRSAIDRHEAAG TTHSAEYQAAIRTWNETYLCRTRPWP RELTEAFANMGTEIFETMFGPSDFRI VGNVRDWDVVDRLADIAVPTLLVVGR FDECSPEHMREMQGRIAGSRLEFFES SSHMPFIEEPARFDRVMREFLRLHDI |

TABLE 3-continued

| # Seq ID | Protein name | Sequence |
|---|---|---|
| Seq ID#7 | Rv1677 | VTHSRLIGALTVVAIIVTACGSQPKS QPAVAPTGDAAAATQVPAGQTVPAQL QFSAKTLDGHDFHGESLLGKPAVLWF WAPWCPTCQGEAPVVGQVAASHPEVT FVGVAGLDQVPAMQEFVNKYPVKTFT QLADTDGSVWANFGVTQQPAYAFVDP HGNVDVVRGRMSQDELTRRVTALTSR |

Final T-Cell Epitope Identification and Peptide Design.

The 7 protein sequences identified were screened for the identification and design of T-cell epitopes with the immunoinformatics platform NeutraCorp™ (TradeMark: BG Per. No. 85788, of Aug. 27, 2013)

Specifically, the potential high affinity T-cell epitopes (affinity equivalent to the 1% of the best bound peptides to any HLA class I and II alleles), in all the 7 proteins were identified in the protein sequences. The areas of the protein containing multiepitopic and/or HLA-promiscuous fragments were selected as potential reagents for T-cell analysis. A total of 33 peptides were designed as T-cell epitopes for class II HLA molecules (Table 4).

TABLE 4

| # Seq ID | Protein of reference | Sequence of HLA class II epitopes |
|---|---|---|
| Seq ID#8 | TBFG_13463 | AALVGYLSVPQGWT |
| Seq ID#9 | TBFG_13463 | QALGWLPMQDIDAAA |
| Seq ID#10 | TBFG_13463 | RPFMMPHTPSGGaa |
| Seq ID#11 | Mtub2_17866 | GGITWRVAATSARSA |
| Seq ID#12 | Mtub2_17866 | GHYGLATWFTRMDAMTAPT |
| Seq ID#13 | Rv0840c | VWFQRIGGGPGRPLLVVHGGPGLPH |
| Seq ID#14 | Rv0840c | HSWGGMLAQQYVLDKAPDAVS |
| Seq ID#15 | Rv0840c | VSLTIANSTASIP |
| Seq ID#16 | Rv0840c | ASLVSLKSCLDVA |
| Seq ID#17 | Rv0840c | SDFRIVGNVRDWD |
| Seq ID#18 | Rv0840c | SRLEFFESSSHMP |
| Seq ID#19 | Rv0840c | DRVMREFLRLHDI |
| Seq ID#20 | Rv3845 | MDRVRRVVTDRDSGAGA |
| Seq ID#21 | Rv3845 | PQLAAFYHRLMTTQRHC |
| Seq ID#22 | Rv3845 | ATIAVARKLAERT |
| Seq ID#23 | Rv3845 | RPYQLRDTNGDPV |
| Seq ID#24 | Rv3845 | AHYHVDTRTHPHN |
| Seq ID#25 | Rv2654c | DELVGGPPVEASAA |
| Seq ID#26 | Rv2654c | GAWRTAAVELARALVRAVAESHGV |
| Seq ID#27 | Rv2654c | AAVLFAATAAAAAA |
| Seq ID#28 | Rv1677 | SRLIGALTVVAIIVTACGSQPK |
| Seq ID#29 | Rv1677 | APVVGQVAASHPEV |
| Seq ID#30 | Rv1677 | PEVTFVGVAGLDQVP |

TABLE 4-continued

| # Seq ID | Protein of reference | Sequence of HLA class II epitopes |
|---|---|---|
| Seq ID#31 | Rv1677 | QEFVNKYPVKTFTQLADTD |
| Seq ID#32 | Rv1677 | SVWANFGVTQQPA |
| Seq ID#33 | Rv1677 | VDVVRGRMSQDELTRRVTALTSR |
| Seq ID#34 | Rv1495 | QVYRCDLGYGAKPWLIVSNNARNRHTA |
| Seq ID#35 | Rv1495 | QVYRCDLGYGAKPWLIV |
| Seq ID#36 | Rv1495 | KPWLIVSNNARNRHTA |
| Seq ID#37 | Rv1495 | ADVVAVRLTTTRRTIP |
| Seq ID#38 | Rv1495 | PTWVAMGPSDPLT |
| Seq ID#39 | Rv1495 | TGYVNADNIETLGK |
| Seq ID#40 | Rv1495 | ATMNKINTALATALGL |

A total of 47 peptides were designed as T-cell epitopes for class I HLA molecules (Table 5).

TABLE 5

| # Seq ID | Protein of reference | Sequence of HLA class II epitopes |
|---|---|---|
| Seq ID#41 | TBFG_13463 | ADTHGATSDFW |
| Seq ID#42 | TBFG_13463 | GPVAAGLGRAAL |
| Seq ID#43 | TBFG_13463 | VGYLSVPQGW |
| Seq ID#44 | TBFG_13463 | TEAEPNQALGWLPM |
| Seq ID#45 | TBFG_13463 | AEAAAQPSHALGWL |
| Seq ID#46 | TBFG_13463 | LPIEEIDAAASD |
| Seq ID#47 | TBFG_13463 | GEVSSSPQLPPRPFMM |
| Seq ID#48 | TBFG_13463 | RPFMMPHTPSGG |
| Seq ID#49 | Mtub2_17866 | STRRTCNHGGITWR |
| Seq ID#50 | Mtub2_17866 | ITWRVAATSARSAR |
| Seq ID#51 | Mtub2_17866 | ATTHPEAGHYGL |
| Seq ID#52 | Mtub2_17866 | EAGHYGLATWFTR |
| Seq ID#53 | Rv2654c | HALAARTLAAA |
| Seq ID#54 | Rv2654c | TLLAAADELV |
| Seq ID#55 | Rv2654c | AALAGDAAGAW |
| Seq ID#56 | Rv2654c | RTAAVELARALVRAV |
| Seq ID#57 | Rv2654c | AESHGVAAVLFAA |
| Seq ID#58 | Rv2654c | VLFAATAAAAVDR |
| Seq ID#59 | Rv3845 | RRTDPQLAAFYHR |
| Seq ID#60 | Rv3845 | HTQATIAVARKLAER |
| Seq ID#61 | Rv3845 | RTRVTITTGRPYQLR |
| Seq ID#62 | Rv3845 | KELIDAHYHVDTR |
| Seq ID#63 | Rv3845 | DTRTHPHNRAHT |
| Seq ID#64 | Rv3845 | RAHTDTMQNSKPAR |
| Seq ID#65 | Rv1495 | VYRCDLGYGAKPWLI |
| Seq ID#66 | Rv1495 | HTADVVAVRLTTTR |
| Seq ID#67 | Rv1495 | LTTTRRTIPTWVA |
| Seq ID#68 | Rv1495 | YLGEVTPATMNKI |
| Seq ID#69 | Rv1495 | ALATALGLPW |
| Seq ID#70 | Rv0840c | GTIAVPGGRVWFQR |
| Seq ID#71 | Rv0840c | LPHNYLAPLRR |
| Seq ID#72 | Rv0840c | NSACPSDVDLWTMNR |
| Seq ID#73 | Rv0840c | AEMATVAEALALTR |
| Seq ID#74 | Rv0840c | AEALALTRFHIFS |
| Seq ID#75 | Rv0840c | LTRFHIFSHSW |
| Seq ID#76 | Rv0840c | GMLAQQYVLDK |
| Seq ID#77 | Rv0840c | LTIANSTASIPEFSA |
| Seq ID#78 | Rv0840c | IPEFSASLVSLK |
| Seq ID#79 | Rv0840c | HSAEYQAAIRTW |
| Seq ID#80 | Rv0840c | RTWNETYLCRTRPW |
| Seq ID#81 | Rv0840c | ETYLCRTRPWPR |
| Seq ID#82 | Rv0840c | RPWPRELTEAFANM |
| Seq ID#83 | Rv0840c | TEAFANMGTEIF |
| Seq ID#84 | Rv0840c | FETMFGPSDFRI |
| Seq ID#85 | Rv0840c | LEFFESSSHMPF |
| Seq ID#86 | Rv0840c | MPFIEEPARF |
| Seq ID#87 | Rv0840c | DRVMREFLRLHDI |

Final B-Cell Epitope Identification and Peptide Design.

The 7 proteins identified were screened for the presence of linear B-cell epitopes with the developed immunoinformatics platform NeutraCorp™ (TradeMark: BG Per. No. 85788, of Aug. 27, 2013)

For continuous B-cell epitopes, protein region potentially reacting with antibodies, of 7 aminoacids in length were identified in the linear protein sequence protein. The areas of the protein sequences with hot-spot containing more than one identified fragment were considered as only one. The potential fragments for each protein were designed.

For discontinuous B-cell epitope prediction and peptide mimotopes design, we first determined by homology model the 3D structure of the 6 proteins, by using the Swiss-Prot facility. The 3D models were evaluated with the Neutracorp module of the immunoinformatics platform developed and portions of potential antigenicity identified along the 3D structure. After the identification of the different fragments composing the discontinuous B-cell epitopes the subsequent step has been the design of the peptides miming the structure of the whole B-cell epitope, also called mimotopes. To this end, for each discontinuous B-cell epitope, the manual inspection of the 3D protein structure model, allowed the spatial identification of the different linear fragments included in the epitope. The distances and the orientation of the single fragments were determined and appropriate spacers of glycine and proline were included to allow appropriate distance and angles among the different linear portions.

A total of 48 peptide epitopes and mimotopes as B-cell antigens were designed on the protein sequences and structures (Table 6)

TABLE 6

| # Seq ID | Protein of reference | Sequence of HLA class II epitopes |
|---|---|---|
| Seq ID#88 | TBFG_13463 | ANLAAGTEAEPN |
| Seq ID#89 | TBFG_13463 | AAASDDGEVSSSPQLPPRPF |
| Seq ID#90 | TBFG_13463 | AAGTEAEPNQALG |
| Seq ID#91 | TBFG_13463 | DIDAAAEAAAQPSHA |
| Seq ID#92 | TBFG_13463 | EIDAAASDDGEV |
| Seq ID#93 | TBFG_13463 | FMMPHTPSGG |
| Seq ID#94 | TBFG_13463 | GEVSSSPQLPPRPFMM |
| Seq ID#95 | TBFG_13463 | GTEAEPNQALG |
| Seq ID#96 | TBFG_13463 | GWTEANQANLA |
| Seq ID#97 | TBFG_13463 | MTINNQFDDADTHGA |
| Seq ID#98 | TBFG_13463 | SVPQGWTEANQ |
| Seq ID#99 | TBFG_13463 | TINNQFDDADTHG |
| Seq ID#100 | TBFG_13463 | WLPMQDIDAAA |
| Seq ID#101 | Mtub2_17866 | KSTRRTCNHGG |
| Seq ID#102 | Mtub2_17866 | VAATSARSARSLA |
| Seq ID#103 | Mtub2_17866 | MIDDRHKSTRRT |
| Seq ID#104 | Rv2654c | AALAGDAAGAWRT |
| Seq ID#105 | Rv3845 | AGRRTDPQLA |
| Seq ID#106 | Rv3845 | DTRTHPHNRAHTDTMQNSKPAR |
| Seq ID#107 | Rv3845 | GDPVTARGAKE |
| Seq ID#108 | Rv3845 | PLAGRRTDPQLAA |
| Seq ID#109 | Rv3845 | RDTNGDPVTARG |
| Seq ID#110 | Rv3845 | RVVTDRDSGAGAL |
| Seq ID#111 | Rv3845 | TTGRPYQLRDTNGDPVT |
| Seq ID#112 | Rv3845 | VARKLAERTRVTI |
| Seq ID#113 | Rv1495 | AMGPSDPLTGYVNADN |
| Seq ID#114 | Rv1495 | CDLGYGAKPWLIV |
| Seq ID#115 | Rv1495 | MNAPLRGQVYR |
| Seq ID#116 | Rv1495 | SNNARNRHTAD |
| Seq ID#117 | Rv1495 | LRGQVYGGEVTPATMNKINGGVSNN |
| Seq ID#118 | Rv1495 | LGYRCDLGYGAKGRLTT |
| Seq ID#119 | Rv1495 | TTTRRTIPTWVAMGPSDPLT |
| Seq ID#120 | Rv1495 | YRCDGGGDGTLGKDELGD |

TABLE 6-continued

| # Seq ID | Protein of reference | Sequence of HLA class II epitopes |
|---|---|---|
| Seq ID#121 | Rv0840c | MEGTIAVPGGRVWFQRGGGNSA |
| Seq ID#122 | Rv0840c | MQRIGGPGRGGRRLSDE |
| Seq ID#123 | Rv0840c | VSLKSCLDVATRSAIDRPEYQAAIRT |
| Seq ID#124 | Rv0840c | ETYLCRTRPWPRELTE |
| Seq ID#125 | Rv0840c | MEGTIAVPGGRVWFQRGGGNSA |
| Seq ID#126 | Rv0840c | MQRIGGPGRGGRRLSDE |
| Seq ID#127 | Rv0840c | VSLKSCLDVATRSAIDRPEYQAAIRT |
| Seq ID#128 | Rv0840c | ETYLCRTRPWPRELTE |
| Seq ID#129 | Rv0840c | DVATRSAIDRHE |
| Seq ID#130 | Rv0840c | GNVRDWDVVDR |
| Seq ID#131 | Rv0840c | GRVWFQRIGGGPGRPL |
| Seq ID#132 | Rv0840c | HMREMQGRIAGS |
| Seq ID#133 | Rv0840c | MREMQGRIAGSR |
| Seq ID#134 | Rv0840c | QLGCGNSACPSD |
| Seq ID#135 | Rv0840c | QQYVLDKAPDAVS |
| Seq ID#136 | Rv0840c | REMQGRIAGSR |

Peptide Synthesis

Chemical synthesis of the free termini peptides identified has been performed by standard Fmoc chemistry (Espikem, Prato, Italy). Peptides were produced at >90% purity.

Screening of the Bank of Synthesized Peptides with Serum Biobank, for Validation of the Antigenicity of the Selected MTB Proteins Serum bank of TB patients and controls were available to Proxagen via results of the EU regional funds for competitiveness project grant "Development of a rapid test prototype for the diagnosis of active tuberculosis" (project number BG161PO003-1.1.01-0220, of Dec. 28, 2011).

Serum samples from the following groups have been tested to confirm immunogenicity of the proteins and fragments identified:

Healthy controls (N=60)
active TB (N=50)
cured TB (N=10)

Testing of the Peptides ID#88-ID#136 by Standard Operating Procedure for the Multiple Peptide ELISA Assay.

Procedure:

a. Reagents

Sterile PBS 1×
Coating Buffer—$Na_2CO_3$/$NaHCO_3$ pH 9.3
Washing Buffer—PBS 1×
Blocking Buffer—PBS+BSA 1%
Assay Buffer—PBS+BSA 1%
Horseradish Peroxidase-Conjugated (HRP) Anti-Human IgG (Zymed)
Substrate—(0.04 mg/ml o—phenylenediamine (Sigma)
Stop Solution—1N $H_2SO_4$
Developing Buffer—UREA+$H_2O_2$ Tablet (Sigma)

b. Coating ELISA Plates:

Dilute peptides to 1 μg/ml in Coating Buffer.
Transfer 50 μl of diluted peptides per well to the ELISA plate.

Seal plate and incubate at room temperature for 1 hour and at 4° C. overnight.
c. Blocking Plate:
Add 200 µl of Blocking solution (PBS+BSA 1%) per well
Incubate at room temperature for 1 hour
Discard contents of the ELISA plate
d. ELISA Step 1: Add sample
Dilute pool sera in Assay Buffer (PBS+BSA 1%) 1:100
Transfer 50 µl of diluted sera in each ELISA plate under test as for scheme
Incubate for 2 hours at 37° C.
Wash 3 times with PBS (200 µl/well)
e. ELISA Step 2: Dilute Antibody Conjugate and Add to ELISA Plate
Dilute HRP—Anti human IgG 1:4000 in Assay Buffer (PBS+BSA 1%)
Transfer 50 µl per well to the ELISA plate using a multichannel pipette as for scheme
Incubate for 1 hour at room temperature
Wash 5 times with Wash Buffer (200 µl/well)
f. ELISA Step 3: Add Substrate and Read Plate
Prepare Developing Buffer adding 1 tablet of UREA in 20 ml of dH$_2$O
Prepare Substrate Buffer adding 1 tablet of OPD in 20 ml of Developing Buffer
Add 50 µl per well of Substrate Buffer and incubate for 15 minutes at room temperature in the dark.
Stop reaction with 50 µl of 1 N sulphuric acid.
Read absorbance using an ELISA plate reader at 492 nm.
Results:
FIG. 1 shows the results obtained with the different group sera. There are significantly higher antibody levels in active TB subjects compared to other groups when the group of epitopes from the 6 proteins are used as antigens. This demonstrates the antigenicity of these epitopes and their suitability for use in diagnostic tests.

Example 2

Extended Antigenicity Screening
To confirm the antigenicity of the B-cell epitope peptides identified by immuno-bioinformatic analysis, sera from subjects with microbiologically-confirmed active *M. tuberculosis* complex infection, subjects with IGRA-confirmed latent *M. tuberculosis* complex infection (LTBI), and healthy control subjects was screened by ELISA for the presence of antibodies directed against the peptides SEQ ID NO: 88 to SEQ ID NO: 141.
ELISA Procedure a. Reagents Sterile PBS 1—

Coating Buffer—$Na_2CO_3/NaHCO_3$ pH 9.3

Washing Buffer—PBS 1×

Blocking Buffer—PBS+BSA 1%

Assay Buffer—PBS+BSA 1%

Horseradish Peroxidase-Conjugated (HRP) Anti-Human IgG (Zymed)

Substrate—(0.04 mg/ml o-phenylenediamine (Sigma)

Stop Solution—1N $H_2SO_4$

Developing Buffer—UREA+$H_2O_2$ Tablet (Sigma)

b. Coating ELISA Plates:

Dilute peptides to 1 μg/ml in Coating Buffer.

Transfer 50 μl of diluted peptides per well to the ELISA plate.

Seal plate and incubate at room temperature for 1 hour and at 4° C. overnight.

c. Blocking Plate:

Add 200 μl of Blocking solution (PBS+BSA 1%) per well

Incubate at room temperature for 1 hour

Discard contents of the ELISA plate d. ELISA Step 1: Add Sample

Dilute pool sera in Assay Buffer (PBS+BSA 1%) 1:100

Transfer 50 μl of diluted sera in each ELISA plate under test as for scheme

Incubate for 2 hours at 37° C.

Wash 3 times with PBS (200 μl/well)

e. ELISA Step 2: Dilute Antibody Conjugate and Add to ELISA Plate

Dilute HRP-Anti human IgG 1:4000 in Assay Buffer (PBS+BSA 1%)

Transfer 50 μl per well to the ELISA plate using a multichannel pipette as for scheme Incubate for 1 hour at room temperature Wash 5 times with Wash Buffer (200 μl/well)

f. ELISA Step 3: Add Substrate and Read Plate

Prepare Developing Buffer adding 1 tablet of UREA in 20 ml of $dH_2O$

Prepare Substrate Buffer adding 1 tablet of OPD in 20 ml of Developing Buffer

Add 50 μl per well of Substrate Buffer and incubate for 15 minutes at room temperature in the dark.

Stop reaction with 50 μl of 1 N sulphuric acid.

Read absorbance using an ELISA plate reader at 492 nm.

Results

Table 21 shows the optical density (OD data) for each peptide/sera combination tested by ELISA to establish the antigenicity and preliminary sensitivity data for B-cell epitope peptides SEQ ID NO: 88 to SEQ ID NO: 141. The OD data is the absolute value of the reactivity of each single serum in duplicate for the peptide-containing (i.e. test) well minus the basal reactivity of the same serum for peptide-absent (i.e. negative control) wells.

By establishing the 99th percentile or the average+3 SD of the controls, a cut-off can be defined that gives a positive score for reactivity to each peptide across the tested sera from subjects with microbiologically-confirmed active *M. tuberculosis* complex infection (active TB sera). This allow the reactivity of active TB sera to be determined for each peptide, or for each panel of peptides derived from a single protein. In more detail:

the Mann-Whitney test p-value for TB vs controls gives the significance of the results in general terms for each peptide;

the 99th percentile cut off of the control data distribution provides a simple cut-off threshold above which an active TB sera is considered positive;

the average+3 SD cut off of the control data distribution provides a more conservative cut-off with a theoretical <1% error rate;

the N positives among the tested TB using the cut-off 99th % shows the number of positive results among the active TB sera for each peptide, according to the 99th percentile cut off;

the %-positives among TB at the cut off 99th % shows the percentage of active TB sera having a positive result according to the 99th percentile cut off;

the N positives among the tested TB using cut off Mean+3 SD shows the number of positive results among the active TB sera for each peptide, according to the average+3 SD cut off;

the %-positives among TB at the cut off Mean+3 SD shows the percentage of active TB sera having a positive result according to the average+3 SD;

the N positives >TB Average shows the number of active TB sera that have an OD that is greater than the average (mean) OD for all the active TB sera for that peptide (in essence, the top reacting sera for the peptide); and the %-positives >TB Average shows the percentage of active TB sera that have an OD that is greater than the average (mean) OD for all the active TB sera for that peptide (in essence, the top reacting sera for the peptide).

For each protein, the hypothetical performance of a panel comprising all of the peptides derived from the protein has been calculated. As this has been calculated using the average+3SD cut off and the average OD for the active TB sera (i.e. consistently positive results), the hypothetical performance for control sera is not shown.

The OD values in Table 20 show that there are significantly higher levels of antibodies to SEQ ID NO: 88 to SEQ ID NO: 141 in subjects having active *M. tuberculosis* complex infection compared to control subjects (i.e. healthy individuals or subjects having LTBI). These results confirm the antigenicity of the peptides SEQ ID NO: 88 to SEQ ID NO: 141.

Furthermore, the results demonstrate that the peptides SEQ ID NO: 88 to SEQ ID NO: 141 may be used individually or in protein panels to identify sera from subjects having active *M. tuberculosis* complex infection i.e. to diagnose active *M. tuberculosis* complex infection.

Example 3

Multiple Peptide ELISA

Diagnostic tests based on reactivity to multiple peptides are often more sensitive that tests based on reactivity to a single peptide as there may be individual variation in responsiveness due to e.g. genetic background. A pool of peptides comprising peptides screened in Example 2 was therefore screened for reactivity with a large set of control (IGRA-negative and/or IGRA positive) sera, sera from patients having active *M. tuberculosis* complex infection (Active TB) and sera from patients being cured from *M. tuberculosis* complex infection for over 24 months (Cured TB). The number of samples in each group was as follows:

Healthy controls (IGRA-negative) (N=74)
MTB infected healthy controls (LTBI, IGRA-positive and no other sign of active TB) (N=30)
active TB (N=66)
cured TB (N=10).

It was necessary to select the best performing peptides screened in Example 2 for inclusion in the peptide pool. In particular, the number of peptides that can be included in a single well of a multiple peptide ELISA is limited to around 15-20, as the inclusion of too many peptides may introduce competition for binding sites during the absorption step. Accordingly, the most reactive peptides from Example 2, and peptides providing complementary reactivity to active TB sera, were selected in order to optimize sensitivity. Specifically, the pool consisted of SEQ ID NO: 88, SEQ ID NO: 95, SEQ ID NO: 98, SEQ ID NO: 101, SEQ ID NO: 104, SEQ ID NO: 105, SEQ ID NO: 110, SEQ ID NO: 115, SEQ ID NO: 122, SEQ ID NO: 129, and SEQ ID NO: 134.

The ELISA procedure was performed in accordance with Example 2, except that the plates were coated with the peptide pool, rather than an individual peptide.

Results

Table 7 shows the optical density (OD data) for each serum tested with the peptide pool. The OD data is the absolute value of the reactivity of each single serum in duplicate for the multiple-peptide-containing (i.e. test) well minus the serum mock value.

Table 8 shows the descriptive statistics for the data contained in Table 7 descriptive various cut-offs, and the Mann-Whitney comparisons of the results. As the data set is sufficiently large, the percentages shown can be interpreted as preliminary sensitivity and specificity data.

TABLE 7

| | OD 492 nm - Absolute value (Serum pool peptides test value-Serum mock value) | | |
|---|---|---|---|
| Controls - IGRA negatives | Controls - IGRA positives | Active TB | Cured TB (>24 months) |
| 0.012 | | 0.897 | 0.033 |
| 0.028 | | 0.200 | 0.184 |
| 0.085 | | 1.748 | 0.074 |
| 0.080 | | 1.572 | 0.092 |
| 0.057 | | 0.743 | 0.066 |
| 0.073 | | 0.989 | 0.125 |
| 0.033 | | 0.712 | 0.528 |
| 0.006 | | 0.787 | 0.061 |
| 0.068 | | 0.343 | 0.027 |
| 0.038 | | 0.101 | 0.505 |
| 0.048 | | 0.086 | |
| 0.081 | | 0.169 | |
| 0.093 | | 0.113 | |
| 0.094 | | 0.303 | |
| 0.051 | | 0.682 | |
| 0.134 | | 0.699 | |
| 0.030 | | 0.712 | |
| 0.077 | | 0.405 | |
| 0.039 | | 0.069 | |
| 0.066 | | 0.703 | |
| 0.084 | | 0.739 | |
| 0.059 | | 1.297 | |
| 0.080 | | 0.873 | |
| 0.075 | | 0.732 | |
| 0.026 | | 0.048 | |
| 0.070 | | 0.490 | |
| 0.041 | | 0.244 | |
| 0.063 | | 0.357 | |
| 0.049 | | 0.362 | |
| 0.064 | | 0.093 | |
| 0.025 | | 0.540 | |
| 0.000 | | 0.605 | |
| 0.060 | | 0.489 | |
| 0.030 | | 0.740 | |
| 0.040 | | 0.076 | |
| 0.073 | | 0.182 | |
| 0.084 | | 0.662 | |
| 0.085 | | 0.536 | |
| 0.043 | | 0.501 | |
| 0.124 | | 0.238 | |
| 0.022 | | 0.158 | |
| 0.069 | | 1.845 | |
| 0.031 | | 0.895 | |
| 0.057 | | 0.292 | |
| 0.075 | | 0.625 | |
| 0.051 | | 0.527 | |
| 0.071 | | 1.662 | |
| 0.067 | | 0.913 | |
| 0.018 | | 0.042 | |
| 0.061 | | 0.699 | |
| 0.033 | | | |
| 0.055 | | | |
| 0.105 | | | |
| 0.106 | | | |
| 0.059 | | | |
| 0.148 | | | |
| 0.036 | | | |
| 0.087 | | | |
| 0.046 | | | |

TABLE 7-continued

OD 492 nm - Absolute value
(Serum pool peptides test value-Serum mock value)

| Controls - IGRA negatives | Controls - IGRA positives | Active TB | Cured TB (>24 months) |
|---|---|---|---|
| 0.075 | | | |
| 0.088 | 0.105 | 0.267 | |
| 0.035 | 0.067 | 0.098 | |
| 0.048 | 0.124 | 0.587 | |
| 0.079 | 0.148 | 0.696 | |
| 0.074 | 0.047 | 0.198 | |
| 0.104 | 0.068 | 0.066 | |
| 0.065 | 0.131 | 0.138 | |
| 0.094 | 0.057 | 0.235 | |
| 0.067 | 0.038 | 0.959 | |
| 0.037 | 0.069 | 0.635 | |
| 0.087 | 0.151 | 0.102 | |
| 0.091 | 0.089 | 0.207 | |
| 0.108 | 0.105 | 0.087 | |
| 0.044 | 0.124 | 0.178 | |
| | 0.054 | 0.501 | |
| | 0.039 | 0.055 | |
| | 0.005 | | |
| | 0.078 | | |
| | 0.167 | | |
| | 0.157 | | |
| | 0.068 | | |
| | 0.076 | | |
| | 0.089 | | |
| | 0.098 | | |
| | 0.086 | | |
| | 0.124 | | |
| | 0.109 | | |
| | 0.086 | | |
| | 0.068 | | |
| | 0.084 | | |

TABLE 8

| | Controls - IGRA negatives | Controls - IGRA positives | Active TB | Cured TB (>24 months) |
|---|---|---|---|---|
| N | 74 | 30 | 66 | 10 |
| Average | 0.063 | 0.090 | 0.523 | 0.170 |
| Median | 0.065 | 0.086 | 0.496 | 0.083 |
| SD | 0.029142772 | 0.038559836 | 0.425356087 | 0.188509505 |
| 95-percentile | 0.1067 | 0.1543 | 1.50325 | 0.51765 |
| 99th-percentile | 0.13778 | 0.1641 | 1.78195 | 0.52593 |
| Average + 3SD | 0.150414804 | 0.206046173 | | |
| N positives >95th percentile IGRAneg | 4 | 9 | 54 | 4 |
| N positives >99th percentile IGRAneg | 1 | 4 | 53 | 3 |
| N positives >Mean + 3SD IGRAneg | 0 | 3 | 52 | 3 |
| N positives >95th percentile IGRApos | 0 | 2 | 52 | 3 |
| N positives >99th percentile IGRApos | 0 | 1 | 51 | 3 |
| N positives >Mean + 3SD IGRApos | 0 | 0 | 46 | 2 |
| % positives >95th percentile IGRAneg | 5.41% | 30.00% | 81.82% | 40.00% |
| % positives >99th percentile IGRAneg | 1.35% | 13.33% | 80.30% | 30.00% |
| % positives >Mean + 3SD IGRAneg | 0.00% | 10.00% | 78.79% | 30.00% |
| % positives >95th percentile IGRApos | 0.00% | 6.67% | 78.79% | 30.00% |
| % positives >99th percentile IGRApos | 0.00% | 3.33% | 77.27% | 30.00% |
| % positives >Mean + 3SD IGRApos | 0.00% | 0.00% | 69.70% | 20.00% |

Example 4

Identification of Candidate T-Cell Antigens

1. Introduction

This study was an early feasibility study designed to identify potential new antigens for the T-SPOT.TB assay and to calculate if they could replace the ESAT-6 and CFP10 antigens or be additive to the assay and increase the sensitivity of the current T-SPOT®.TB assay. In order to achieve this a set of new TB antigens were screened in the T-SPOT®. TB assay with 87 TB confirmed donors and 96 healthy donors.

2. Methods

Peripheral blood mononuclear cells (PBMCs) isolated from TB confirmed (confirmed by GeneXpert® MTB/RIF assay) and healthy donors were tested in the T-SPOT.TB assay with T-SPOT.TB Panel A (PA), T-SPOT.TB Panel B (PB) and 24 alternative TB antigens. GeneXpert® MTB/RIF assay is a nucleic acid amplification test for tuberculosis, manufactured by Cepheid. It is backed by the World Health Organisation for use in TB endemic countries, and has a claimed sensitivity of 92.2% in culture confirmed TB donors (675/732) and a specificity of 99.2% in donors with no TB (604/609), Boehme, C. (2011).

The antigens tested are listed in Table 9.

TABLE 9

| Antigen | No. of peptides |
|---|---|
| T-SPOT. TB Panel A | — |
| T-SPOT. TB Panel B | — |
| Massi pool CD4+8 | 91 |
| CD4/CD8 epitope pool TBFG__13463 | 15 |
| CD4/CD8 epitope pool Mtub2__17866 | 7 |
| CD4/CD8 epitope pool Rv2654c | 11 |
| CD4/CD8 epitope pool Rv3845 | 15 |
| CD4/CD8 epitope pool Rv1495 | 12 |
| CD4/CD8 epitope pool Rv0840c | 25 |
| CD4/CD8 epitope pool Rv1677 | 6 |
| Rv2654c peptide library | 18 |
| TBFG__13463 peptide library | 30 |
| Rv0840c peptide library | 69 |
| Rv3845 peptide library | 27 |
| Rv1677 peptide library | 43 |
| Rv1495 peptide library | 24 |
| Mtub2__17866 peptide library | 12 |

The CD4/CD8 epitopes in each epitope pool are listed in Tables 10 to 16.

TABLE 10

CD4/CD8 epitope pool TBFG_13643

| | |
|---|---|
| SEQ ID NO: 8 | AALVGYLSVPQGWT |
| SEQ ID NO: 9 | QALGWLPMQDIDAAA |
| SEQ ID NO: 10 | RPFMMPHTPSGGAA |
| SEQ ID NO: 158 | DTHGATSDFW |
| SEQ ID NO: 142 | HGATSDFW |
| SEQ ID NO: 42 | GPVAAGLGRAAL |
| SEQ ID NO: 43 | VGYLSVPQGW |
| SEQ ID NO: 44 | TEAEPNQALGWLPM |
| SEQ ID NO: 143 | EPNQALGWLPM |
| SEQ ID NO: 45 | AEAAAQPSHALGWL |
| SEQ ID NO: 46 | LPIEEIDAAASD |
| SEQ ID NO: 159 | GEVSSSPQLPPRPF |
| SEQ ID NO: 144 | SSSPQLPPRPFMM |
| SEQ ID NO: 160 | RPFMMPHTPSG |
| SEQ ID NO: 93 | FMMPHTPSGG |

TABLE 11

CD4/CD8 epitope pool Mtub2_17866

| | |
|---|---|
| SEQ ID NO: 11 | GGITWRVAATSARSA |
| SEQ ID NO: 12 | GHYGLATWFTRMDAMTAPT |
| SEQ ID NO: 49 | STRRTCNHGGITWR |
| SEQ ID NO: 50 | ITWRVAATSARSAR |
| SEQ ID NO: 51 | ATTHPEAGHYGL |
| SEQ ID NO: 161 | EAGHYGLATWF |
| SEQ ID NO: 146 | HYGLATWFTR |

TABLE 12

CD4/CD8 epitope pool Rv2654c

| | |
|---|---|
| SEQ ID NO: 25 | DELVGGPPVEASAA |
| SEQ ID NO: 26 | GAWRTAAVELARALVRAVAESHGV |
| SEQ ID NO: 147 | ELARALVRAV |
| SEQ ID NO: 27 | AAVLFAATAAAAAA |
| SEQ ID NO: 53 | HALAARTLAAA |
| SEQ ID NO: 54 | TLLAAADELV |
| SEQ ID NO: 55 | AALAGDAAGAW |
| SEQ ID NO: 162 | RTAAVELARALV |
| SEQ ID NO: 57 | AESHGVAAVLFAA |
| SEQ ID NO: 163 | VLFAATAAAAAV |
| SEQ ID NO: 148 | ATAAAAAVDR |

TABLE 13

CD4/CD8 epitope pool Rv3845

| | |
|---|---|
| SEQ ID NO: 20 | MDRVRRVVTDRDSGAGA |
| SEQ ID NO: 21 | PQLAAFYHRLMTTQRHC |
| SEQ ID NO: 22 | ATIAVARKLAERT |
| SEQ ID NO: 23 | RPYQLRDTNGDPV |
| SEQ ID NO: 24 | AHYHVDTRTHPHN |
| SEQ ID NO: 59 | RRTDPQLAAFYHR |
| SEQ ID NO: 149 | QLAAFYHRL |
| SEQ ID NO: 164 | HTQATIAVARK |
| SEQ ID NO: 150 | ATIAVARKLAER |
| SEQ ID NO: 165 | RTRVTITTGRPY |
| SEQ ID NO: 151 | TITTGRPYQLR |
| SEQ ID NO: 62 | KELIDAHYHVDTR |
| SEQ ID NO: 63 | DTRTHPHNRAHT |
| SEQ ID NO: 166 | RAHTDTMQNSK |
| SEQ ID NO: 152 | TMQNSKPAR |

TABLE 14

CD4/CD8 epitope pool Rv1495

| | |
|---|---|
| SEQ ID NO: 34 | QVYRCDLGYGAKPWLIVSNNARNRHTA |
| SEQ ID NO: 35 | QVYRCDLGYGAKPWLIV |
| SEQ ID NO: 153 | DLGYGAKPWLI |
| SEQ ID NO: 36 | KPWLIVSNNARNRHTA |
| SEQ ID NO: 37 | ADVVAVRLTTTRRTIP |
| SEQ ID NO: 38 | PTWVAMGPSDPLT |
| SEQ ID NO: 39 | TGYVNADNIETLGK |
| SEQ ID NO: 40 | ATMNKINTALATALGL |
| SEQ ID NO: 167 | VYRCDLGYGAKPW |
| SEQ ID NO: 67 | LTTTRRTIPTWVA |
| SEQ ID NO: 68 | YLGEVTPATMNKI |
| SEQ ID NO: 69 | ALATALGLPW |

TABLE 15

CD4/CD8 epitope pool Rv0840c

| | |
|---|---|
| SEQ ID NO: 13 | VWFQRIGGGPGRPLLWHGGPGLPH |
| SEQ ID NO: 14 | HSWGGMLAQQYVLDKAPDAVS |
| SEQ ID NO: 15 | VSLTIANSTASIP |
| SEQ ID NO: 16 | ASLVSLKSCLDVA |

TABLE 15-continued

CD4/CD8 epitope pool Rv0840c

| | | |
|---|---|---|
| SEQ ID NO: | 17 | SDFRIVGNVRDWD |
| SEQ ID NO: | 18 | SRLEFFESSSIIMP |
| SEQ ID NO: | 19 | DRVMREFLRLHDI |
| SEQ ID NO: | 70 | GTIAVPGGRVWFQR |
| SEQ ID NO: | 154 | GGRVWFQR |
| SEQ ID NO: | 170 | NSACPSDVDLWTM |
| SEQ ID NO: | 155 | DVDLWTMNR |
| SEQ ID NO: | 168 | AEMATVAEALAL |
| SEQ ID NO: | 156 | TVAEALALTR |
| SEQ ID NO: | 75 | LTRFHIFSHSW |
| SEQ ID NO: | 76 | GMLAQQYVLDK |
| SEQ ID NO: | 169 | LTIANSTASIPEF |
| SEQ ID NO: | 157 | STASIPEFSA |
| SEQ ID NO: | 79 | HSAEYQAAIRTW |
| SEQ ID NO: | 80 | RTWNETYLCRTPW |
| SEQ ID NO: | 81 | ETYLCRTRPWPR |
| SEQ ID NO: | 171 | RPWPRELTEAFAN |
| SEQ ID NO: | 83 | TEAFANMGTEIF |
| SEQ ID NO: | 85 | LEFFESSSHMPF |
| SEQ ID NO: | 86 | MPFIEEPARF |
| SEQ ID NO: | 87 | DRVMREFLRLHDI |

TABLE 16

CD4/CD8 epitope pool Rv1677

| | | |
|---|---|---|
| SEQ ID NO: | 28 | SRLIGALTVVAIIVTACGSQPK |
| SEQ ID NO: | 29 | APVVGQVAASHPEV |
| SEQ ID NO: | 30 | PEVTFVGVAGLDQVP |
| SEQ ID NO: | 31 | QEFVNKYPVKTFTQLADTD |
| SEQ ID NO: | 32 | SVWANFGVTQQPA |
| SEQ ID NO: | 33 | VDVVRGRMSQDELTRRVTALTSR |

Massi pool CD4+8 contains of all the CD4/CD8 epitopes used in CD4/CD8 epitope pools for TBFG_13463, Mtub2_17866, Rv2654c, Rv3845, Rv1495, Rv0840c and Rv1677. The peptide library pools for TBFG_13463, Mtub2_17866, Rv2654c, Rv3845, Rv1495, Rv0840c and Rv1677 contain 15mers having an 11 amino acid overlap and covering the entire amino acid sequence of the proteins used in the epitope selection.

3. Results 3.1 Donors 3.1.1 TB Positive Donors 120 donors were tested in the T-SPOT assay at the University of Cape Town. TB infection status was confirmed by GeneXpert MTB/RIF assay. 93 of 120 donors were GeneXpert positive (8/120 GeneXpert negative and 19/120 GeneXpert not tested). Of the 93 GeneXpert Positive donors, 4/93 donors had low cells counts (<2.0×10$^6$ cells/mL) and 2/93 donors had high negative controls (>10 spots). These donors were therefore excluded. The remaining 87 TB positive donors were used for the present example.

3.1.2 Healthy Donors 107 healthy donors were tested in the T-SPOT assay at Oxford Immunotec UK. 11 donors were excluded from this group due to an increased risk of TB infection (8 donors were excluded due to origin of birth in a TB endemic region or time spent abroad in TB endemic regions, 1 donor was excluded due to close contact with a TB infected individual and 2 donors were excluded due to previous history of positive responses in the T-SPOT.TB assay). The remaining 96 donors were included in the analysis.

Due to shortages of antigens not all of the 96 donors were tested with all 17 antigens. The numbers tested with each antigen are listed in Table 17.

TABLE 17

| Antigen | Number of healthy donors tested |
|---|---|
| Panel A | 96 |
| Panel B | 96 |
| Massi pool CD4+8 | 96 |
| CD4/CD8 epitope pool TBFG_13463 | 92 |
| TBFG_13463 peptide library | 80 |
| CD4/CD8 epitope pool Mtub2_17866 | 94 |
| Mtub2_17866 library | 95 |
| CD4/CD8 epitope pool Rv2654c | 96 |
| Rv2654c peptide library | 95 |
| CD4/CD8 epitope pool Rv3845 | 95 |
| Rv3845 library | 93 |
| CD4/CD8 epitope pool Rv1495 | 94 |
| Rv1495 library | 96 |
| CD4/CD8 epitope pool Rv0840c | 93 |
| Rv0840c peptide library | 93 |
| CD4/CD8 epitope pool Rv1677 | 93 |
| Rv1677 library | 96 |

3.2 Receiver Operating Characteristic (ROC) Curves

Data was analysed using GraphPad Prism 6 software. Normalised spot counts from healthy donors were plotted as the control values. Normalised spot counts from TB confirmed donors were plotted as the patient values.

The current T-SPOT.TB assay utilises the max spot count from Panel A or Panel B as the assay readout, for example: Donor 1, Panel A=4 spots, Panel B=10 spots, the T-SPOT.TB test result therefore=10 spots. This analysis has been applied to calculate the assay performance when using different antigen combinations. Its use is denoted by the term Max following listed antigens.

3.3 Statistical Analysis

ROC curves have been compared using MedCalc software. The Hanley and McNeil method, (Hanley, J, McNeil B J. (1983)) has been used to compare the difference in the area under curve (AUC) between curves derived from the same group of patients ($p<0.05$=significant difference between curves).

3.4 T-SPOT.TB Assay Performance

A ROC curve of the current T-SPOT.TB assay performance is shown in FIG. 2A. Assay sensitivity and specificity at different cut-offs are shown for Panel A/Panel B max in FIG. 2B. The T-SPOT.TB assay performance in this study was 94.2% sensitivity and 97.9% specificity at a 6 spot cut off. These performance figures are similar to the performance previously published in the U.S.A T-SPOT.TB assay package insert (sensitivity=95.6% (175/183), specificity=97.1% (297/306), PI-TB-US-V4, March 2013). 2/96 healthy donors tested positive with the Panel A/Panel B antigens, these donors are scheduled for re-testing in the T-SPOT.TB assay to confirm this result. Reduction of the cut-off to 3 spots would not affect the sensitivity, but would have reduced the specificity of the assay to 87.5%.

3.5 Comparison of CD4/CD8 Selected Epitopes Vs Peptide Libraries Covering Whole Protein Sequence In this arm of the study, peptide sequences identified in silico as being potential CD4/CD8 epitopes from the Mtb genome were synthesised, and pooled according to the Mb protein from which they were derived. Concurrently to this, copies of the Mtb protein sequences were obtained and peptide libraries (15mers with an 11 amino acid overlap) were synthesised and pooled for each protein. Both of these sets of peptide pools were tested in the T-SPOT.TB assay in comparison to Panel A and Panel B. The results are shown in FIGS. 3 and 4.

Figure 3A:
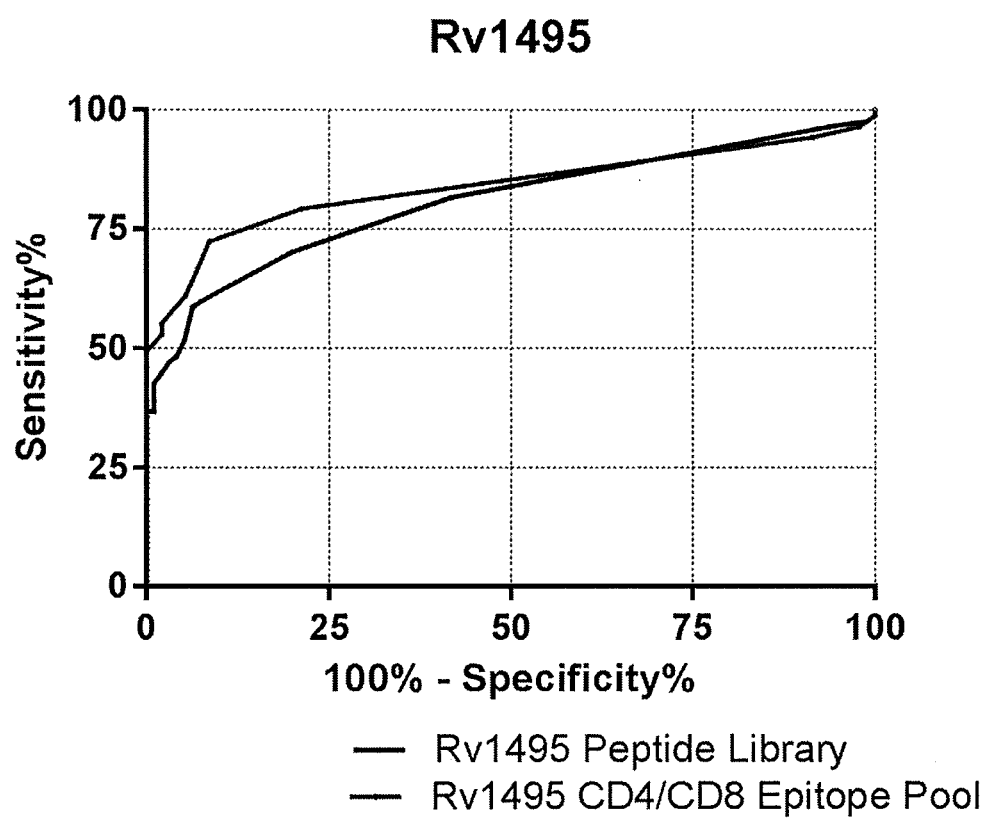
FIG. 3 shows a comparison of CD4/CD8 epitopes pools and the corresponding peptide libraries in the T-SPOT assay. A—Rv1495, B—TBFG 13463, C—Rv3845 (87 TB Positive donors).
Figure 3B:
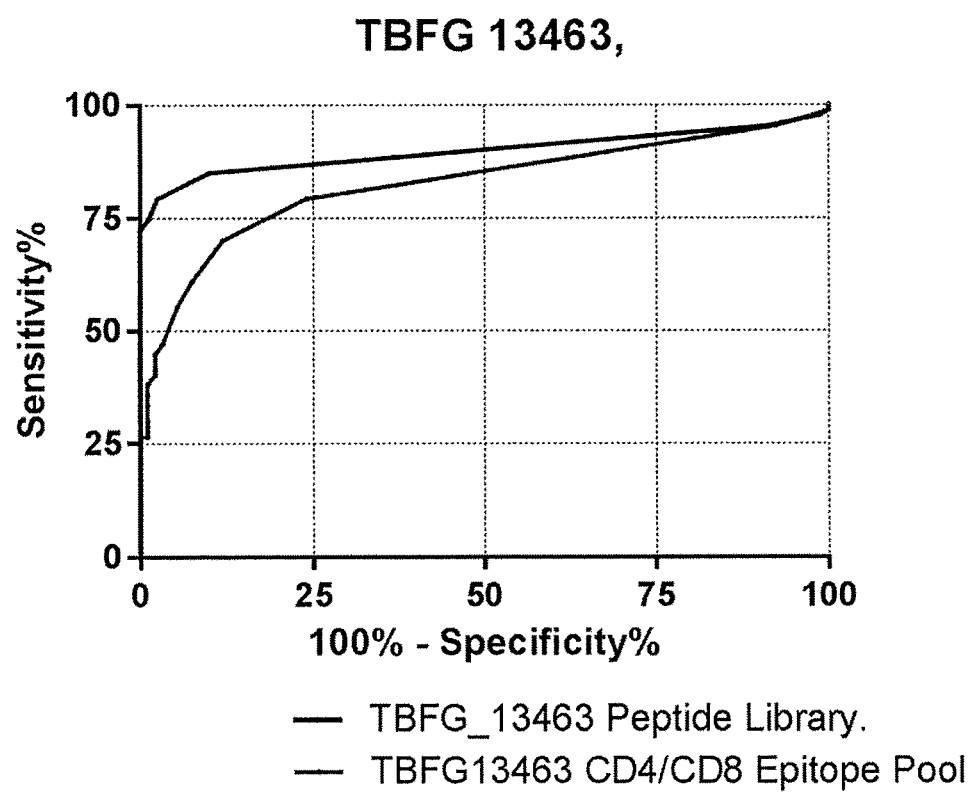
Figure 3C:
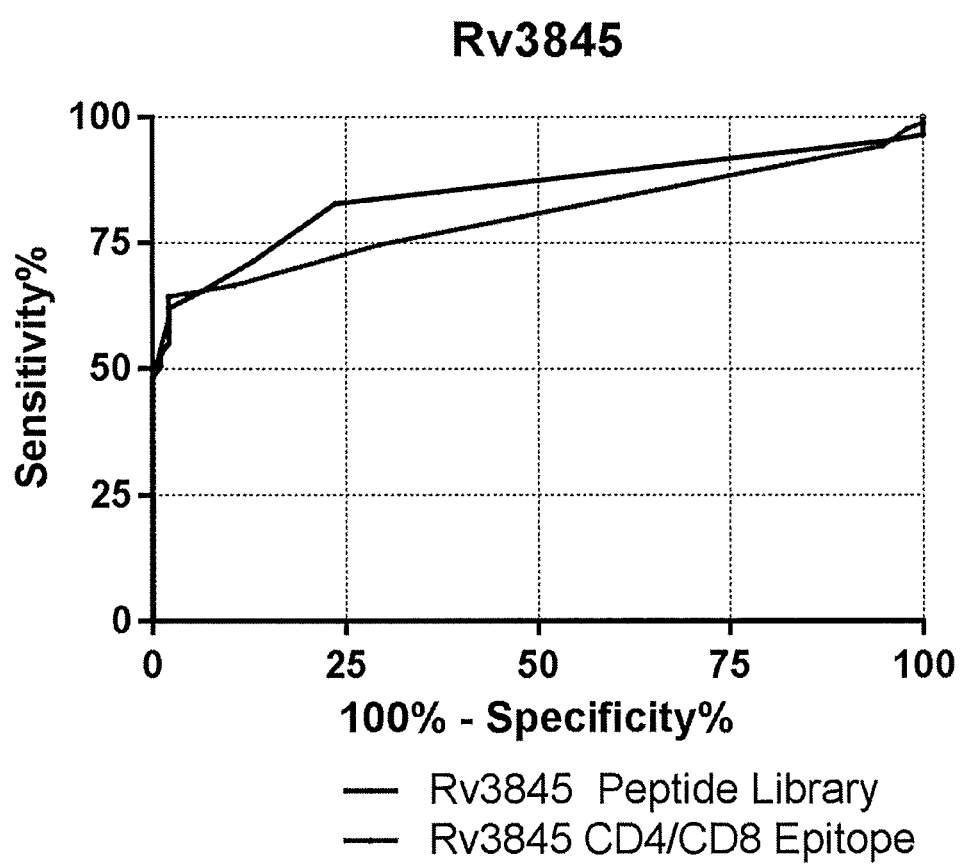
Figure 4A:
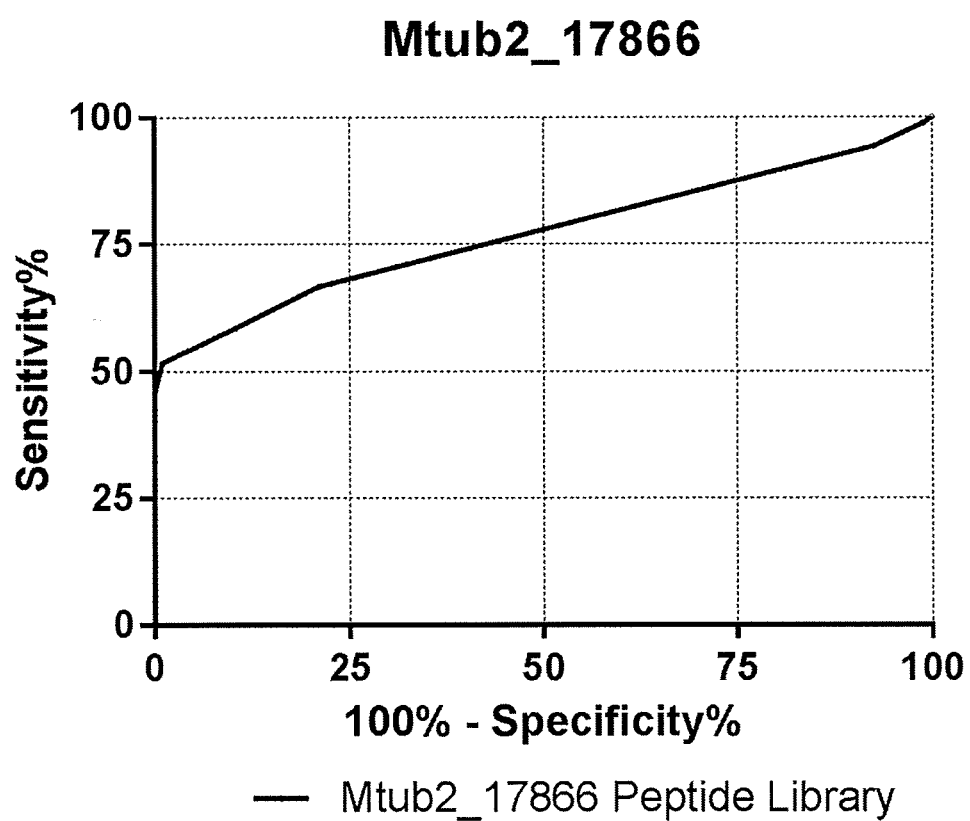
FIG. 4 shows the performance of peptide libraries in the T-SPOT.TB assay. A—Mtub2_17866, B—Rv2654c, C—Rv1677, D—Rv0840c. (87 TB Positive donors).
Figure 4B:
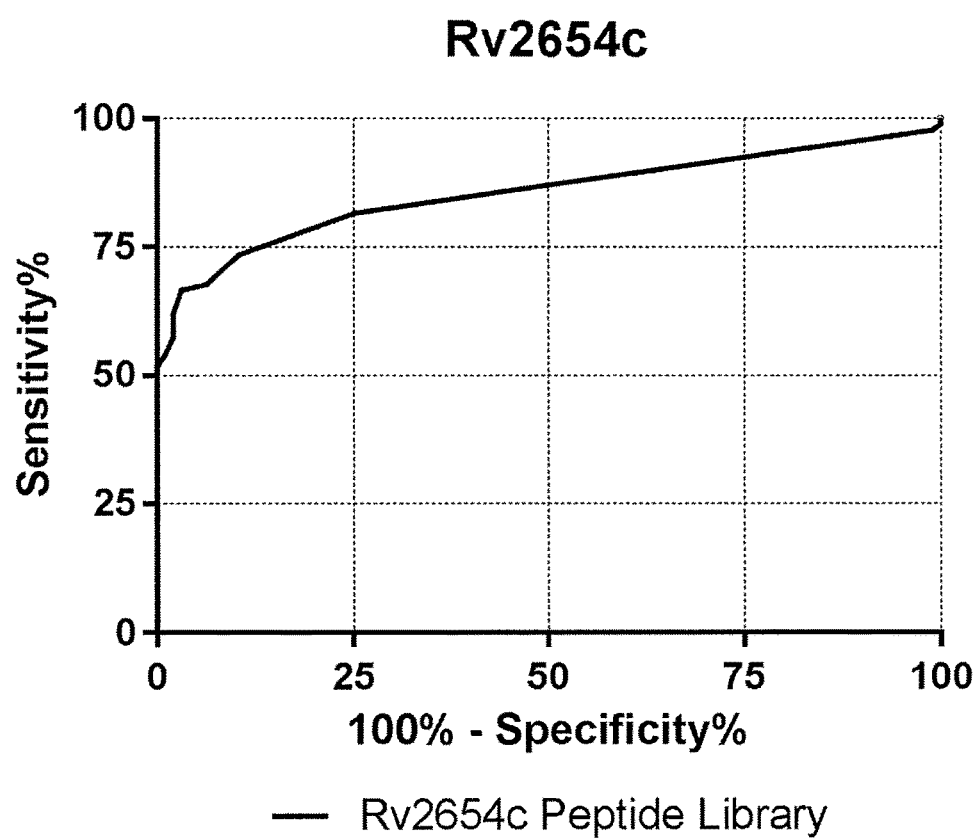
Figure 4C:
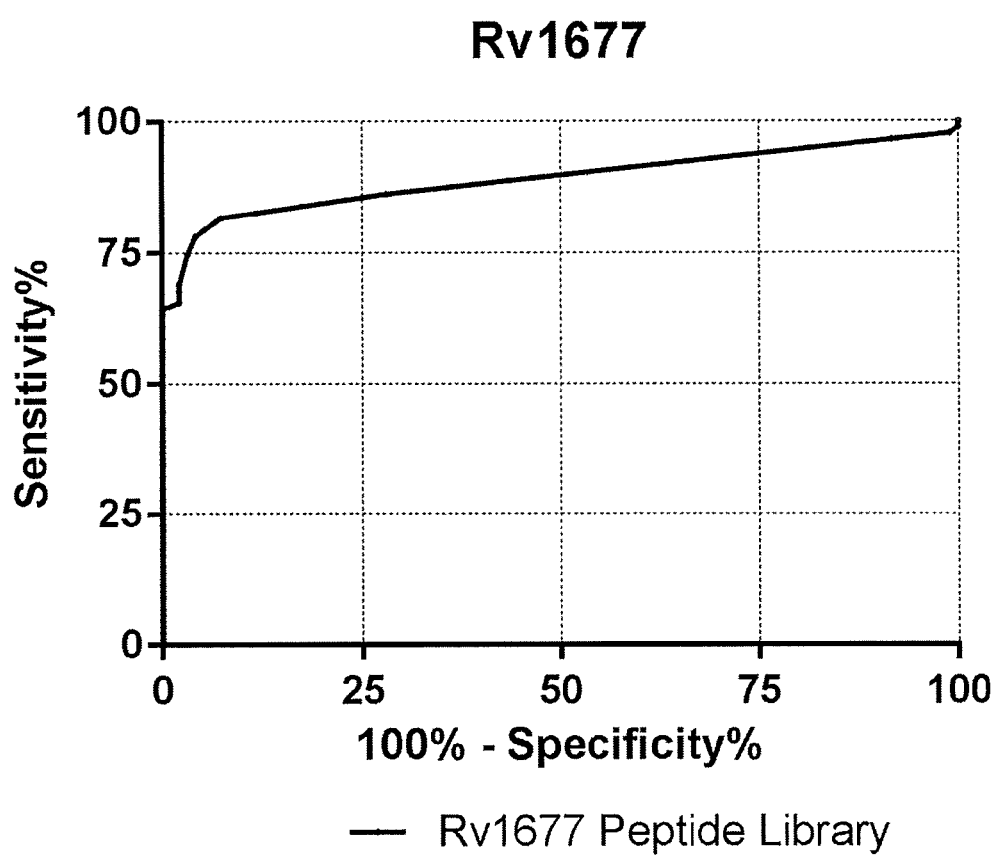
Figure 4D:
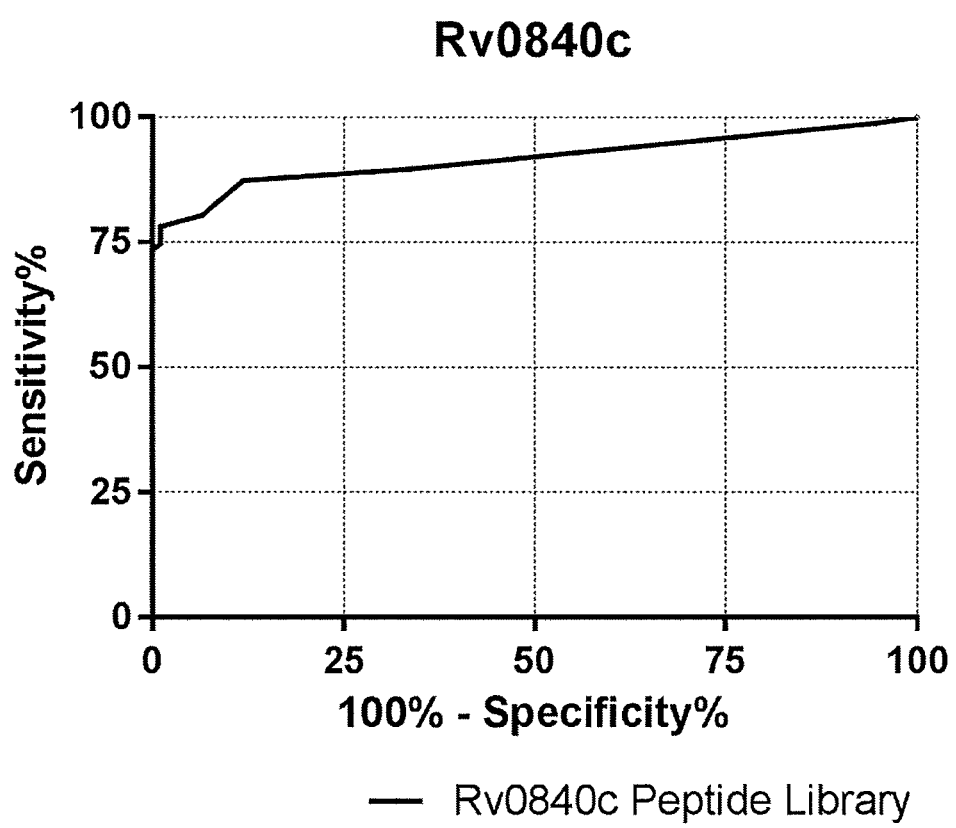

FIG. 3 compares the CD4/CD8 epitopes pool vs the peptide library for Rv1495, TBFG_13463 and Rv3845.

Statistical comparison of the ROC curves shows there was a significant difference in performance between the CD4/CD8 epitope pool and the corresponding peptide library in A (p=0.0267). In this case, the peptide library outperformed its corresponding CD4/CD8 epitope pool. In B and C, there was no significant difference in performance between the CD4/CD8 epitope pool and its corresponding protein library (0.3208 and p=0.1850 respectively).

FIG. 4 shows ROC curves for peptide library for Mtub2_17866, Rv2654c, Rv1677 and Rv0840C peptide libraries. Table 18 shows the sensitivity and specificity of Rv0840c in the T-SPOT.TB using different cut offs (n=180; TB Positive=87; Healthy Donors=93).

TABLE 18

| Cut off | Sensitivity % | 95% CI | Specificity % | 95% CI | Likelihood ratio |
|---|---|---|---|---|---|
| >0.5000 | 89.66 | 81.27% to 95.16% | 66.67 | 56.13% to 76.11% | 2.690 |
| >1.500 | 87.36 | 78.50% to 93.52% | 88.17 | 79.82% to 93.95% | 7.386 |
| >2.500 | 80.46 | 70.57% to 88.19% | 93.55 | 86.48% to 97.60% | 12.47 |
| >3.500 | 78.16 | 68.02% to 86.31% | 98.92 | 94.15% to 99.97% | 72.69 |
| >4.500 | 74.71 | 64.25% to 83.42% | 98.92 | 94.15% to 99.97% | 69.48 |
| >5.500 | 73.56 | 63.02% to 82.45% | 100.0 | 96.11% to 100.0% | |
| >6.500 | 72.41 | 61.79% to 81.46% | 100.0 | 96.11% to 100.0% | |
| >7.500 | 65.52 | 54.56% to 75.39% | 100.0 | 96.11% to 100.0% | |
| >8.500 | 63.22 | 52.20% to 73.31% | 100.0 | 96.11% to 100.0% | |
| >9.500 | 60.92 | 49.87% to 71.21% | 100.0 | 96.11% to 100.0% | |

Table 19 summarises the individual sensitivities and specificities of the TBFG_13463, Mtub2_17866, Rv2654c, Rv3845, Rv1495, Rv0840c and Rv1677 CD4/CD8 epitope pools and peptide libraries, and the Massi pool CD4+8, using a 6-spot cut off.

TABLE 19

| | 6 Spot cut off | |
|---|---|---|
| Antigen | Sensitivity | Specificity |
| Massi pool CD4+8 | 57.47 (50/87) | 95.77 (93/96) |
| CD4/CD8 epitope pool TBFG_13463 | 44.8 (39/87) | 97.9 (90/92) |
| TBFG_13463 peptide library | 67.8 (59/87) | 100 (80/80) |
| CD4/CD8 epitope pool Mtub2_17866 | 28.7 (25/87) | 98.9 (93/94) |
| Mtub2_17866 library | 42.5 (37/87) | 100 (95/95) |
| CD4/CD8 epitope pool Rv2654c | 31.03 (27/87) | 100 (96/96) |
| Rv2654c peptide library | 58.6 (51/87) | 97.9 (93/95) |
| CD4/CD8 epitope pool Rv3845 | 44.8 (39/87) | 100 (95/95) |
| Rv3845 library | 55.2 (48/87) | 97.8 (91/93) |
| CD4/CD8 epitope pool Rv1495 | 49.4 (43/87) | 100 (94/94) |
| Rv1495 library | 48.3 (42/87) | 95.8 (92/96) |
| CD4/CD8 epitope pool Rv0840c | 8 (7/87) | 100 (93/93) |
| Rv0840c peptide library | 73.6 (64/87) | 100 (93/93) |
| CD4/CD8 epitope pool Rv1677 | 29.9 (26/87) | 100 (93/93) |
| Rv1677 library | 67.8 (59/87) | 97.8 (94/96) |

Figure 5:
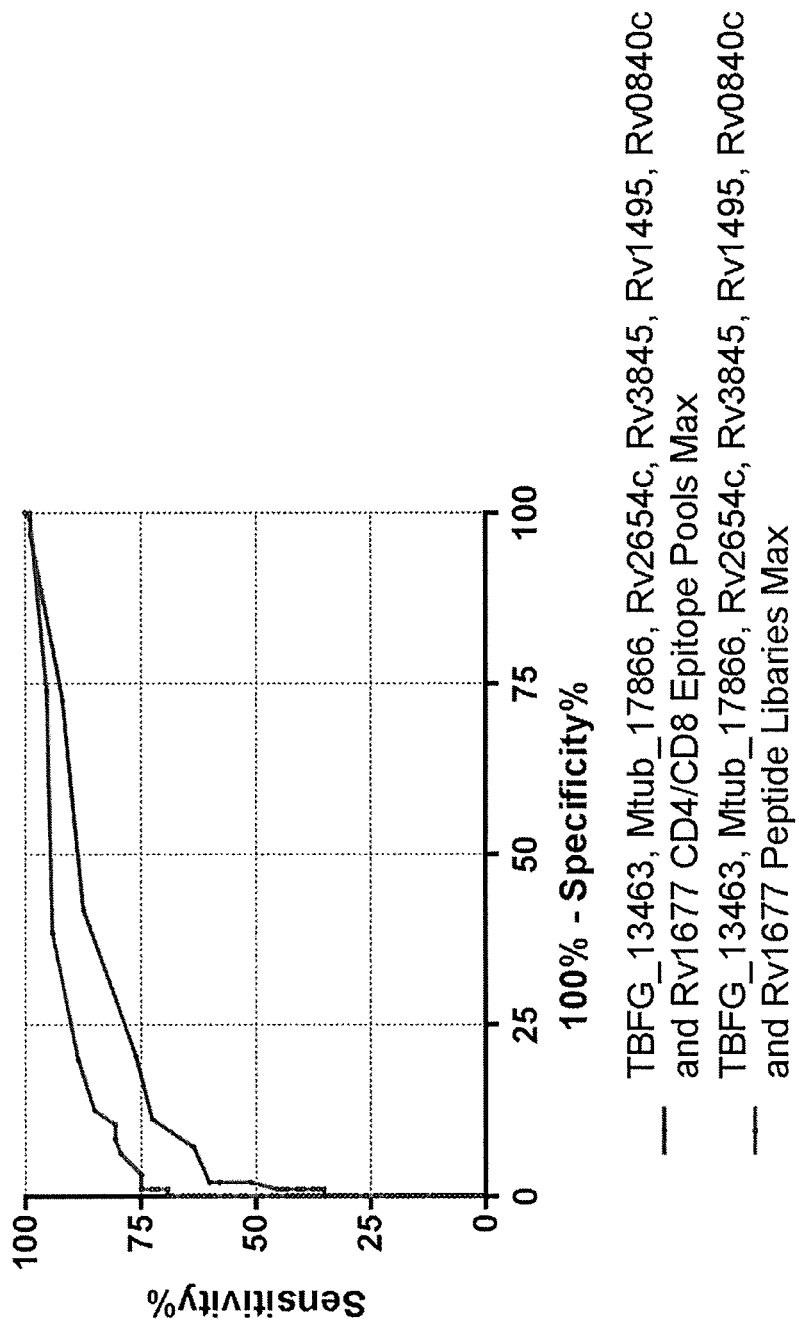
FIG. 5 shows a comparison of the TBFG_13463, Mtub2_17866, Rv2654c, Rv3845, Rv1495, Rv0840c and Rv1677 CD4/CD8 epitope pools max and the TBFG_13463, Mtub2_17866, Rv2654c, Rv3845, Rv1495, Rv0840c and Rv1677 peptide libraries max (n=183; TB Pos=87).

FIG. 5 shows a comparison of the TBFG_13463, Mtub2_17866, Rv2654c, Rv3845, Rv1495, Rv0840c and Rv1677 CD4/CD8 epitope pools max and the TBFG_13463, Mtub2_17866, Rv2654c, Rv3845, Rv1495, Rv0840c and Rv1677 peptide libraries max. In accordance with the definition of "max" above, each epitope pool and peptide library was tested individually in the T-SPOT.TB assay. There was a significant difference between the CD4/CD8 epitope pools max and the peptide libraries max (p=0.0033).

Figure 6:
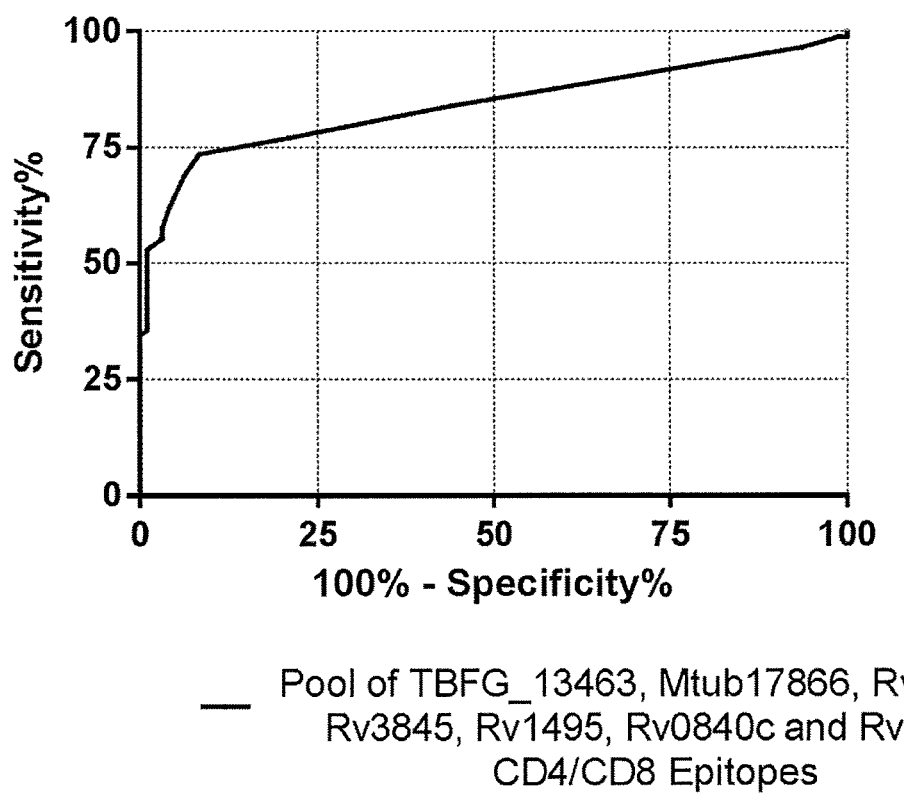
FIG. 6 shows the ROC curve for a T-SPOT.TB assay using a combined epitope pool comprising all of the CD4/CD8 epitope pools (TBFG_13463, Mtub2_17866, Rv2654c, Rv3845, Rv1495, Rv0840c and Rv1677).

FIG. 6 shows the results of a single, combined epitope pool comprising all of the CD4/CD8 epitope pools (TBFG_13463, Mtub2_17866, Rv2654c, Rv3845, Rv1495, Rv0840c and Rv1677).

3.6 Replacing Either Panel A (ESAT-6) or Panel B (CFP10)

Figure 7:
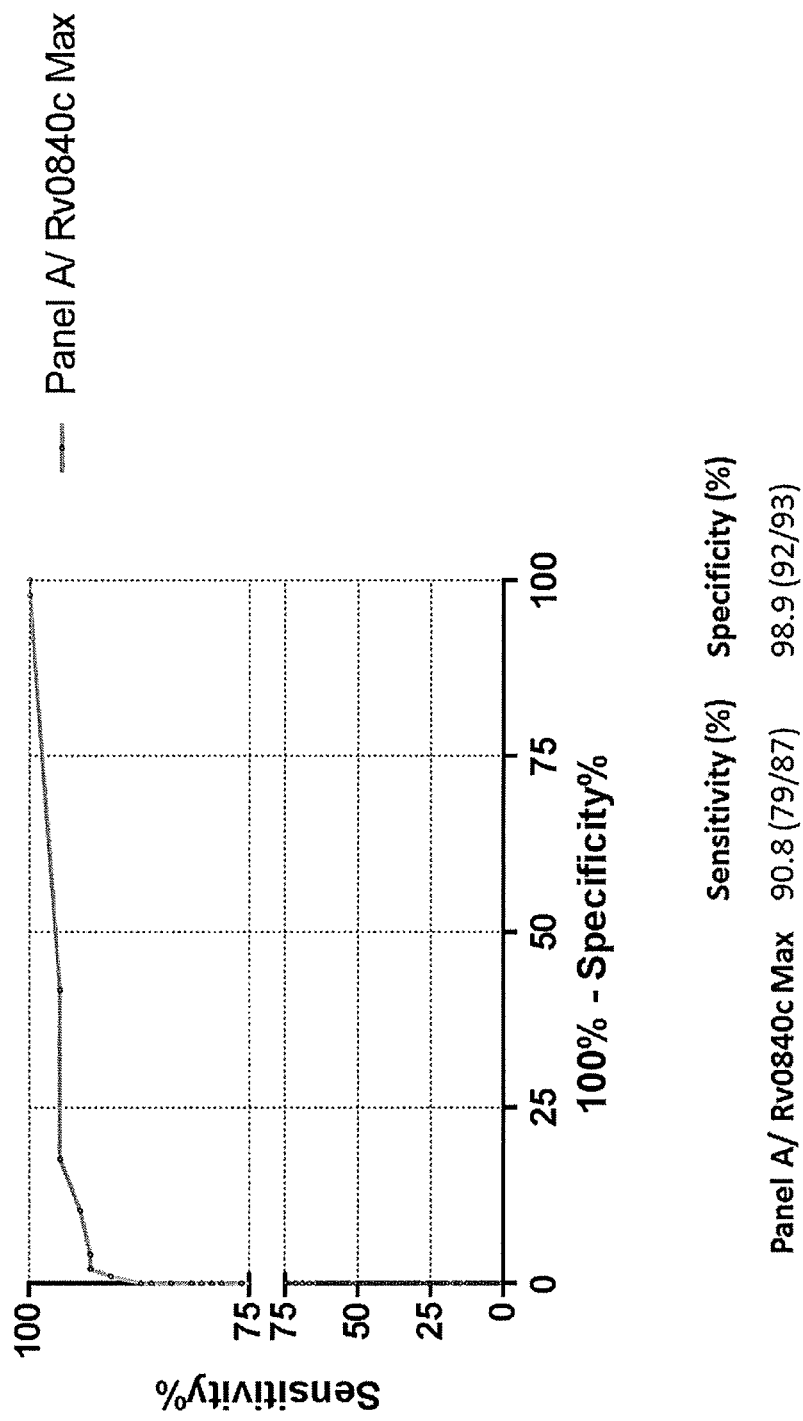
FIG. 7 shows the replacement of ESAT-6 with the Rv0840c peptide library (n=183; 87 TB Positive).
Figure 8:
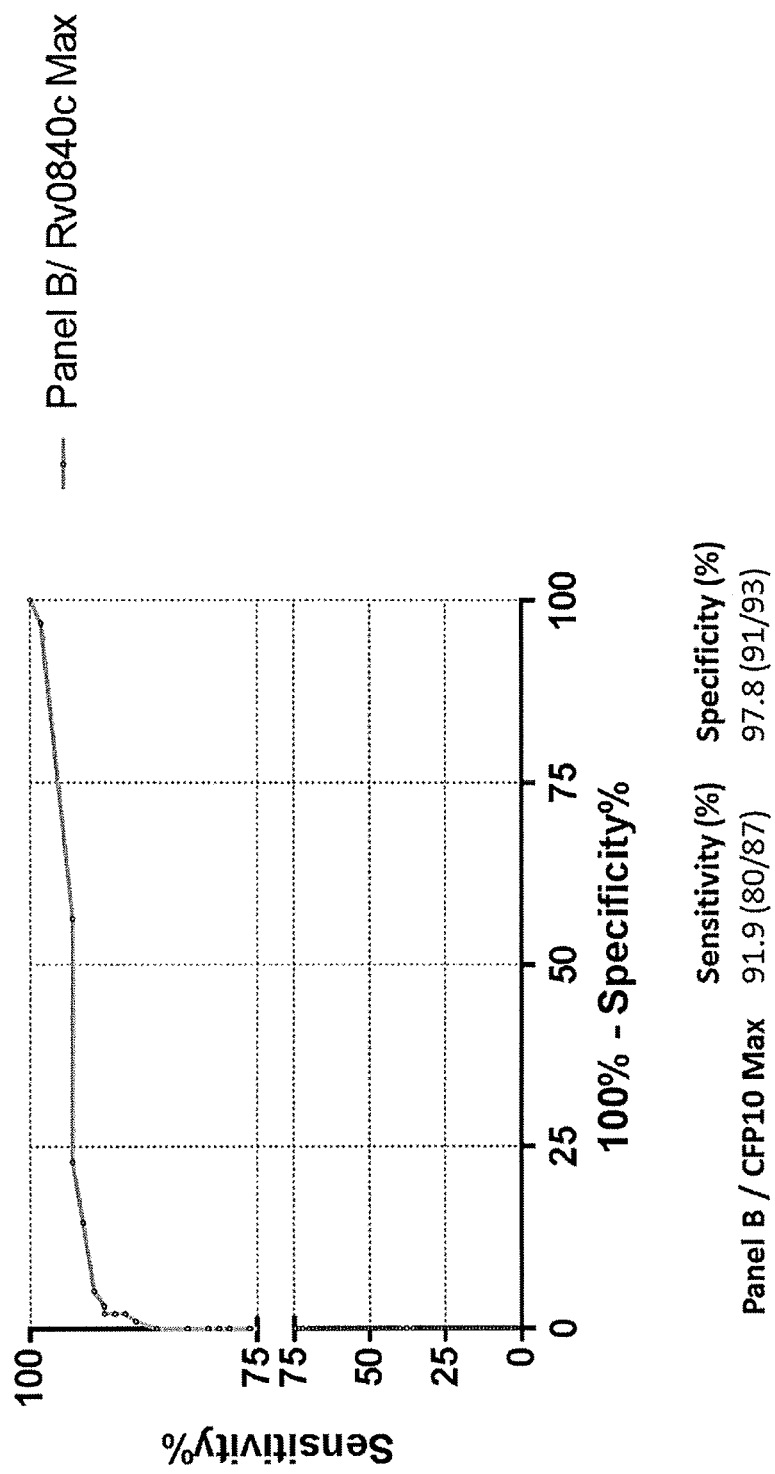
FIG. 8 shows the replacement of CPF10 with the Rv0840c peptide library (n=183; 87 TB Positive).

One of the major questions posed at the beginning of the study asked if one of the ESAT-6 (Panel A) or CFP10 (Panel B) pools currently used in the T-SPOT.TB assay could be replaced without impacting on the performance of the assay. In this analysis, ESAT-6 and CFP10 have been replaced with the Rv0840c peptide library, and the results plotted as ROC curves. FIG. 7 shows the results for replacing ESAT-6. FIG. 8 shows the results for replacing CFP10. It can be seen that sensitivity and specificity is high when ESAT-6 or CFP10 is replaced with the Rv0840c peptide library.

Figure 9:
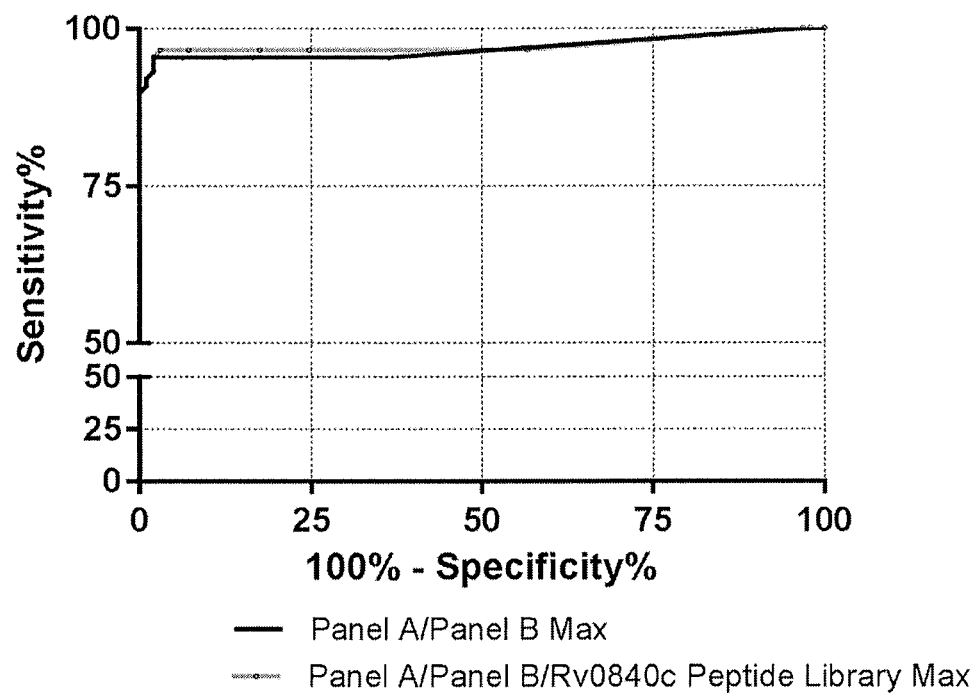
FIG. 9 shows the addition of Rv0840c to Panel A and Panel B in the T-SPOT.TB assay. More specifically.

3.7 Addition of Antigens to the Current T-SPOT.TB Assay to Increase Assay Sensitivity The final question posed at the beginning of this study was to determine if the addition of an antigen to the current T-SPOT.TB assay could increase the sensitivity of the T-SPOT.TB assay. Using the data generated in the study and the "max" analysis mentioned above, the results of addition of peptide libraries to the T-SPOT.TB assay have been determined. FIG. 9 shows a comparison of the ROC curves for Panel A/Panel B max and Panel A/Panel B/Rv0840c peptide library max. Table 20 summarises the sensitivity and specificity of the Panel A/Panel B max and the Panel A/Panel B/Rv084c peptide library max.

TABLE 20

Addition of Rv0840c to Panel A and Panel B in the T-SPOT.TB assay using the Max analysis.

| | | | | 6 spot cut off | |
|---|---|---|---|---|---|
| | | | | Sensitivity (%) | Specificity (%) |
| Panel A | Panel B | | MAX | 94.2 (82/87) | 97.9 (94/96) |
| Panel A | Panel B | Rv0840c | | 96.5 (84/87) | 97.8 (91/93) |

Inclusion of Rv0840c in the T-SPOT.TB assay resulted in detection of 2 further TB confirmed donors that the current T-SPOT.TB assay would not have detected. Inclusion of Rv0840c increased the sensitivity of the T-SPOT.TB assay to 96.5% (84/87).

4. Conclusion

This study was an early feasibility study designed to identify potential candidate antigens to replace the ESAT-6 and CFP10 antigens in the T-SPOT.TB assay and/or to increase the sensitivity of the current T-SPOT.TB assay. 87 TB positive donors and up to 96 healthy donors were tested in the in the T-SPOT.TB assay with Panel A, Panel B, TBFG 13463, Mtub2_17866, Rv2654c, Rv3845, Rv1495, Rv0840c and Rv1677 CD4/CD8 epitope pools, and TBFG_13463, Mtub2_17866, Rv2654c, Rv3845, Rv1495, Rv0840c and Rv1677 peptide libraries.

Both the peptide libraries and the CD4/CD8 epitope pools achieve good specificity in the T-SPOT.TB assay. In some instances, the peptide libraries (15mers/11 amino acid overlap) outperformed the corresponding CD4/CD8 epitope pool. The results show that the Rv0840c peptide library in particular is a promising candidate for increasing the sensitivity of the current T-SPOT.TB assay or replacing either ESAT-6 or CF

TABLE 21

| # Seq ID | Protein of reference | Peptide Sequence | Epitipe Type | Active TB sera (microbiologically confirmed) | | | | | | | | | | | AVG | MEDIAN |
|---|---|---|---|---|---|---|---|---|---|---|---|---|---|---|---|---|
| | | | | TB-RM013 | TB-RM021 | TB-RM022 | TB-RM023 | TB-RM027 | TB-RM030 | TB-RM033 | TB-RM034 | TB-RM035 | TB-RM037 | TB-S014 | | |
| Seq ID#88 | TBFG_13463 | ANLAAGTEAEPN | Continuous | 0.401 | 0.252 | 0.184 | 0.299 | 1.271 | 0.288 | 0.334 | 0.444 | 0.423 | 0.450 | 0.145 | 0.408 | 0.334 |
| Seq ID#89 | TBFG_13463 | AAASDDGEVSSSPQLPRPF | Continuous | 0.045 | 0.040 | 0.045 | 0.031 | 0.025 | 0.058 | 0.066 | 0.148 | 0.077 | 0.093 | 0.073 | 0.064 | 0.058 |
| Seq ID#90 | TBFG_13463 | AAGTEAEPNQALG | Continuous | 0.091 | 0.056 | 0.067 | 0.045 | 0.141 | 0.112 | 0.125 | 0.141 | 0.140 | 0.209 | 0.035 | 0.105 | 0.112 |
| Seq ID#91 | TBFG_13463 | DIDAAAEAAAQPSHA | Continuous | 0.037 | 0.005 | 0.044 | 0.033 | 0.352 | 0.032 | 0.057 | 0.052 | 0.079 | 0.063 | 0.033 | 0.071 | 0.044 |
| Seq ID#92 | TBFG_13463 | EIDAAASDDGEV | Continuous | 0.276 | 0.014 | 0.060 | 0.045 | 0.090 | 0.053 | 0.067 | 0.103 | 0.106 | 0.091 | 0.048 | 0.086 | 0.067 |
| Seq ID#93 | TBFG_13463 | FMMPHTPSGG | Continuous | 0.039 | 0.011 | 0.061 | 0.036 | 0.074 | 0.060 | 0.064 | 0.048 | 0.102 | 0.026 | 0.028 | 0.050 | 0.048 |
| Seq ID#94 | TBFG_13463 | GEVSSSPQLPPRPFMM | Continuous | 0.066 | 0.019 | 0.173 | 0.049 | 0.114 | 0.075 | 0.148 | 0.107 | 0.093 | 0.160 | 0.042 | 0.095 | 0.093 |
| Seq ID#95 | TBFG_13463 | GTEAEPNQALG | Continuous | 0.173 | 0.147 | 0.106 | 0.244 | 0.111 | 0.080 | 0.133 | 0.241 | 0.139 | 0.283 | 0.347 | 0.182 | 0.147 |
| Seq ID#96 | TBFG_13463 | GWTEANQNALA | Continuous | 0.101 | 0.044 | 0.089 | 0.058 | 0.087 | 0.088 | 0.144 | 0.098 | 0.130 | 0.245 | 0.042 | 0.102 | 0.089 |
| Seq ID#97 | TBFG_13463 | MTINNQFDDADTHGA | Continuous | 0.053 | 0.031 | 0.064 | 0.046 | 0.064 | 0.069 | 0.081 | 0.077 | 0.108 | 0.154 | 0.030 | 0.070 | 0.064 |
| Seq ID#98 | TBFG_13463 | SVPQGWTEANQ | Continuous | 0.248 | 0.225 | 0.152 | 0.139 | 0.177 | 0.108 | 0.138 | 0.169 | 0.180 | 0.334 | 0.533 | 0.218 | 0.177 |
| Seq ID#99 | TBFG_13463 | TINNQFDDADTHG | Continuous | 0.284 | 0.048 | 0.075 | 0.057 | 0.088 | 0.070 | 0.087 | 0.112 | 0.111 | 0.234 | 0.138 | 0.118 | 0.088 |
| Seq ID#100 | TBFG_13463 | WLPMQDIDAAA | Continuous | 0.078 | 0.038 | 0.090 | 0.065 | 0.100 | 0.082 | 0.154 | 0.131 | 0.121 | 0.226 | 0.044 | 0.102 | 0.090 |
| Seq ID#101 | Mtub2_17866 | KSTRRTCNHGG | Continuous | 0.186 | 0.102 | 0.089 | 0.056 | 0.217 | 0.069 | 0.098 | 0.097 | 0.104 | 0.161 | 0.102 | 0.116 | 0.102 |
| Seq ID#102 | Mtub2_17866 | VAATSARSARSLA | Continuous | 0.098 | 0.165 | 0.067 | 0.052 | 0.070 | 0.054 | 0.083 | 0.083 | 0.065 | 0.162 | 0.039 | 0.085 | 0.070 |
| Seq ID#103 | Mtub2_17866 | MIDDRHKSTRRT | Continuous | 0.095 | 0.062 | 0.063 | 0.073 | 0.070 | 0.047 | 0.179 | 0.185 | 0.087 | 0.141 | 0.056 | 0.096 | 0.073 |
| Seq ID#104 | Rv2654c | AALAGDAAGAWRT | Continuous | 0.117 | 0.082 | 0.128 | 0.103 | 0.227 | 0.082 | 0.079 | 0.150 | 0.123 | 0.211 | 0.248 | 0.141 | 0.123 |
| Seq ID#105 | Rv3845 | AGRRTDPQLA | Continuous | 0.162 | 0.285 | 0.065 | 0.052 | 0.209 | 0.081 | 0.165 | 0.127 | 0.144 | 0.182 | 0.188 | 0.151 | 0.162 |
| Seq ID#106 | Rv3845 | DTRTHPHNRAHTDTMQNSKPAR | Continuous | 0.043 | 0.027 | 0.059 | 0.040 | 0.089 | 0.055 | 0.055 | 0.074 | 0.097 | 0.123 | 0.025 | 0.062 | 0.055 |
| Seq ID#107 | Rv3845 | GDPVTARGAKE | Continuous | 0.072 | 0.037 | 0.069 | 0.043 | 0.082 | 0.067 | 0.107 | 0.098 | 0.107 | 0.184 | 0.047 | 0.083 | 0.072 |
| Seq ID#108 | Rv3845 | PLAGRRTDPQLAA | Continuous | 0.053 | 0.032 | 0.077 | 0.059 | 0.098 | 0.076 | 0.144 | 0.118 | 0.112 | 0.198 | 0.040 | 0.091 | 0.077 |
| Seq ID#109 | Rv3845 | RDTNGDPVTARG | Continuous | 0.129 | 0.050 | 0.188 | 0.048 | 0.103 | 0.084 | 0.138 | 0.163 | 0.160 | 0.209 | 0.038 | 0.119 | 0.129 |

TABLE 21-continued

| Seq ID | Gene | Sequence | Type | | | | | | | | | | | | |
|---|---|---|---|---|---|---|---|---|---|---|---|---|---|---|---|
| Seq ID#110 | Rv3845 | RVVTDRDSGAGAL | Continuous | 0.059 | 0.110 | 0.134 | 0.259 | 0.095 | 0.184 | 0.273 | 0.150 | 0.300 | 0.054 | 0.156 | 0.134 |
| Seq ID#111 | Rv3845 | TTGRPYQDPVT | Continuous | 0.033 | 0.058 | 0.034 | 0.090 | 0.058 | 0.097 | 0.084 | 0.076 | 0.128 | 0.029 | 0.067 | 0.058 |
| Seq ID#112 | Rv3845 | VARKLAERTRVTI | Continuous | 0.037 | 0.044 | 0.029 | 0.073 | 0.040 | 0.060 | 0.066 | 0.090 | 0.090 | 0.028 | 0.053 | 0.044 |
| Seq ID#113 | Rv1495 | AMGPSDPLTGYVNADN | Continuous | 0.060 | 0.087 | 0.054 | 0.116 | 0.090 | 0.131 | 0.097 | 0.110 | 0.178 | 0.040 | 0.095 | 0.090 |
| Seq ID#114 | Rv1495 | CDLGYGAKPWLIV | Continuous | 0.000 | 0.048 | 0.031 | 0.065 | 0.031 | 0.062 | 0.050 | 0.083 | 0.045 | 0.000 | 0.041 | 0.045 |
| Seq ID#115 | Rv1495 | MNAPLRGQVYR | Continuous | 0.000 | 0.177 | 0.104 | 0.105 | 0.254 | 0.095 | 0.083 | 0.093 | 0.084 | 0.239 | 0.116 | 0.095 |
| Seq ID#116 | Rv1495 | SNNARNRHTAD | Continuous | 0.023 | 0.074 | 0.051 | 0.129 | 0.066 | 0.129 | 0.095 | 0.122 | 0.153 | 0.038 | 0.087 | 0.076 |
| Seq ID#117 | Rv1495 | LRGQVYGGEVTPATMNKINGGVSN N | Discontinuous | 0.025 | 0.070 | 0.045 | 0.213 | 0.070 | 0.081 | 0.085 | 0.134 | 0.095 | 0.028 | 0.094 | 0.081 |
| Seq ID#118 | Rv1495 | LGYRCDLGYGAKGRLT T | Discontinuous | 0.022 | 0.037 | 0.031 | 0.085 | 0.065 | 0.051 | 0.075 | 0.118 | 0.045 | 0.013 | 0.053 | 0.045 |
| Seq ID#119 | Rv1495 | TTTRRTIPTWVAMGPSDPLT | Discontinuous | 0.091 | 0.051 | 0.052 | 0.123 | 0.073 | 0.219 | 0.072 | 0.120 | 0.166 | 0.061 | 0.100 | 0.073 |
| Seq ID#120 | Rv1495 | YRCDGGGDGTLGKDELGD | Discontinuous | 0.070 | 0.041 | 0.043 | 0.109 | 0.068 | 0.051 | 0.084 | 0.112 | 0.077 | 0.027 | 0.065 | 0.068 |
| Seq ID#121 | Rv0840c | MEGTIAVPGGRVWFQRGGGNSA | Discontinuous | 0.014 | 0.056 | 0.031 | 0.195 | 0.058 | 0.057 | 0.061 | 0.068 | 0.028 | 0.045 | 0.058 | 0.056 |
| Seq ID#122 | Rv0840c | MQRIGGPGRGGRRLSDE | Discontinuous | 0.120 | 0.101 | 0.050 | 0.164 | 0.166 | 0.153 | 0.086 | 0.279 | 0.224 | 0.228 | 0.157 | 0.162 |
| Seq ID#123 | Rv0840c | VSLKSCLDVATRSAIDRPEYQAAIRT | Discontinuous | 0.036 | 0.037 | 0.032 | 0.131 | 0.870 | 0.061 | 0.065 | 0.092 | 0.037 | 0.011 | 0.131 | 0.061 |
| Seq ID#124 | Rv0840c | ETYLCRTRPWPRELTE | Discontinuous | 0.167 | 0.081 | 0.024 | 0.080 | 0.020 | 0.045 | 0.552 | 0.058 | 0.133 | 0.019 | 0.110 | 0.058 |
| Seq ID#125 | Rv0840c | MEGTIAVPGGRVWFQRGGGNSA | Discontinuous | Repeat Seq ID#121 | | | | | | | | | | | |
| Seq ID#126 | Rv0840c | MQRIGGPGRGGRRLSDE | Discontinuous | Repeat Seq ID#122 | | | | | | | | | | | |
| Seq ID#127 | Rv0840c | VSLKSCLDVATRSAIDRPEYQAAIRT | Discontinuous | Repeat Seq ID#123 | | | | | | | | | | | |
| Seq ID#128 | Rv0840c | ETYLCRTRPWPRELTE | Discontinuous | Repeat Seq ID#124 | 0.569 | | | | | | | | | | |
| Seq ID#129 | Rv0840c | DVATRSAIDRHE | Continuous | 0.073 | 0.085 | 0.176 | 0.185 | 0.099 | 0.095 | 0.143 | 0.119 | 0.127 | 0.055 | 0.157 | 0.119 |

TABLE 21-continued

| # Seq ID | Seq | Sequence | Stand Dev | Mann-Whitney test p-value vs controls | N positives cut-off 99th% | N positives cut off Mean + 3SD | %-positives cut off 99th% | %-positives cut off Mean + 3SD | N >TB Average | %->TB Average | CTR-RM001 | CTR-RM002 | CTR-RM003 | CTR-RM004 | CTR-RM005 | CTR-RM006 | CTR-RM007 | CTR-RM008 |
|---|---|---|---|---|---|---|---|---|---|---|---|---|---|---|---|---|---|---|
| Seq ID#130 | Rv0840c | GNVRDMDV VDR | | | | 0.092 | 0.061 | 0.066 | 0.057 | 0.137 | 0.067 | 0.136 | 0.083 | 0.149 | 0.042 | 0.092 | 0.083 |
| Seq ID#131 | Rv0840c | GRVWFQRI GGGPGRPL | | | | 0.067 | 0.070 | 0.052 | 0.042 | 0.052 | 0.045 | 0.044 | 0.097 | 0.115 | 0.019 | 0.063 | 0.052 |
| Seq ID#132 | Rv0840c | HMREMQGR IAGS | | | | 0.043 | 0.020 | 0.033 | 0.039 | 0.124 | 0.058 | 0.087 | 0.097 | 0.093 | 0.068 | 0.273 | 0.084 | 0.068 |
| Seq ID#133 | Rv0840c | MREMQGRI AGSR | | | | 0.053 | 0.023 | 0.084 | 0.189 | 0.142 | 0.079 | 0.131 | 0.090 | 0.082 | 0.146 | 0.034 | 0.103 | 0.090 |
| Seq ID#134 | Rv0840c | QLGCGNSA CPSD | | | | 0.130 | 0.065 | 0.093 | 0.066 | 0.173 | 0.123 | 0.128 | 0.129 | 0.161 | 0.239 | 0.114 | 0.126 | 0.128 |
| Seq ID#135 | Rv0840c | QQYVLDKA PDAVS | | | | 0.188 | 0.042 | 0.086 | 0.081 | 0.126 | 0.082 | 0.138 | 0.072 | 0.134 | 0.195 | 0.035 | 0.105 | 0.086 |
| Seq ID#136 | Rv0840c | REMQGRIA GSR | | | | 0.078 | 0.037 | 0.091 | 0.221 | 0.170 | 0.139 | 0.145 | 0.113 | 0.108 | 0.134 | 0.046 | 0.118 | 0.126 |
| Seq ID#137 | Rv1677 | TACGSQPK SQPAVAPT | | | | 0.234 | 0.040 | 0.058 | 0.052 | 0.219 | 0.047 | 0.107 | 0.120 | 0.126 | 0.105 | 0.055 | 0.112 | 0.105 |
| Seq ID#138 | Rv1677 | TQVPAGQT VPAQIQFS AK | | | | 0.063 | 0.036 | 0.037 | 0.033 | 0.067 | 0.081 | 0.077 | 0.065 | 0.201 | 0.191 | 0.020 | 0.068 | 0.065 |
| Seq ID#139 | Rv1677 | SAKTLDGH DFHGES | | | | 0.051 | 0.039 | 0.063 | 0.037 | 0.058 | 0.030 | 0.097 | 0.082 | 0.079 | 0.106 | 0.049 | 0.062 | 0.058 |
| Seq ID#140 | Rv1677 | MQEFVNKY PVKTFTQ | | | | 0.035 | 0.003 | 0.057 | 0.039 | 0.082 | 0.041 | 0.170 | 0.139 | 0.067 | 0.070 | 0.034 | 0.067 | 0.057 |
| Seq ID#141 | Rv1677 | NFGVTQQP AYAFVDPH GNVDV | | | | 0.053 | 0.016 | 0.090 | 0.060 | 0.148 | 0.081 | 0.121 | 0.109 | 0.122 | 0.102 | 0.053 | 0.087 | 0.090 |

TB sera — Control sera-IGRA negative

| # Seq ID | | | | | | | | | | | | | | | | | | |
|---|---|---|---|---|---|---|---|---|---|---|---|---|---|---|---|---|---|---|
| Seq ID#88 | | | 0.304 | 0.00003 | 9 | 8 | 81.82% | 72.73% | 4 | 36.36% | 0.098 | 0.115 | 0.135 | 0.120 | 0.045 | 0.064 | 0.071 | 0.081 |
| Seq ID#89 | | | 0.035 | 0.00150 | 4 | 2 | 36.36% | 18.18% | 5 | 45.45% | 0.041 | 0.029 | 0.021 | 0.023 | 0.010 | 0.000 | 0.039 | 0.017 |
| Seq ID#90 | | | 0.053 | 0.00055 | 7 | 6 | 63.64% | 54.55% | 6 | 54.55% | 0.014 | 0.047 | 0.053 | 0.011 | 0.030 | 0.005 | 0.047 | 0.021 |
| Seq ID#91 | | | 0.095 | 0.07773 | 2 | 1 | 18.18% | 9.09% | 2 | 18.18% | 0.058 | 0.043 | 0.027 | 0.042 | 0.019 | 0.000 | 0.016 | 0.025 |
| Seq ID#92 | | | 0.069 | 0.04558 | 3 | 1 | 27.27% | 9.09% | 5 | 45.45% | 0.052 | 0.047 | 0.041 | 0.070 | 0.021 | 0.023 | 0.023 | 0.048 |
| Seq ID#93 | | | 0.026 | 0.11506 | 1 | 1 | 9.09% | 9.09% | 5 | 45.45% | 0.033 | 0.036 | 0.030 | 0.037 | 0.021 | 0.004 | 0.007 | 0.045 |
| Seq ID#94 | | | 0.051 | 0.00551 | 6 | 5 | 54.55% | 45.45% | 5 | 45.45% | 0.039 | 0.054 | 0.054 | 0.045 | 0.025 | 0.030 | 0.000 | 0.049 |
| Seq ID#95 | | | 0.085 | 0.00001 | 11 | 10 | 100.00% | 90.91% | 4 | 36.36% | 0.048 | 0.043 | 0.055 | 0.069 | 0.035 | 0.020 | 0.000 | 0.009 |

TABLE 21-continued

| Seq ID | | | | | | | | | | | | | | | | |
|---|---|---|---|---|---|---|---|---|---|---|---|---|---|---|---|---|
| Seq ID#96 | 0.057 | 0.00065 | 8 | 5 | 72.73% | 45.45% | 3 | 27.27% | 0.061 | 0.046 | 0.052 | 0.044 | 0.021 | 0.007 | 0.000 | 0.055 |
| Seq ID#97 | 0.036 | 0.00683 | 5 | 2 | 45.45% | 18.18% | 4 | 36.36% | 0.067 | 0.049 | 0.041 | 0.063 | 0.016 | 0.002 | 0.000 | 0.045 |
| Seq ID#98 | 0.122 | 0.00001 | 11 | 10 | 100.00% | 90.91% | 4 | 36.36% | 0.048 | 0.009 | 0.010 | 0.019 | 0.039 | 0.015 | 0.018 | 0.033 |
| Seq ID#99 | 0.075 | 0.00003 | 9 | 7 | 81.82% | 63.64% | 3 | 27.27% | 0.036 | 0.039 | 0.041 | 0.007 | 0.024 | 0.013 | 0.038 | 0.033 |
| Seq ID#100 | 0.054 | 0.00022 | 9 | 6 | 81.82% | 54.55% | 4 | 36.36% | 0.040 | 0.046 | 0.039 | 0.062 | 0.021 | 0.001 | 0.006 | 0.028 |
| | | Protein reactivity | | | | | 11 | 100.00% | | | | | | | | |
| Seq ID#101 | 0.050 | 0.00001 | 11 | 9 | 100.00% | 81.82% | 3 | 27.27% | 0.022 | 0.044 | 0.019 | 0.055 | 0.027 | 0.010 | 0.033 | 0.030 |
| Seq ID#102 | 0.042 | 0.00013 | 8 | 5 | 72.73% | 45.45% | 3 | 27.27% | 0.021 | 0.041 | 0.039 | 0.052 | 0.030 | 0.006 | 0.061 | 0.024 |
| Seq ID#103 | 0.049 | 0.00003 | 9 | 5 | 81.82% | 45.45% | 3 | 27.27% | 0.043 | 0.038 | 0.035 | 0.037 | 0.017 | 0.007 | 0.058 | 0.026 |
| Seq ID#104 | 0.061 | 0.00001 | 11 | 9.000 | 100.00% | 81.82% | 6 | 54.55% | 0.018 | 0.056 | 0.034 | 0.048 | 0.021 | 0.045 | 0.023 | 0.053 |
| | | Protein reactivity | | 11 | 100.00% | | 4 | 36.36% | | | | | | | | |
| Seq ID#105 | 0.068 | 0.00002 | 10 | 11.000 | 90.91% | 72.73% | 4 | 36.36% | 0.011 | 0.009 | 0.037 | 0.044 | 0.026 | 0.007 | 0.007 | 0.035 |
| | | Protein reactivity | | 8 | | | 6 | 54.55% | | | | | | | | |
| Seq ID#106 | 0.031 | 0.00091 | 4 | 3 | 36.36% | 27.27% | 4 | 36.36% | 0.036 | 0.033 | 0.022 | 0.023 | 0.015 | 0.000 | 0.045 | 0.032 |
| Seq ID#107 | 0.042 | 0.00018 | 7 | 4 | 63.64% | 36.36% | 4 | 36.36% | 0.027 | 0.002 | 0.032 | 0.018 | 0.019 | 0.000 | 0.003 | 0.034 |
| Seq ID#108 | 0.050 | 0.00038 | 5 | 5 | 45.45% | 45.45% | 5 | 45.45% | 0.003 | 0.042 | 0.005 | 0.029 | 0.011 | 0.000 | 0.036 | 0.035 |
| Seq ID#109 | 0.059 | 0.00050 | 8 | 6 | 72.73% | 54.55% | 6 | 54.55% | 0.000 | 0.049 | 0.048 | 0.007 | 0.020 | 0.005 | 0.024 | 0.035 |
| Seq ID#110 | 0.087 | 0.00002 | 9 | 9 | 81.82% | 81.82% | 4 | 36.36% | 0.000 | 0.019 | 0.008 | 0.000 | 0.000 | 0.004 | 0.000 | 0.024 |
| Seq ID#111 | 0.031 | 0.00015 | 5 | 5 | 45.45% | 45.45% | 5 | 45.45% | 0.012 | 0.036 | 0.022 | 0.026 | 0.006 | 0.000 | 0.048 | 0.021 |
| Seq ID#112 | 0.024 | 0.00065 | 4 | 3 | 36.36% | 27.27% | 5 | 45.45% | 0.030 | 0.037 | 0.022 | 0.009 | 0.003 | 0.000 | 0.036 | 0.022 |
| | | Protein reactivity | | 11.000 | 100.00% | | 9 | 81.82% | | | | | | | | |
| Seq ID#113 | 0.039 | 0.00009 | 8 | 5 | 72.73% | 45.45% | 5 | 45.45% | 0.010 | 0.000 | 0.044 | 0.005 | 0.034 | 0.012 | 0.013 | 0.016 |
| Seq ID#114 | 0.025 | 0.04558 | 3 | 1 | 27.27% | 9.09% | 6 | 54.55% | 0.021 | 0.000 | 0.014 | 0.027 | 0.016 | 0.001 | 0.050 | 0.017 |
| Seq ID#115 | 0.077 | 0.00042 | 9 | 9 | 81.82% | 81.82% | 3 | 27.27% | 0.025 | 0.000 | 0.037 | 0.051 | 0.022 | 0.018 | 0.006 | 0.028 |
| Seq ID#116 | 0.042 | 0.00010 | 9 | 7 | 81.82% | 63.64% | 5 | 45.45% | 0.031 | 0.000 | 0.022 | 0.049 | 0.025 | 0.017 | 0.010 | 0.027 |
| Seq ID#117 | 0.061 | 0.00150 | 8 | 5 | 72.73% | 45.45% | 4 | 36.36% | 0.036 | 0.012 | 0.033 | 0.038 | 0.037 | 0.004 | 0.011 | 0.041 |
| Seq ID#118 | 0.030 | 0.00787 | 4 | 3 | 36.36% | 27.27% | 4 | 36.36% | 0.037 | 0.023 | 0.026 | 0.025 | 0.014 | 0.000 | 0.000 | 0.034 |
| Seq ID#119 | 0.053 | 0.00004 | 9 | 5 | 81.82% | 45.45% | 4 | 36.36% | 0.049 | 0.037 | 0.036 | 0.008 | 0.021 | 0.001 | 0.009 | 0.052 |

TABLE 21-continued

| Seq ID | | | | | | | | | | | | | | | | |
|---|---|---|---|---|---|---|---|---|---|---|---|---|---|---|---|---|
| Seq ID#120 | 0.028 | 0.00009 | 6 | 54.55% | | | 6 | 54.55% | 0.028 | 0.009 | 0.027 | 0.012 | 0.020 | 0.004 | 0.007 | 0.032 |
| | | Protein reactivity | | | | | | | | | | | | | | |
| Seq ID#121 | 0.049 | 0.00117 | 7 | 63.64% | 11.000 | 100.00% | 9 | 81.82% | 0.006 | 0.004 | 0.023 | 0.035 | 0.023 | 0.008 | 0.043 | 0.025 |
| Seq ID#122 | 0.068 | 0.00004 | 10 | 90.91% | 2 | 18.18% | 4 | 36.36% | 0.011 | 0.058 | 0.048 | 0.013 | 0.036 | 0.034 | 0.014 | 0.044 |
| Seq ID#123 | 0.247 | 0.00013 | 6 | 54.55% | 8 | 72.73% | 6 | 54.55% | 0.008 | 0.003 | 0.014 | 0.030 | 0.002 | 0.000 | 0.052 | 0.002 |
| Seq ID#124 | 0.154 | 0.00059 | 7 | 63.64% | 6 | 54.55% | 2 | 18.18% | 0.035 | 0.021 | 0.011 | 0.017 | 0.005 | 0.004 | 0.036 | 0.019 |
| Seq ID#125 | | | | | 6 | 54.55% | 3 | 27.27% | | | | | | | | |
| Seq ID#126 | | | | | | | | | | | | | | | | |
| Seq ID#127 | | | | | | | | | | | | | | | | |
| Seq ID#128 | 0.142 | 0.00004 | 9 | 81.82% | 5 | 45.45% | 3 | 27.27% | 0.007 | 0.047 | 0.050 | 0.006 | 0.040 | 0.020 | 0.000 | 0.000 |
| Seq ID#129 | 0.038 | 0.00176 | 6 | 54.55% | 4 | 36.36% | 4 | 36.36% | 0.035 | 0.044 | 0.058 | 0.080 | 0.026 | 0.013 | 0.000 | 0.024 |
| Seq ID#130 | 0.029 | 0.00077 | 5 | 45.45% | 3 | 27.27% | 5 | 45.45% | 0.043 | 0.041 | 0.021 | 0.024 | 0.013 | 0.004 | 0.023 | 0.030 |
| Seq ID#131 | 0.070 | 0.00127 | 5 | 45.45% | 4 | 36.36% | 4 | 36.36% | 0.009 | 0.003 | 0.045 | 0.023 | 0.031 | 0.013 | 0.007 | 0.021 |
| Seq ID#132 | 0.055 | 0.00206 | 5 | 45.45% | 5 | 45.45% | 5 | 45.45% | 0.009 | 0.014 | 0.051 | 0.066 | 0.028 | 0.004 | 0.000 | 0.000 |
| Seq ID#133 | 0.049 | 0.00002 | 9 | 81.82% | 8 | 72.73% | 6 | 54.55% | 0.008 | 0.004 | 0.023 | 0.012 | 0.045 | 0.029 | 0.012 | 0.052 |
| Seq ID#134 | 0.053 | 0.00018 | 5 | 81.82% | 5 | 45.45% | 5 | 45.45% | 0.011 | 0.023 | 0.053 | 0.000 | 0.035 | 0.014 | 0.009 | 0.039 |
| Seq ID#135 | 0.054 | 0.00006 | 9 | 81.82% | 8 | 72.73% | 6 | 54.55% | 0.013 | 0.005 | 0.051 | 0.001 | 0.023 | 0.022 | 0.017 | 0.052 |
| Seq ID#136 | | Protein reactivity | | | | | | | | | | | | | | |
| SEQ ID#137 | 0.073 | 0.00006 | 6 | 54.55% | 11.000 | 100.00% | 10 | 90.91% | 0.053 | 0.035 | 0.008 | 0.001 | 0.004 | 0.000 | 0.026 | 0.012 |
| SEQ ID#138 | 0.046 | 0.00513 | 7 | 63.64% | 6 | 54.55% | 4 | 36.36% | 0.035 | 0.050 | 0.048 | 0.056 | 0.029 | 0.003 | 0.028 | 0.017 |
| SEQ ID#139 | 0.025 | 0.00027 | 6 | 54.55% | 3 | 27.27% | 4 | 36.36% | 0.051 | 0.039 | 0.018 | 0.014 | 0.017 | 0.000 | 0.029 | 0.020 |
| SEQ ID#140 | 0.049 | 0.00328 | 5 | 45.45% | 4 | 36.36% | 5 | 45.45% | 0.044 | 0.000 | 0.033 | 0.040 | 0.021 | 0.000 | 0.059 | 0.021 |
| SEQ ID#141 | 0.039 | 0.00022 | 10 | 90.91% | 7 | 63.64% | 6 | 54.55% | 0.013 | 0.000 | 0.039 | 0.045 | 0.019 | 0.031 | 0.029 | 0.043 |
| | | Protein reactivity | | | 8.000 | 72.73% | 7 | 63.64% | | | | | | | | |

TABLE 21-continued

| | Control sera-IGRA positive | | | | | | | | | Controls | | | Cut off thresholds | |
|---|---|---|---|---|---|---|---|---|---|---|---|---|---|---|
| # Seq ID | CTR-RM009 | CTR-RM010 | CTR-RM011 | CTR-RM012 | CTR-S015 | LTBI-S016 | LTBI-S017 | LTBI-RM007 | LTBI-RM008 | AVG | MEDIAN | Stand Dev | 99-th percentile | Average+3SD |
| Seq ID#88 | 0.057 | 0.108 | 0.099 | 0.029 | 0.188 | 0.121 | 0.177 | 0.214 | 0.059 | 0.105 | 0.099 | 0.052 | 0.210 | 0.260 |
| Seq ID#89 | 0.020 | 0.016 | 0.001 | 0.004 | 0.015 | 0.049 | 0.053 | 0.075 | 0.034 | 0.026 | 0.021 | 0.020 | 0.071 | 0.087 |
| Seq ID#90 | 0.046 | 0.040 | 0.017 | 0.017 | 0.049 | 0.068 | 0.048 | 0.065 | 0.035 | 0.036 | 0.040 | 0.019 | 0.068 | 0.093 |
| Seq ID#91 | 0.020 | 0.019 | 0.011 | 0.015 | 0.040 | 0.066 | 0.052 | 0.058 | 0.028 | 0.031 | 0.027 | 0.019 | 0.065 | 0.089 |
| Seq ID#92 | 0.044 | 0.038 | 0.034 | 0.038 | 0.069 | 0.093 | 0.089 | 0.079 | 0.057 | 0.051 | 0.047 | 0.022 | 0.092 | 0.118 |
| Seq ID#93 | 0.037 | 0.029 | 0.015 | 0.018 | 0.053 | 0.085 | 0.047 | 0.048 | 0.041 | 0.034 | 0.036 | 0.019 | 0.079 | 0.092 |
| Seq ID#94 | 0.038 | 0.044 | 0.027 | 0.046 | 0.066 | 0.084 | 0.047 | 0.060 | 0.035 | 0.043 | 0.045 | 0.019 | 0.081 | 0.099 |
| Seq ID#95 | 0.045 | 0.043 | 0.031 | 0.051 | 0.038 | 0.061 | 0.048 | 0.039 | 0.048 | 0.040 | 0.043 | 0.018 | 0.068 | 0.093 |
| Seq ID#96 | 0.039 | 0.040 | 0.025 | 0.044 | 0.044 | 0.024 | 0.059 | 0.067 | 0.038 | 0.039 | 0.044 | 0.019 | 0.066 | 0.095 |
| Seq ID#97 | 0.050 | 0.036 | 0.016 | 0.041 | 0.037 | 0.059 | 0.044 | 0.041 | 0.044 | 0.038 | 0.041 | 0.019 | 0.066 | 0.096 |
| Seq ID#98 | 0.053 | 0.067 | 0.037 | 0.056 | 0.081 | 0.069 | 0.061 | 0.108 | 0.053 | 0.046 | 0.048 | 0.027 | 0.104 | 0.127 |
| Seq ID#99 | 0.033 | 0.030 | 0.023 | 0.031 | 0.025 | 0.062 | 0.045 | 0.062 | 0.027 | 0.033 | 0.033 | 0.014 | 0.062 | 0.077 |
| Seq ID#100 | 0.036 | 0.029 | 0.028 | 0.047 | 0.041 | 0.044 | 0.051 | 0.024 | 0.049 | 0.035 | 0.039 | 0.016 | 0.060 | 0.082 |
| Seq ID#101 | 0.042 | 0.027 | 0.008 | 0.042 | 0.026 | 0.051 | 0.054 | 0.039 | 0.041 | 0.033 | 0.033 | 0.014 | 0.055 | 0.076 |
| Seq ID#102 | 0.025 | 0.023 | 0.020 | 0.035 | 0.054 | 0.046 | 0.051 | 0.044 | 0.035 | 0.036 | 0.035 | 0.015 | 0.060 | 0.080 |
| Seq ID#103 | 0.023 | 0.018 | 0.006 | 0.040 | 0.034 | 0.046 | 0.037 | 0.061 | 0.033 | 0.033 | 0.035 | 0.016 | 0.061 | 0.079 |
| Seq ID#104 | 0.024 | 0.031 | 0.031 | 0.034 | 0.031 | 0.044 | 0.044 | 0.037 | 0.050 | 0.037 | 0.034 | 0.012 | 0.055 | 0.072 |
| Seq ID#105 | 0.037 | 0.038 | 0.034 | 0.004 | 0.053 | 0.038 | 0.048 | 0.044 | 0.056 | 0.031 | 0.037 | 0.017 | 0.055 | 0.082 |
| Seq ID#106 | 0.023 | 0.015 | 0.021 | 0.022 | 0.017 | 0.047 | 0.019 | 0.068 | 0.028 | 0.027 | 0.023 | 0.016 | 0.065 | 0.074 |
| Seq ID#107 | 0.009 | 0.026 | 0.022 | 0.044 | 0.037 | 0.049 | 0.044 | 0.071 | 0.039 | 0.028 | 0.027 | 0.019 | 0.067 | 0.084 |
| Seq ID#108 | 0.019 | 0.026 | 0.019 | 0.038 | 0.047 | 0.041 | 0.035 | 0.092 | 0.045 | 0.031 | 0.035 | 0.022 | 0.085 | 0.096 |
| Seq ID#109 | 0.040 | 0.037 | 0.024 | 0.005 | 0.074 | 0.082 | 0.055 | 0.065 | 0.052 | 0.036 | 0.037 | 0.025 | 0.081 | 0.111 |
| Seq ID#110 | 0.029 | 0.000 | 0.045 | 0.041 | 0.044 | 0.057 | 0.063 | 0.031 | 0.048 | 0.024 | 0.024 | 0.022 | 0.062 | 0.091 |
| Seq ID#111 | 0.013 | 0.000 | 0.009 | 0.024 | 0.026 | 0.022 | 0.024 | 0.064 | 0.030 | 0.022 | 0.022 | 0.016 | 0.061 | 0.072 |

TABLE 21-continued

| | | | | | | | | | | | |
|---|---|---|---|---|---|---|---|---|---|---|---|
| Seq ID#112 | 0.012 | 0.016 | 0.008 | 0.008 | 0.014 | 0.030 | 0.016 | 0.008 | 0.067 | 0.020 | 0.016 | 0.017 | 0.062 | 0.069 |
| Seq ID#113 | 0.024 | 0.041 | 0.016 | 0.025 | 0.062 | 0.009 | 0.049 | 0.079 | 0.046 | 0.028 | 0.024 | 0.022 | 0.076 | 0.094 |
| Seq ID#114 | 0.020 | 0.017 | 0.008 | 0.008 | 0.017 | 0.039 | 0.041 | 0.056 | 0.028 | 0.022 | 0.017 | 0.016 | 0.055 | 0.070 |
| Seq ID#115 | 0.007 | 0.026 | 0.022 | 0.026 | 0.037 | 0.061 | 0.021 | 0.042 | 0.039 | 0.027 | 0.026 | 0.016 | 0.059 | 0.075 |
| Seq ID#116 | 0.003 | 0.038 | 0.023 | 0.038 | 0.036 | 0.016 | 0.014 | 0.007 | 0.047 | 0.024 | 0.023 | 0.015 | 0.048 | 0.068 |
| Seq ID#117 | 0.028 | 0.029 | 0.006 | 0.012 | 0.037 | 0.054 | 0.044 | 0.065 | 0.049 | 0.031 | 0.036 | 0.017 | 0.063 | 0.084 |
| Seq ID#118 | 0.021 | 0.020 | 0.006 | 0.014 | 0.021 | 0.057 | 0.044 | 0.048 | 0.030 | 0.024 | 0.023 | 0.016 | 0.055 | 0.072 |
| Seq ID#119 | 0.034 | 0.033 | 0.018 | 0.049 | 0.044 | 0.060 | 0.036 | 0.054 | 0.029 | 0.033 | 0.036 | 0.017 | 0.059 | 0.085 |
| Seq ID#120 | 0.030 | 0.027 | 0.011 | 0.011 | 0.058 | 0.006 | 0.032 | 0.002 | 0.031 | 0.020 | 0.020 | 0.014 | 0.053 | 0.064 |
| Seq ID#121 | 0.021 | 0.001 | 0.004 | 0.005 | 0.012 | 0.039 | 0.031 | 0.022 | 0.035 | 0.020 | 0.022 | 0.014 | 0.042 | 0.061 |
| Seq ID#122 | 0.058 | 0.019 | 0.008 | 0.047 | 0.062 | 0.056 | 0.047 | 0.078 | 0.053 | 0.040 | 0.047 | 0.021 | 0.075 | 0.103 |
| Seq ID#123 | 0.005 | 0.024 | 0.020 | 0.000 | 0.002 | 0.030 | 0.033 | 0.004 | 0.005 | 0.014 | 0.005 | 0.015 | 0.049 | 0.059 |
| Seq ID#124 | 0.027 | 0.017 | 0.014 | 0.006 | 0.029 | 0.031 | 0.001 | 0.006 | 0.008 | 0.017 | 0.017 | 0.011 | 0.036 | 0.051 |
| Seq ID#125 | | | | | | | | | | | | | | |
| Seq ID#126 | | | | | | | | | | | | | | |
| Seq ID#127 | | | | | | | | | | | | | | |
| Seq ID#128 | 0.007 | 0.043 | 0.009 | 0.034 | 0.080 | 0.070 | 0.073 | 0.082 | 0.039 | 0.036 | 0.039 | 0.029 | 0.082 | 0.121 |
| Seq ID#129 | 0.003 | 0.009 | 0.002 | 0.037 | 0.065 | 0.068 | 0.072 | 0.083 | 0.036 | 0.038 | 0.036 | 0.028 | 0.082 | 0.123 |
| Seq ID#130 | 0.009 | 0.018 | 0.017 | 0.026 | 0.018 | 0.041 | 0.032 | 0.070 | 0.051 | 0.028 | 0.024 | 0.017 | 0.067 | 0.078 |
| Seq ID#131 | 0.035 | 0.034 | 0.028 | 0.031 | 0.032 | 0.071 | 0.063 | 0.007 | 0.005 | 0.027 | 0.028 | 0.020 | 0.070 | 0.085 |
| Seq ID#132 | 0.001 | 0.033 | 0.031 | 0.028 | 0.058 | 0.092 | 0.077 | 0.084 | 0.048 | 0.037 | 0.031 | 0.031 | 0.090 | 0.128 |
| Seq ID#133 | 0.007 | 0.041 | 0.040 | 0.006 | 0.044 | 0.010 | 0.053 | 0.082 | 0.009 | 0.028 | 0.023 | 0.022 | 0.077 | 0.095 |
| Seq ID#134 | 0.049 | 0.041 | 0.037 | 0.031 | 0.066 | 0.045 | 0.019 | 0.068 | 0.040 | 0.034 | 0.037 | 0.019 | 0.068 | 0.092 |
| Seq ID#135 | 0.042 | 0.024 | 0.031 | 0.044 | 0.004 | 0.031 | 0.006 | 0.019 | 0.052 | 0.026 | 0.023 | 0.017 | 0.052 | 0.078 |
| Seq ID#136 | | | | | | | | | | | | | | |

TABLE 21-continued

| | | | | | | | | | | |
|---|---|---|---|---|---|---|---|---|---|---|
| SEQ ID#137 | 0.006 | 0.012 | 0.002 | 0.010 | 0.015 | 0.035 | 0.038 | 0.062 | 0.024 | 0.020 | 0.012 | 0.019 | 0.061 | 0.076 |
| SEQ ID#138 | 0.018 | 0.025 | 0.004 | 0.039 | 0.034 | 0.047 | 0.035 | 0.022 | 0.041 | 0.031 | 0.034 | 0.015 | 0.055 | 0.077 |
| SEQ ID#139 | 0.017 | 0.011 | 0.004 | 0.007 | 0.037 | 0.029 | 0.035 | 0.057 | 0.030 | 0.024 | 0.020 | 0.016 | 0.056 | 0.072 |
| SEQ ID#140 | 0.028 | 0.020 | 0.007 | 0.016 | 0.028 | 0.023 | 0.015 | 0.045 | 0.025 | 0.025 | 0.023 | 0.016 | 0.057 | 0.072 |
| SEQ ID#141 | 0.047 | 0.037 | 0.050 | 0.032 | 0.027 | 0.037 | 0.036 | 0.038 | 0.033 | 0.033 | 0.036 | 0.013 | 0.049 | 0.070 |

FURTHER ASPECTS OF THE INVENTION

1) Use of any of the 7 proteins, derived from *Mycobacterium tuberculosis* and comprising at least one T-cell or B-cell epitope, alone or in group or in association with other proteins of *Mycobacterium tuberculosis* as biomarkers in an in vitro test for the detection of *Mycobacterium tuberculosis* infection or diseases, said proteins being chosen from the group consisting of SeqID#1-#7.
2) Use accordingly to item 1, wherein any of the T-cell epitopes in the 7 proteins are used as single antigen, alone or in group or in association with other protein antigens as biomarkers in an in vitro test for the detection of *Mycobacterium tuberculosis* infection or diseases, said protein epitope being chosen from the group consisting of SeqID#8-#87
3) Use accordingly to item 1, wherein any of the B-cell epitopes (either continuous or discontinuous) or any of the mimotope epitopes in the 7 proteins are used as single antigen, alone or in group or in association with other protein antigens as biomarkers in an in vitro test for the detection of *Mycobacterium tuberculosis* infection or diseases, said protein epitope being chosen from the group consisting of SeqID#88-#136
4) Use according to item 1, 2 and 3, wherein an homolog or orthologue of the proteins are used as whole, portion, fragments, or homology fragments with sequence homology equal or above 80%. Homology is defined as follow:
a. an amino acid sequence with at least 80% similarity in comparison to one of said protein or peptides in items 1-3, after optimal alignment; or
b. peptide fragment of the proteins and peptides as defined in items 1-3 containing a B-cell and/or T-cell epitope (seqID#8-136) or a chemical analog thereof;
5) Use according to items 1-4 in an in vitro test for the detection of *Mycobacterium* infection in a subject.
6) Use of item 5 wherein the *Mycobacterium* species is selected from *M. tuberculosis, M. bovis, M. bovis* BCG, *M. africanum, M. canetti, M. caprae, M. microti, M. pinnipedii, M. avium, M. avium paratuberculosis, M. avium silvaticum, M. avium "hominissuis", M. colombiense, M. asiaticum, M. gordonae, M. gastri, M. kansasii, M. hiberniae, M. nonchromogenicum, M. terrae, M. triviale, M. ulcerans, M. pseudoshottsii, M. shottsii, M. triplex, M. genavense, M. florentinum, M. lentiflavum, M. palustre, M. kubicae, M. parascrofulaceum, M. heidelbergense, M. interjectum, M. simiae, M. branderi, M. cookii, M. celatum, M. bohemicum, M. haemophilum, M. malmoense, M. szulgai, M. leprae, M. lepraemurium, M. lepromatosis, M. africanum, M. botniense, M. chimaera, M. conspicuum, M. doricum, M. farcinogenes, M. heckeshornense, M. intracellulare, M. lacus, M. marinum, M. monacense, M. montefiorense, M. murale, M. nebraskense, M. saskatchewanense, M. scrofulaceum, M. shimoidei, M. tusciae, M. xenopi, M. intermedium, M. abscessus, M. chelonae, M. bolletii, M. fortuitum, M. fortuitum subsp. acetamidolyticum, M. boenickei, M. peregrinum, M. porcinum, M. senegalense, M. septicum, M. neworleansense, M. houstonense, M. mucogenicum, M. mageritense, M. brisbanense, M. cosmeticum, M. parafortuitum, M. austroafricanum, M. diernhoferi, M. hodleri, M. neoaurum, M. frederiksbergense, M. aurum, M. vaccae, M. chitae, M. fallax, M. confluentis, M. flavescens, M. madagascariense, M. phlei, M. smegmatis, M. goodii, M. wolinskyi, M. thermoresistibile, M. gadium, M. komossense, M. obuense, M. sphagni, M. agri, M. aichiense, M. alvei, M. arupense, M brumae, M. canariasense, M. chubuense, M. conceptionense, M. duvalii, M. elephantis, M. gilvum, M. hassiacum, M. holsaticum, M. immunogenum, M. massiliense, M. moriokaense, M. psychrotolerans, M. pyrenivorans, M. vanbaalenii, M. pulveris, M. arosiense, M. aubagnense, M. caprae, M. chlorophenolicum, M. fluoroanthenivorans, M. kumamotonense, M. novocastrense, M. parmense, M. phocaicum, M. poriferae, M. rhodesiae, M. seoulense* and *M. tokaiense.*
7) Use according to item 5 and 6 wherein the *Mycobacterium* species is any of the *Mycobacterium tuberculosis*-complex.
8) Use according to item 5-7 wherein the subject is an human.
9) Use according to item 5-7 wherein the subject is a non human animal.
10) Isolated nucleic acid molecule encoding for the protein according to item 1 or peptides according to item 2 and 3.
11) Vector comprising the nucleic acid molecule according to Item 10.
12) Kit comprising a container, said container comprising at least one protein or peptides or derived nucleic acid sequence according to item 1, 2, 3, 10, 11
13) Method for in vitro diagnosing infection by a *Mycobacterium* species in a subject or animal, said method comprising incubating a blood sample comprising lymphocytes from said subject in the presence of at least one biomarker selected as for item 1 and 2.
14) Method for in vitro diagnosing by antibody specific detection for the protein, peptides or mimotopes according to item 1, 3.
15) Vaccine for the treatment or prophylaxis of infection by a *Mycobacterium* species, said vaccine comprising or consisting of at least one agent selected as for items 1-4.

The invention claimed is:

1. A method for diagnosing *Mycobacterium tuberculosis* (*M. tuberculosis*) complex infection in a subject, comprising detecting in vitro using a sample obtained from the subject, an immune response to an *M. tuberculosis* protein or antigenic fragment thereof selected from the group consisting of (a) Rv0840c (SEQ ID NO: 6) or one or more antigenic fragments thereof; (b) TBFG_13463 (SEQ ID NO: 1) or one or more antigenic fragments thereof (c) Rv1677 (SEQ ID NO: 7) or one or more antigenic fragments thereof (d) Rv3845 (SEQ ID NO: 4) or one or more antigenic fragments thereof; (e) Rv1495 (SEQ ID NO: 5) or one or more antigenic fragments thereof; and (f) Mtub2_17866 (SEQ ID NO: 2) or one or more antigenic fragments thereof; and a combination thereof.

2. The method according to claim 1, comprising detecting in vitro an immune response to an *M. tuberculosis* protein or antigenic fragment thereof selected from the group consisting of (i) Rv0840c (SEQ ID NO: 6) or one or more antigenic fragments thereof; (ii) TBFG_13463 (SEQ ID NO: 1) or one or more antigenic fragments thereof; (iii) Rv1677 (SEQ ID NO: 7) or one or more antigenic fragments thereof; (iv) Rv3845 (SEQ ID NO: 4) or one or more antigenic fragments thereof; and a combination thereof.

3. The method according to claim 1, comprising detecting in vitro an immune response to Rv0840c (SEQ ID NO: 6) or one or more antigenic fragments thereof.

4. The method according to claim 1, further comprising detecting in vitro an immune response to one or more additional *M. tuberculosis* proteins or antigenic fragments thereof.

5. The method according to claim 4, wherein the one or more additional *M. tuberculosis* proteins comprises a RD1 protein.

6. The method according to claim 5, wherein the RD1 protein is CFP-10 or ESAT-6.

7. The method according to claim 1, comprising detecting in vitro an immune response to a pool of protein fragments, wherein the pool comprises two or more protein fragments, and wherein the protein fragments are antigenic fragments of one or more of TBFG_13463 (SEQ ID NO: 1), Mtub2_17866 (SEQ ID NO: 2), Rv3845 (SEQ ID NO: 4), Rv1495 (SEQ ID NO: 5), Rv0840c (SEQ ID NO: 6) and Rv1677 (SEQ ID NO: 7).

8. The method according to claim 7, wherein the pool of protein fragments comprises a protein fragment library encompassing at least 80% of the sequence of TBFG_13463 (SEQ ID NO: 1), Mtub2_17866 (SEQ ID NO: 2), Rv3845 (SEQ ID NO: 4), Rv1495 (SEQ ID NO: 5), Rv0840c (SEQ ID NO: 6) or Rv1677 (SEQ ID NO: 7).

9. The method according to claim 7, wherein the pool of protein fragments comprises a protein fragment library encompassing the entire sequence of TBFG_13463 (SEQ ID NO: 1), Mtub2_17866 (SEQ ID NO: 2), Rv3845 (SEQ ID NO: 4), Rv1495 (SEQ ID NO: 5), Rv0840c (SEQ ID NO: 6) or Rv1677 (SEQ ID NO: 7).

10. The method according to claim 8, wherein the pool comprises two or more protein fragments whose sequences overlap.

11. The method according to claim 10, wherein the sequences overlap by 11 amino acids.

12. The method according to claim 10, wherein the *M. tuberculosis* protein fragments are each 15 amino acids in length.

13. The method according to claim 7, wherein one or more of the antigenic fragments comprises a T cell epitope or a B cell epitope.

14. The method according to claim 13, wherein the T cell epitope is a CD4 epitope.

15. The method according to claim 13, wherein the T cell epitope is a CD8 epitope.

16. The method according to claim 1, wherein the immune response is an in vitro cell mediated immune response.

17. The method according to claim 1, wherein the immune response is a T-cell response.

18. The method according to claim 17, wherein the T-cell response is cytokine secretion or T-cell proliferation.

19. The method according to claim 18, wherein the cytokine secretion is interferon gamma (IFNγ) secretion.

20. The method according to claim 1, wherein the immune response is a B-cell response.

21. The method according to claim 20, wherein the B-cell response is antibody secretion or B-cell proliferation.

22. The method according to claim 1, wherein the immune response is the production of antibodies against one or more of (a) to (f) as defined in claim 1.

23. The method according to claim 1, wherein the method comprises performing an enzyme-linked immunospot assay (ELISPOT).

24. The method according to claim 1, wherein the method comprises contacting a population of immune cells obtained from the subject with one or more of the *M. tuberculosis* proteins or antigenic fragments thereof of (a) to (f) as defined in claim 1.

25. The method according to claim 24, wherein the method comprises contacting the population of immune cells obtained from the subject with two or more of the *M. tuberculosis* proteins or antigenic fragments thereof.

26. The method according to claim 24, wherein the population of immune cells is further contacted with one or more additional *M. tuberculosis* proteins or antigenic fragments thereof.

27. The method according to claim 25, wherein each of the two or more *M. tuberculosis* proteins or antigenic fragments thereof is contacted with a different population of immune cells.

28. The method according to claim 24, the method further comprising:
detecting in vitro an immune response to one or more additional *M. tuberculosis* proteins or antigenic fragments thereof, and
wherein each of the additional *M. tuberculosis* proteins or antigenic fragments thereof, is contacted with a different population of immune cells.

29. A kit for diagnosing *Mycobacterium tuberculosis* (*M. tuberculosis*) complex infection in a subject, comprising one or more antigenic fragments of a pool of protein fragments from a protein fragment library encompassing at least 80% of the sequence of TBFG_13463 (SEQ ID NO: 1), Mtub2_17866 (SEQ ID NO: 2), Rv3845 (SEQ ID NO: 4), Rv1495 (SEQ ID NO: 5), Rv0840c (SEQ ID NO: 6) or Rv1677 (SEQ ID NO: 7).

30. The kit according to claim 29, further comprising a means for detecting the immune response.

31. A method of treating *M. tuberculosis* complex infection in a subject, the method comprising administering to the subject a composition comprising one or more of the *M. tuberculosis* proteins or antigenic fragments thereof of (a) to (f) as defined in claim 1.

32. The method according to claim 4, wherein the one or more additional *M. tuberculosis* proteins comprises Rv2654c (SEQ ID NO: 3) or one or more antigenic fragments thereof.

33. The method according to claim 1, wherein the *M. tuberculosis* protein or antigenic fragment thereof comprises 5 or more amino acids.

34. The method according to claim 1, wherein the *M. tuberculosis* protein or antigenic fragment thereof comprises from about 5 to about 27 amino acids.

35. The method of claim 7, wherein the two or more protein fragments are antigenic fragments of the same protein.

36. The method of claim 7, wherein the two or more protein fragments are antigenic fragments of different proteins.

37. The method of claim 7, further comprising detecting in vitro an immune response to more than one pool of protein fragments
wherein each pool of protein fragments comprises two or more protein fragments, and
wherein the protein fragments are antigenic fragments of one or more of TBFG_13463 (SEQ ID NO: 1), Mtub2_17866 (SEQ ID NO: 2), Rv3845 (SEQ ID NO: 4), Rv1495 (SEQ ID NO: 5), Rv0840c (SEQ ID NO: 6) and Rv1677 (SEQ ID NO: 7).

38. The method of claim 37, wherein each pool of protein fragments comprise two or more antigenic fragments of the same protein or two or more antigenic fragments of different proteins.

* * * * *

UNITED STATES PATENT AND TRADEMARK OFFICE
CERTIFICATE OF CORRECTION

PATENT NO. : 10,295,538 B2
APPLICATION NO. : 15/503151
DATED : May 21, 2019
INVENTOR(S) : Massimo Amicosante et al.

It is certified that error appears in the above-identified patent and that said Letters Patent is hereby corrected as shown below:

In the Specification

1. Column 2, beginning at Line 14 and ending at Line 15, please delete:
"RIM antigens used in IGRAs include ESAT6 and CFP10."
And insert:
--(RD)1 antigens used in IGRAs include ESAT6 and CFP10.--

2. Column 9, beginning at Line 26 and ending at Line 28, please delete:
"In particular, the in vitro cytokine-based CMI response to the proteins and peptides or the present invention may be detected."
And insert:
--In particular, the in vitro cytokine-based CMI response to the proteins and peptides of the present invention may be detected.--

3. Column 12, beginning at Line 28 and ending at Line 31, please delete:
"As B-cells recognise antigen via the B-cell receptor (BCR), a B-cell epitope may be the part of an antigen that binds to (i.e. is recognised) by the T-cell receptor."
And insert:
--As B-cells recognise antigen via the B-cell receptor (BCR), a B-cell epitope may be the part of an antigen that binds to (i.e. is recognised) by the B-cell receptor.--

4. Column 24, Line 3 and ending at Line 4, please delete:
"Sequence of HLA class II epitopes"
And insert:
--Sequence of HLA class I epitopes--

5. Column 23, Line 28 and ending at Line 29, please delete:
"Sequence of HLA class II epitopes"
And insert:
--Sequence of HLA class I epitopes--

Signed and Sealed this
Third Day of September, 2019

Andrei Iancu
*Director of the United States Patent and Trademark Office*

6. Column 29, Line 16 and ending at Line 20, please delete:
"The OD values in Table 20 show that there are significantly higher levels of antibodies to SEQ ID NO: 88 to SEQ ID NO: 141 in subjects having active *M. tuberculosis* complex infection compared to control subjects (i.e. healthy individuals or subjects having LTBI)."
And insert:
--The OD values in Table 21 show that there are significantly higher levels of antibodies to SEQ ID NO: 88 to SEQ ID NO: 141 in subjects having active *M. tuberculosis* complex infection compared to control subjects (i.e. healthy individuals or subjects having LTBI).--

7. Column 34, Line 63, please delete:
"SEQ ID NO: 13 VWFQRIGGGPGRPLLWHGGPGLPH"
And insert:
--SEQ ID NO: 13 VWFQRIGGGPGRPLLVVHGGPGLPH--

8. Column 35, Line 16, please delete:
"SEQ ID NO: 80 RTWNETYLCRTPW"
And insert:
--SEQ ID NO: 80 RTWNETYLCRTRPW--